United States Patent
Tsuruoka

(10) Patent No.: US 8,396,289 B2
(45) Date of Patent: Mar. 12, 2013

(54) DISCRIMINATION APPARATUS, DISCRIMINATION METHOD AND PROGRAM RECORDING MEDIUM

(75) Inventor: Takao Tsuruoka, Machida (JP)

(73) Assignee: Olympus Corporation, Tokyo (JP)

( * ) Notice: Subject to any disclaimer, the term of this patent is extended or adjusted under 35 U.S.C. 154(b) by 538 days.

(21) Appl. No.: 12/628,280

(22) Filed: Dec. 1, 2009

(65) Prior Publication Data
US 2010/0195904 A1   Aug. 5, 2010

(30) Foreign Application Priority Data
Dec. 1, 2008 (JP) .................................. 2008-306464

(51) Int. Cl.
*G06K 9/00* (2006.01)

(52) U.S. Cl. ........................................ 382/165; 382/128
(58) Field of Classification Search .................. 382/128, 382/165; 348/45; 600/109
See application file for complete search history.

(56) References Cited

U.S. PATENT DOCUMENTS

| 7,172,553 | B2 | 2/2007 | Ueno et al. |
| 7,463,287 | B2 * | 12/2008 | Aotsuka ............. 348/223.1 |
| 7,570,287 | B2 | 8/2009 | Tsuruoka |
| 7,944,466 | B2 * | 5/2011 | Abe et al. ............. 348/71 |
| 8,125,543 | B2 * | 2/2012 | Cho ............................ 348/241 |
| 2003/0176768 | A1 | 9/2003 | Gono et al. |
| 2006/0012808 | A1 * | 1/2006 | Mizukura et al. ............. 358/1.9 |
| 2006/0066736 | A1 | 3/2006 | Tsuruoka |
| 2006/0203100 | A1 * | 9/2006 | Ajito et al. ................. 348/220.1 |
| 2009/0091614 | A1 * | 4/2009 | Gono et al. ....................... 348/68 |

FOREIGN PATENT DOCUMENTS

JP  2003-93336  4/2003

* cited by examiner

*Primary Examiner* — Samir Ahmed
(74) *Attorney, Agent, or Firm* — Scully, Scott, Murphy & Presser, P.C.

(57) ABSTRACT

A discrimination apparatus includes a separating unit configured to separate kinds (N being a natural number of 2 or greater) of color signals forming an image signal obtained by image acquisition of a subject with a color imaging system into kinds (M being a natural number of 1 or greater, M≦N) of wavelength ranges, based on known spectral characteristics of a subject to be discriminated, at least one of the separated wavelength ranges including a plurality of color signals. The discrimination apparatus further includes a noise estimating unit configured to estimate a noise amount in each predetermined unit area in each of the wavelength ranges separated by the separating unit, and a noise reducing unit configured to perform a noise reducing processing on each of the wavelength ranges separated by the separating unit, based on the noise amount estimated by the noise estimating unit. The discrimination apparatus further includes a discriminating unit configured to perform a discriminating processing on the subject to be discriminated, based on the color signals in the wavelength ranges noise-reduced by the noise reducing unit.

20 Claims, 24 Drawing Sheets

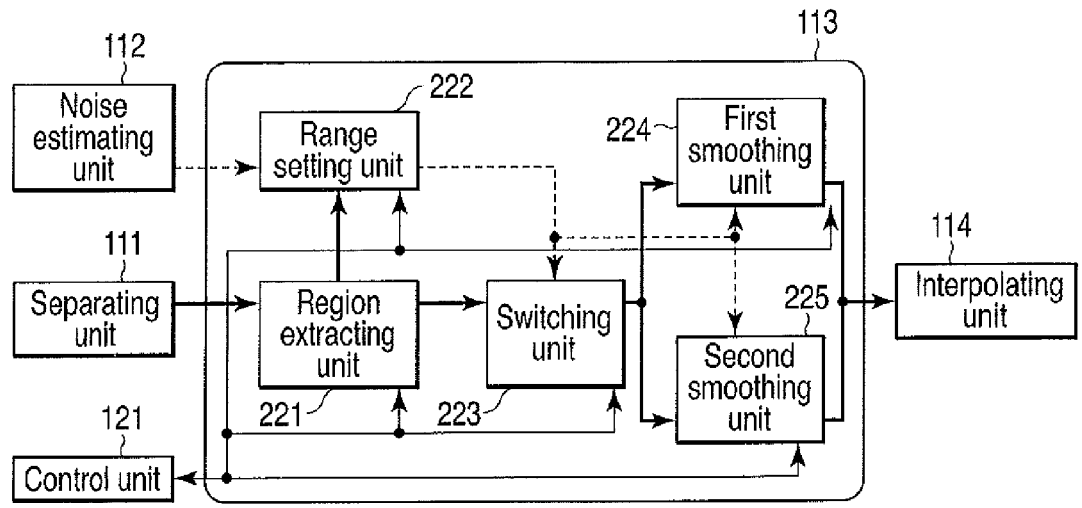
F I G. 1 5
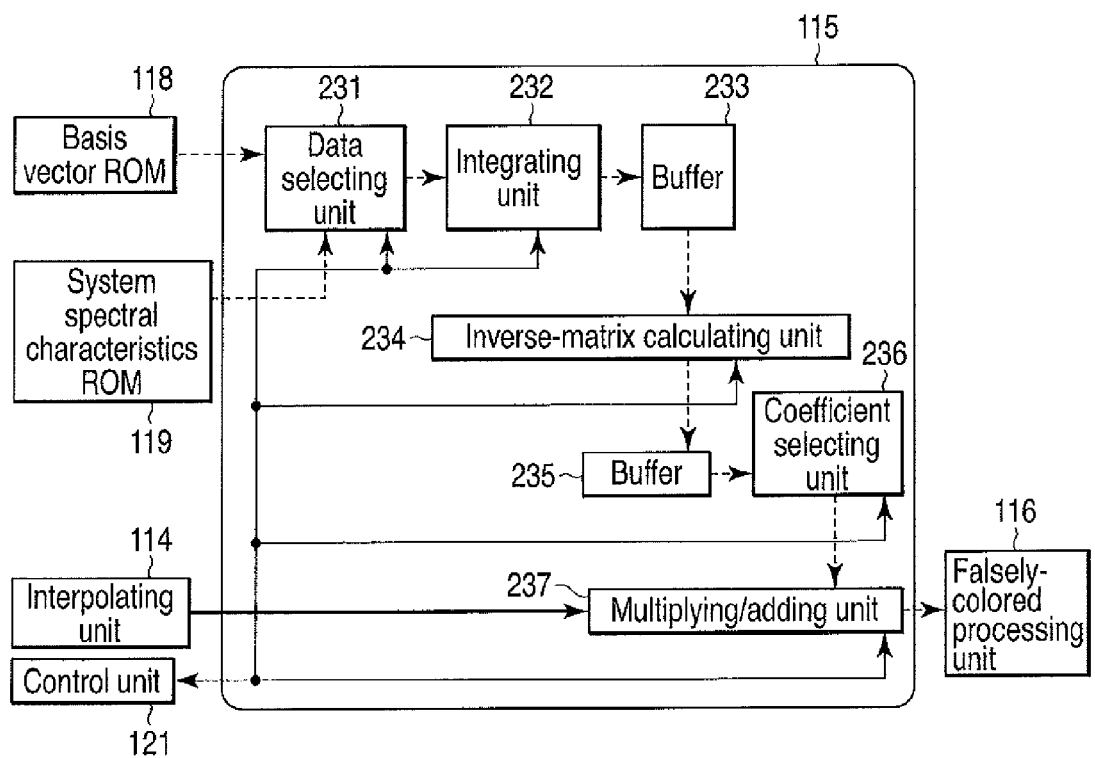
F I G. 1 6

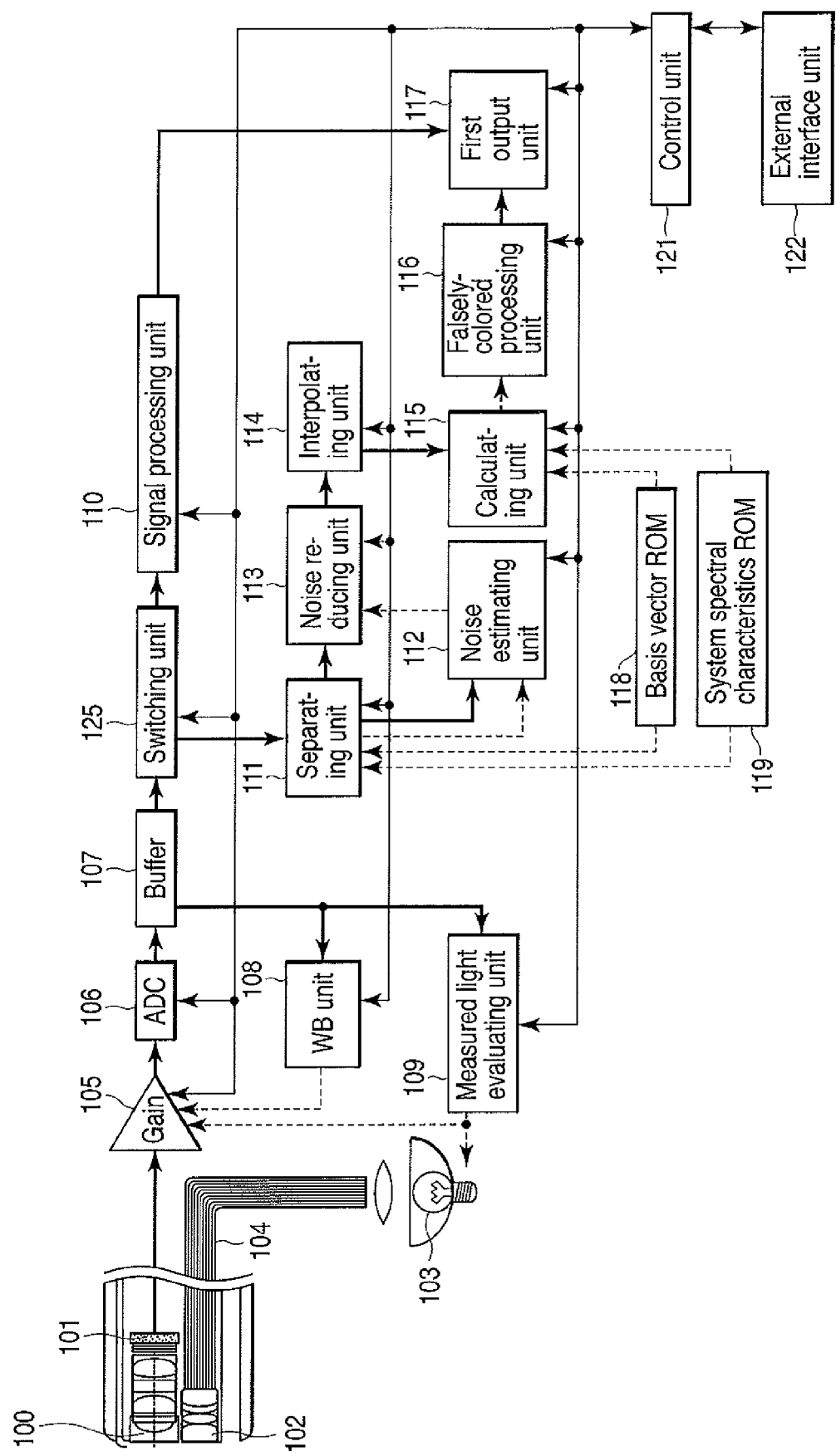
F I G. 17

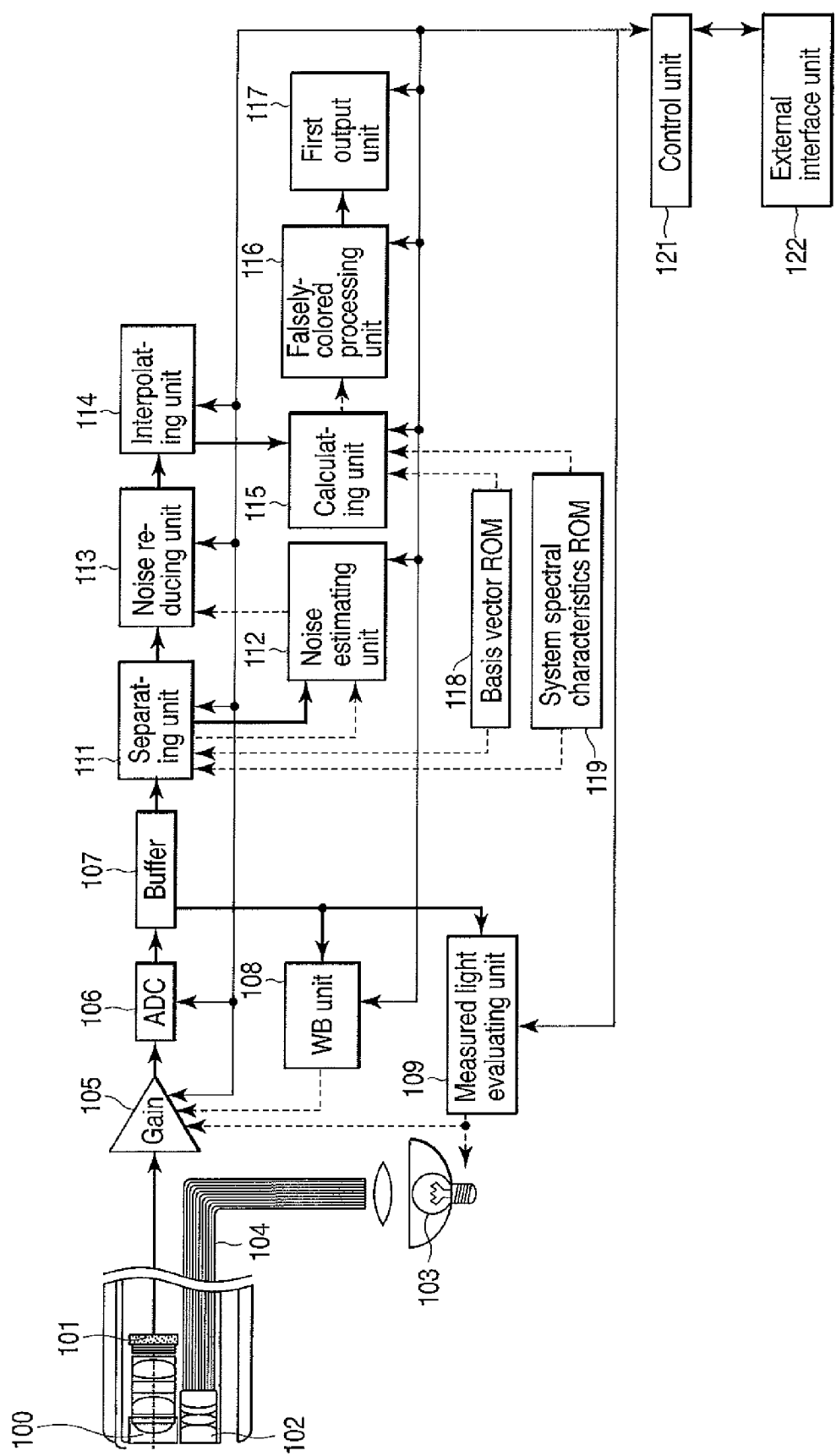
F I G. 18

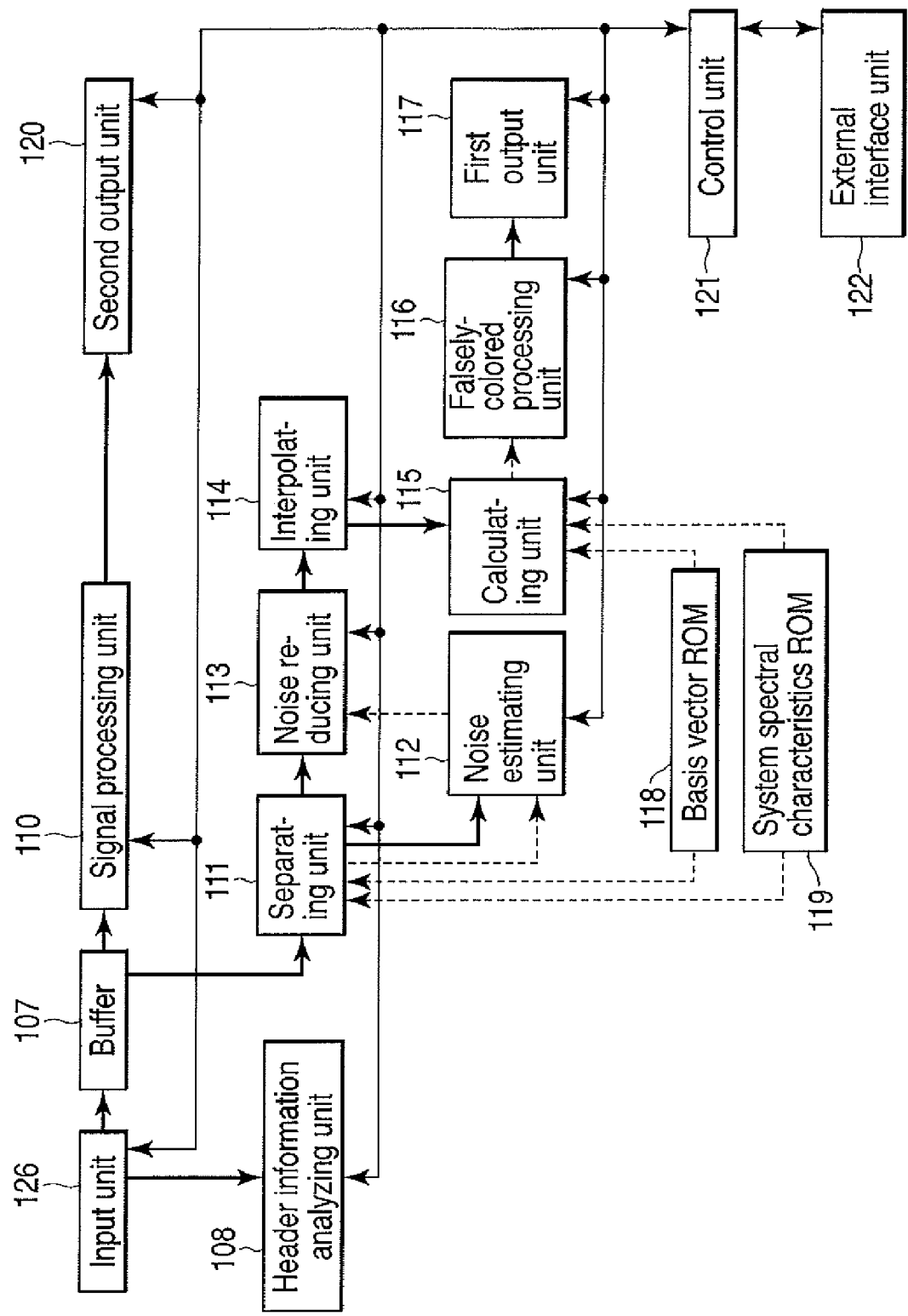
F I G. 19

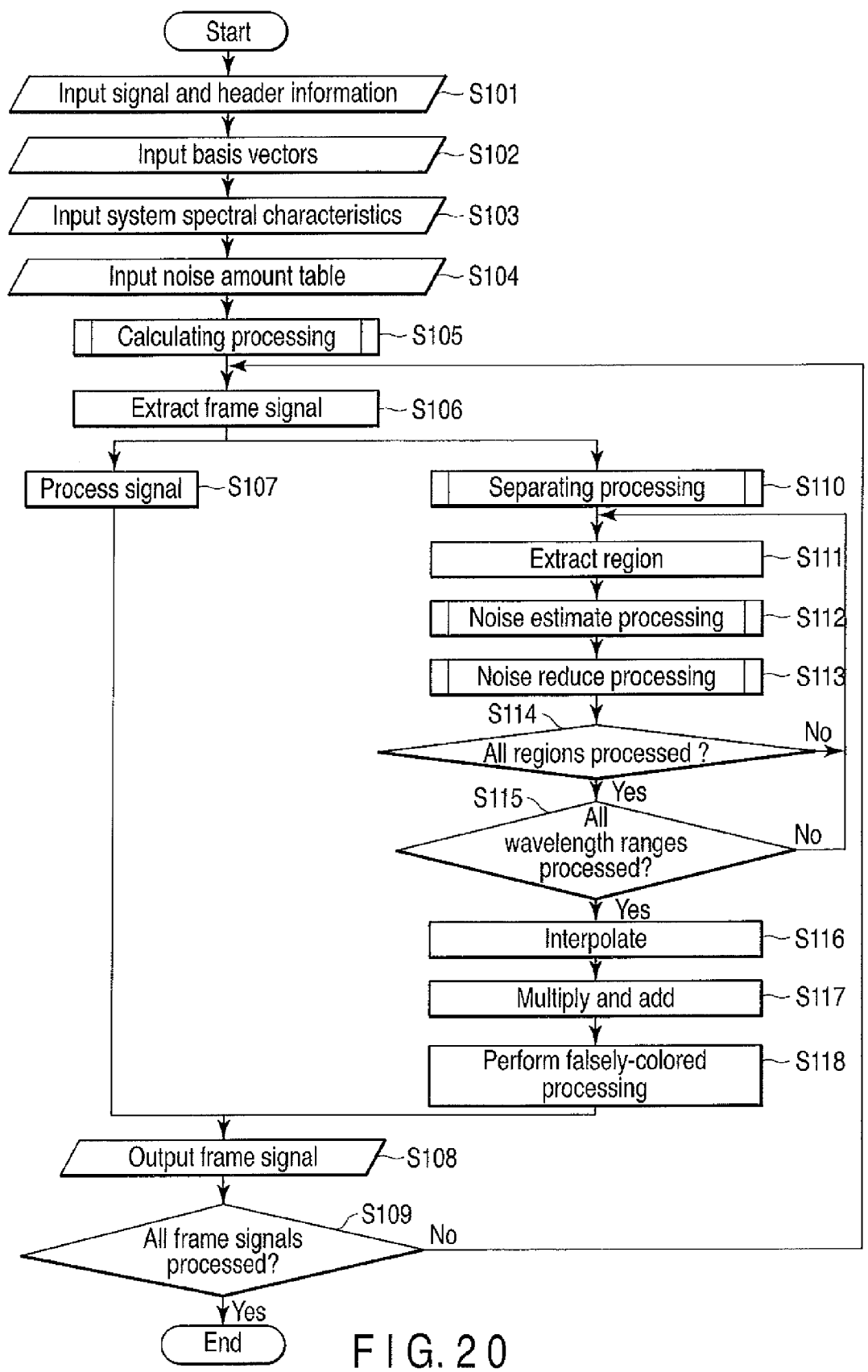
F I G. 2 0

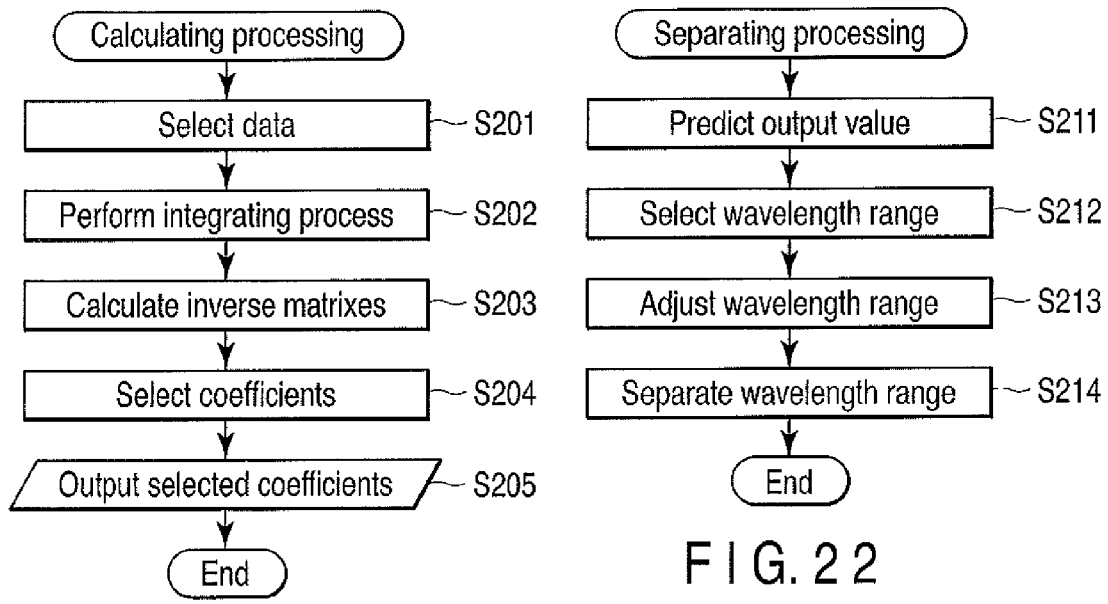
FIG. 21
FIG. 22
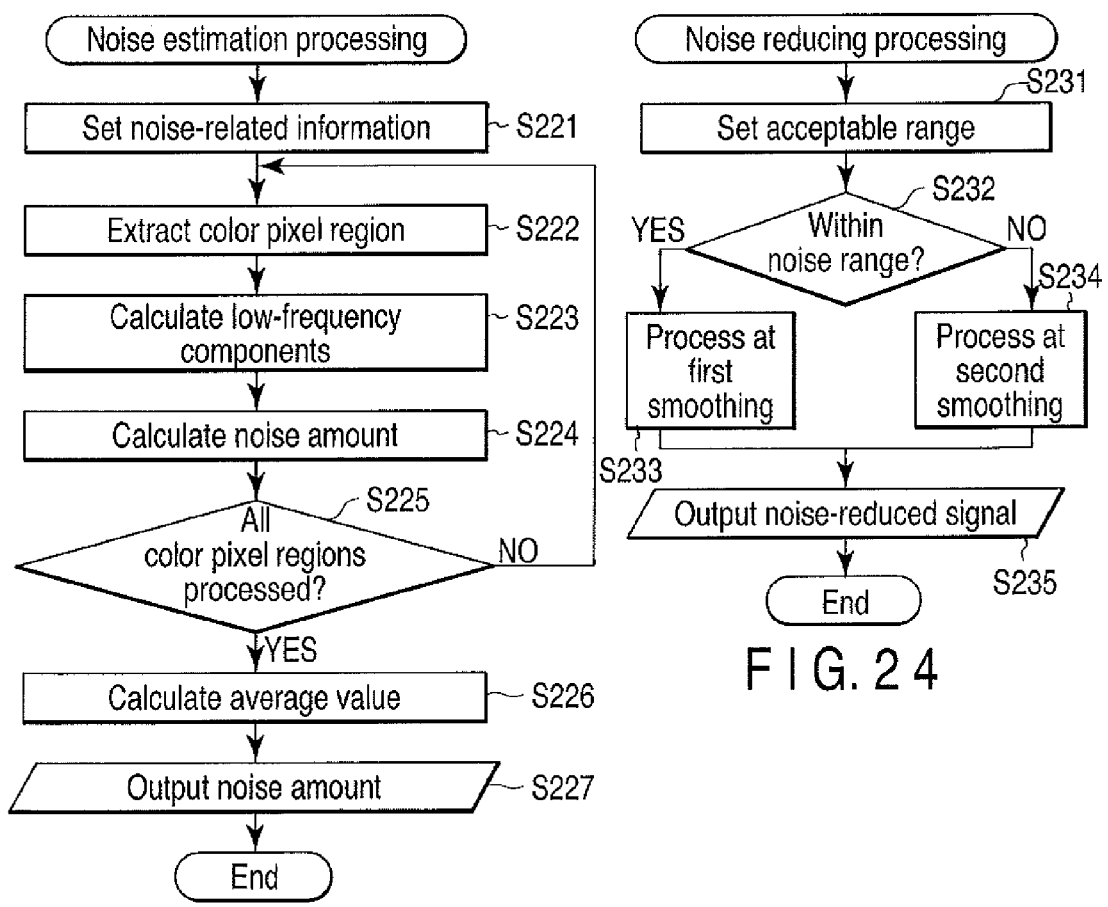
FIG. 23
FIG. 24

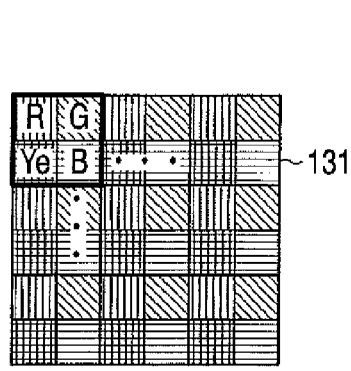
F I G. 26
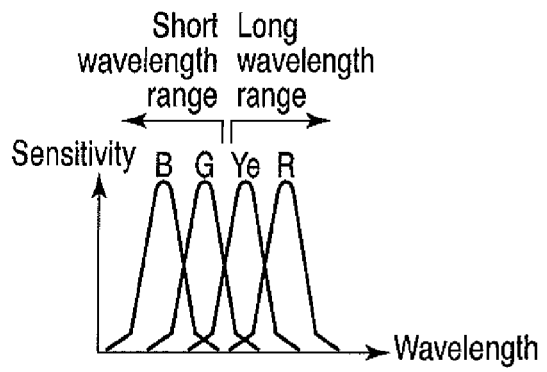
F I G. 27
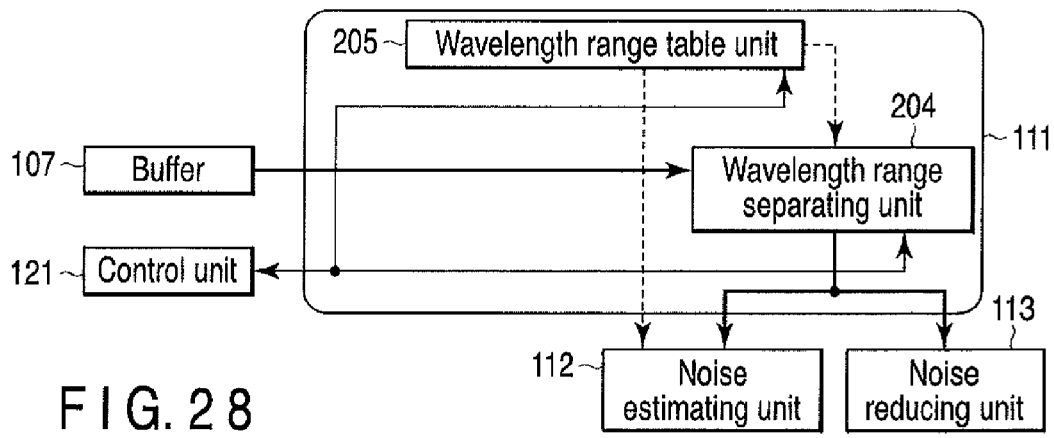
F I G. 28
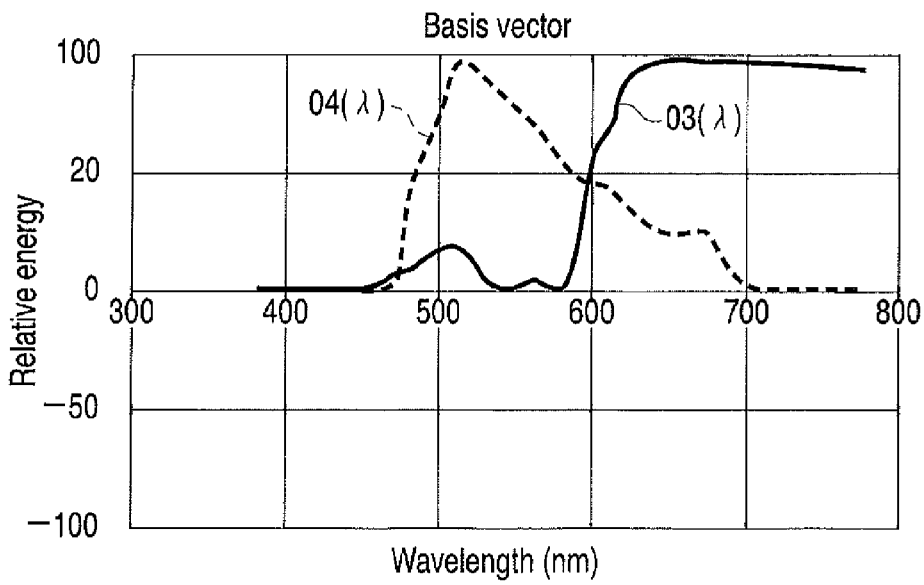
F I G. 29

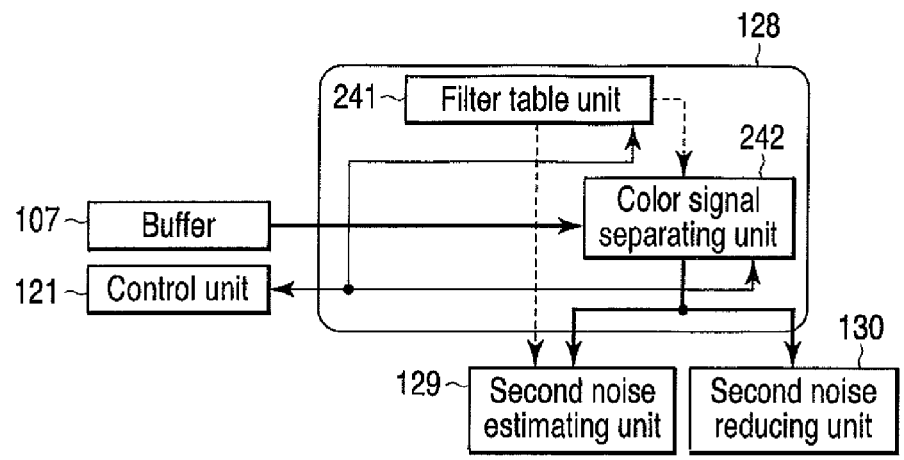
F I G. 3 4
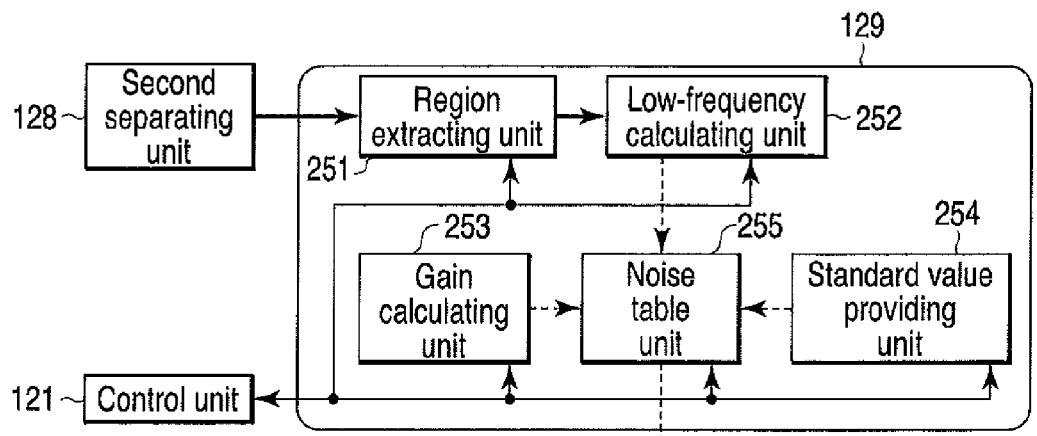
F I G. 3 5
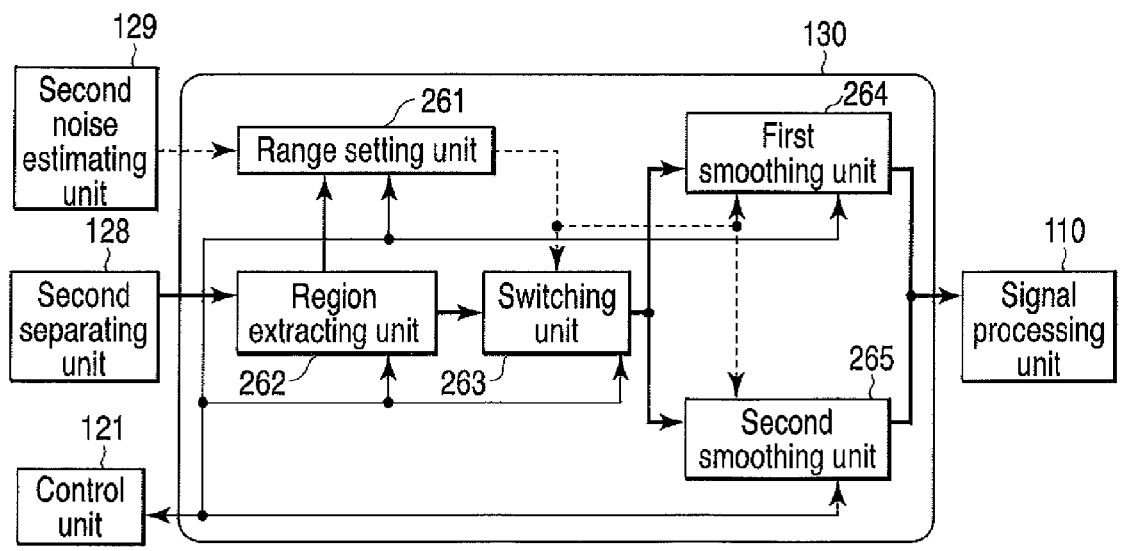
F I G. 3 8

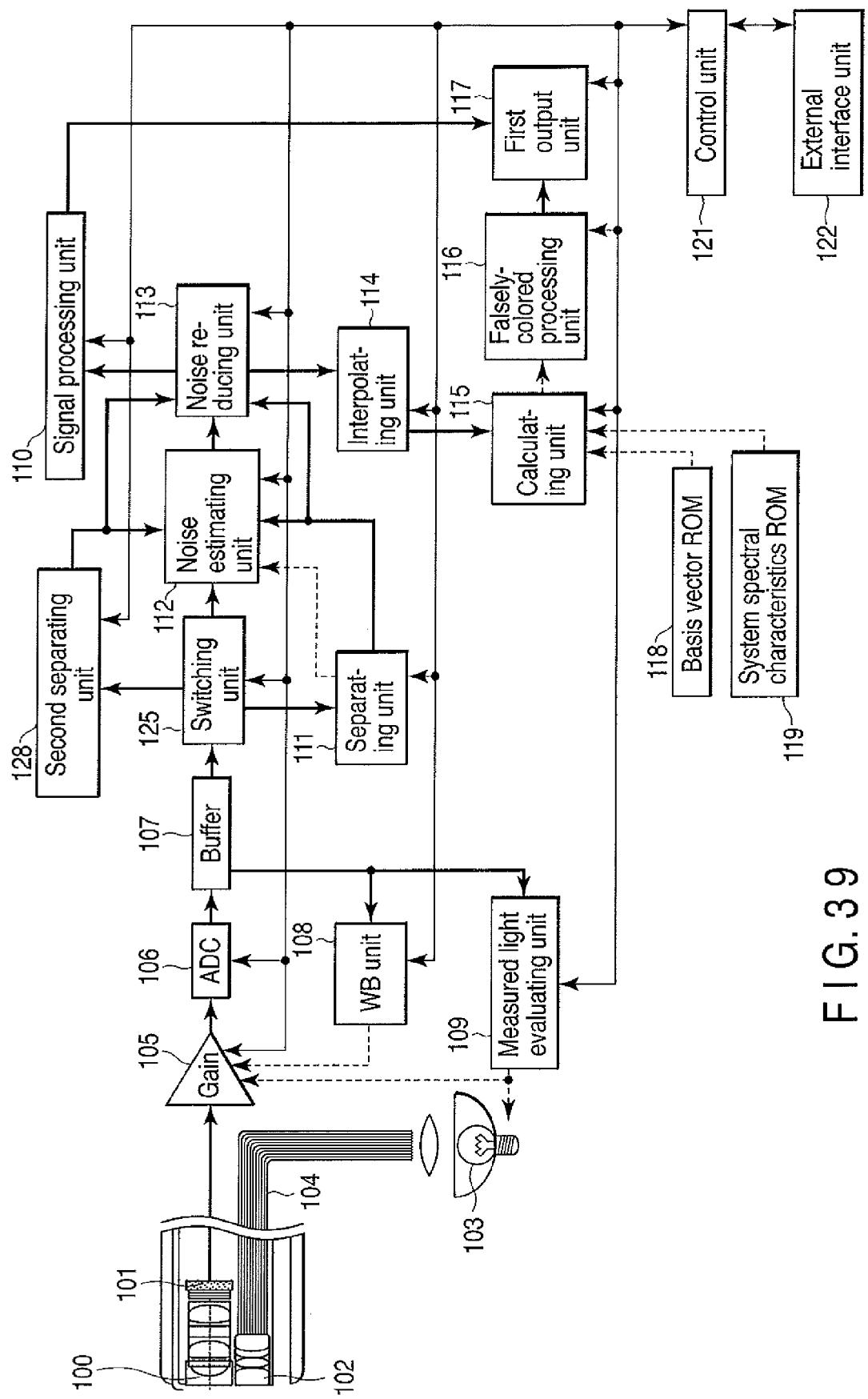
F I G. 39

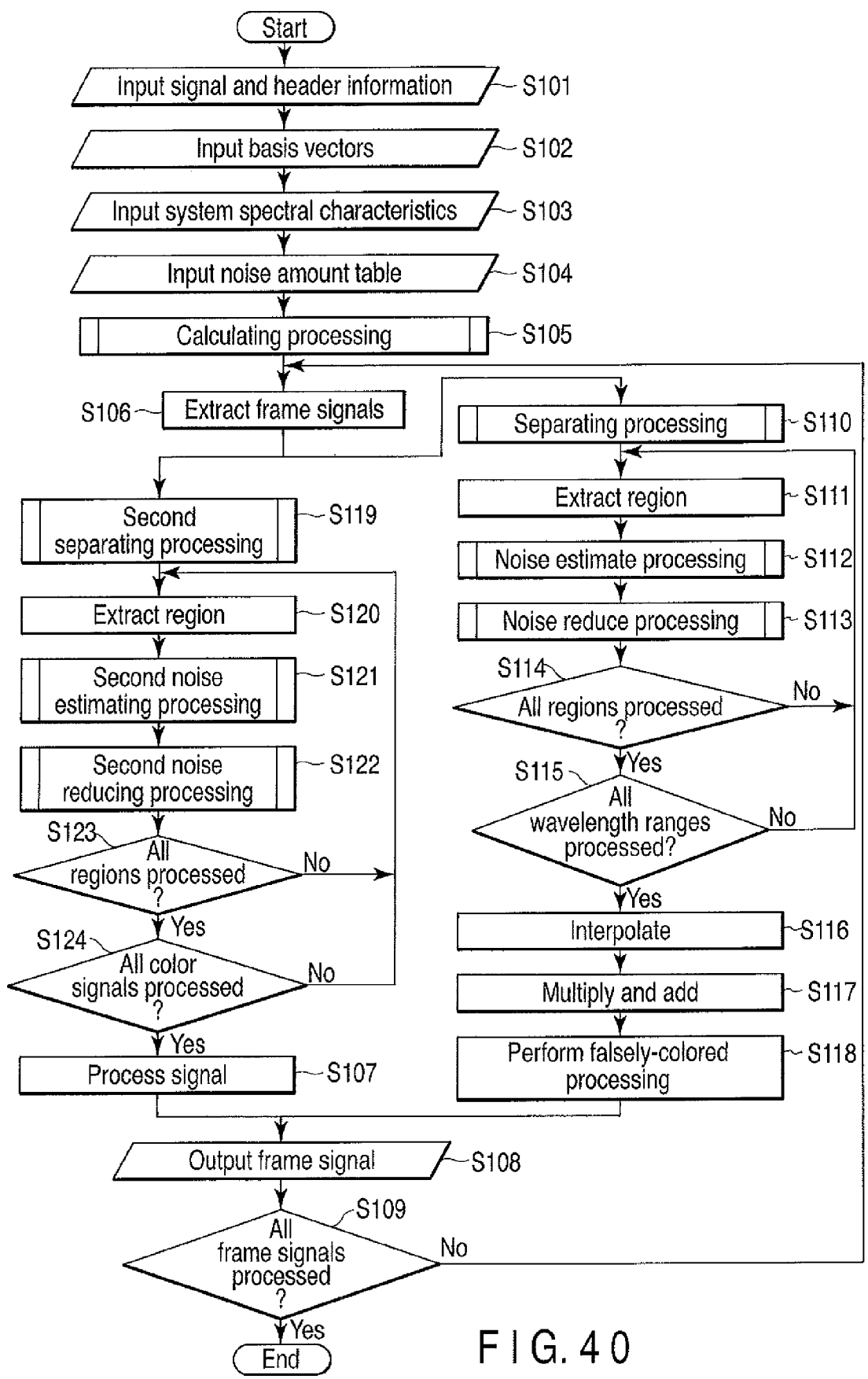
F I G. 40

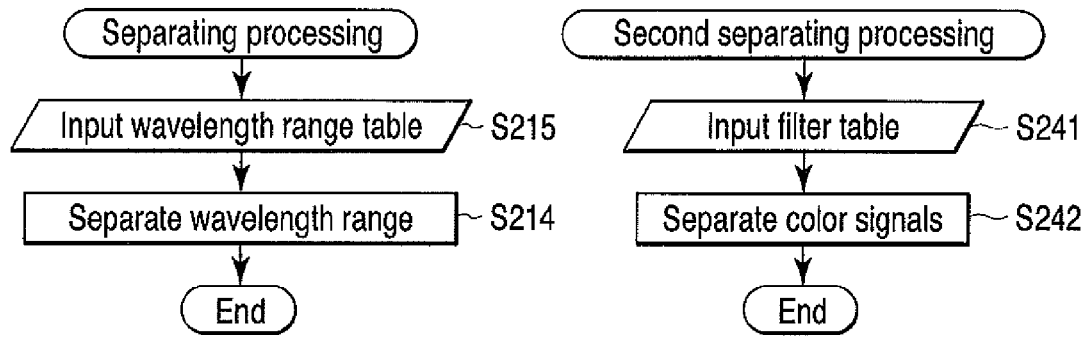
F I G. 4 1     F I G. 4 2
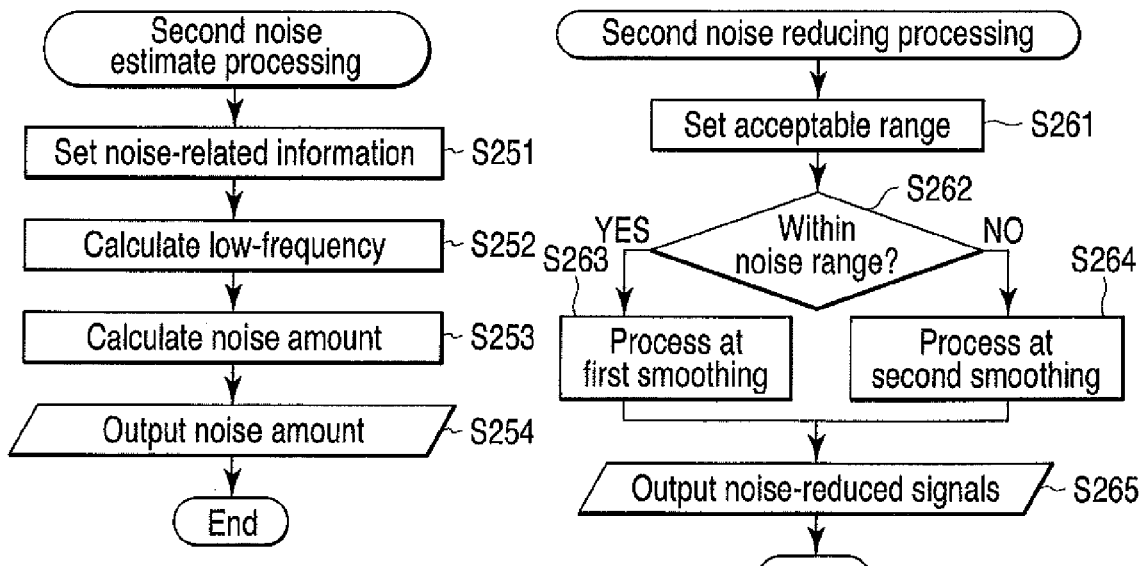
F I G. 4 3     F I G. 4 4

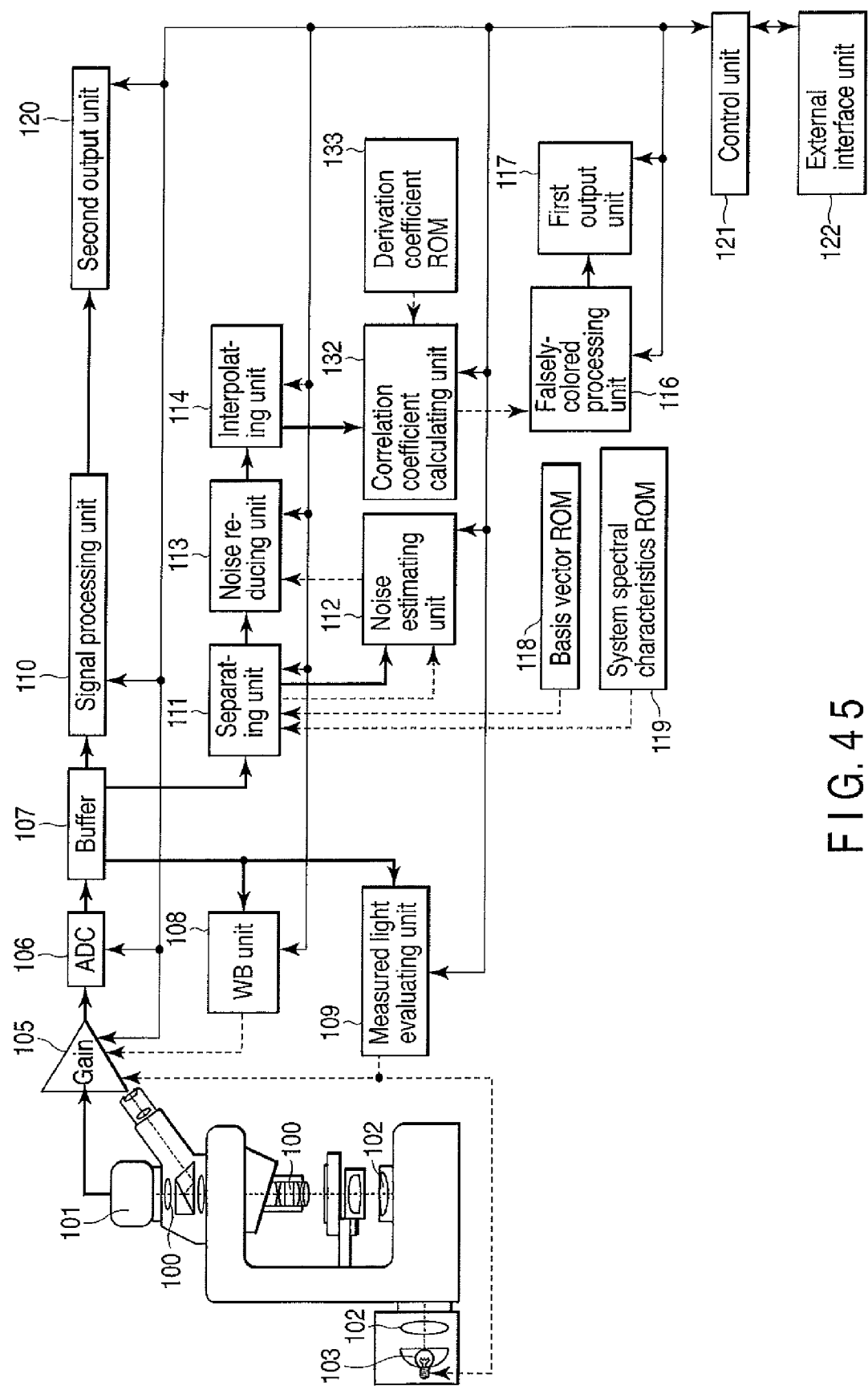
F I G. 45

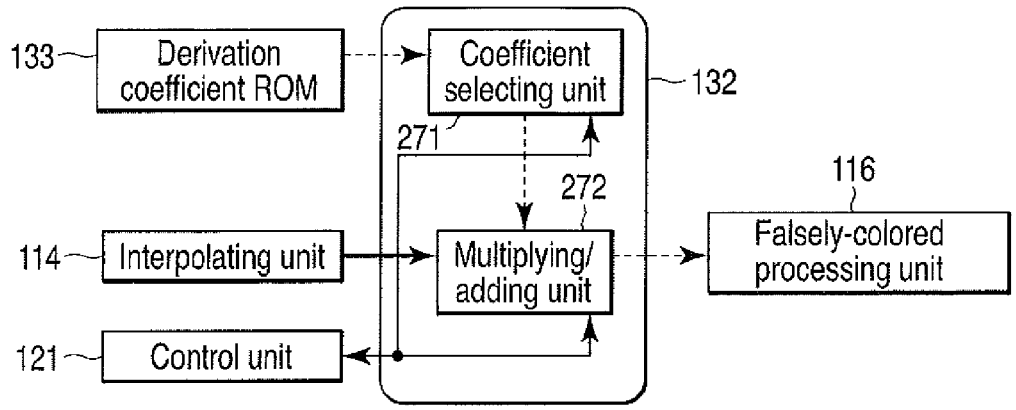
F I G. 46
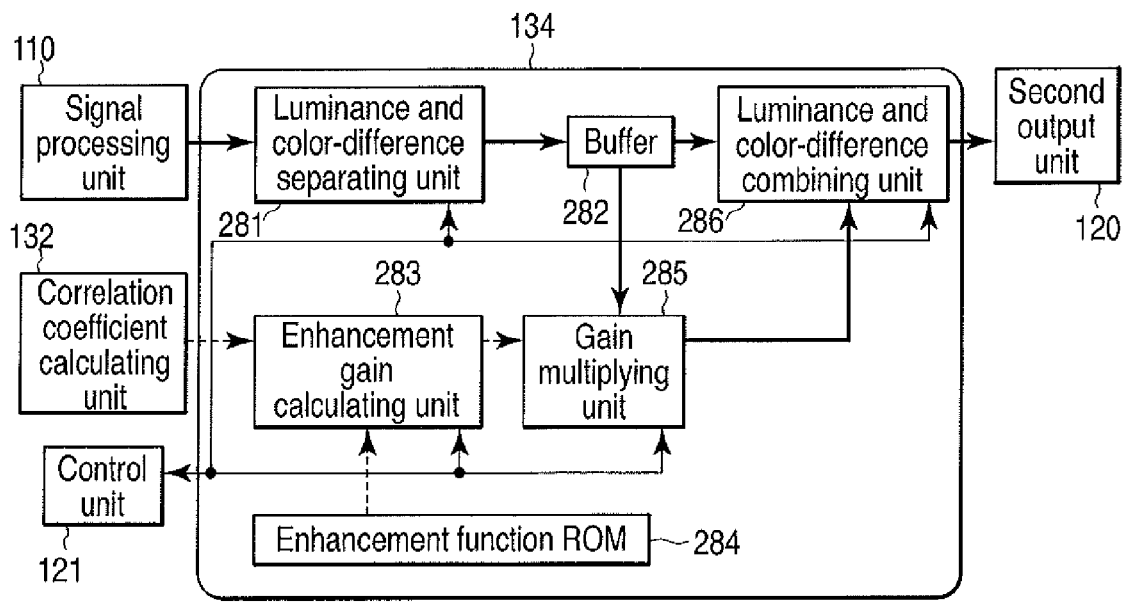
F I G. 48
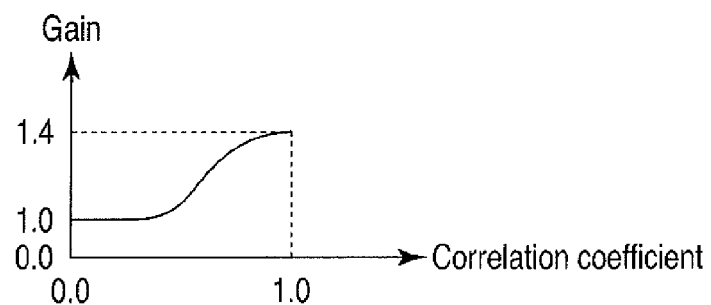
F I G. 49

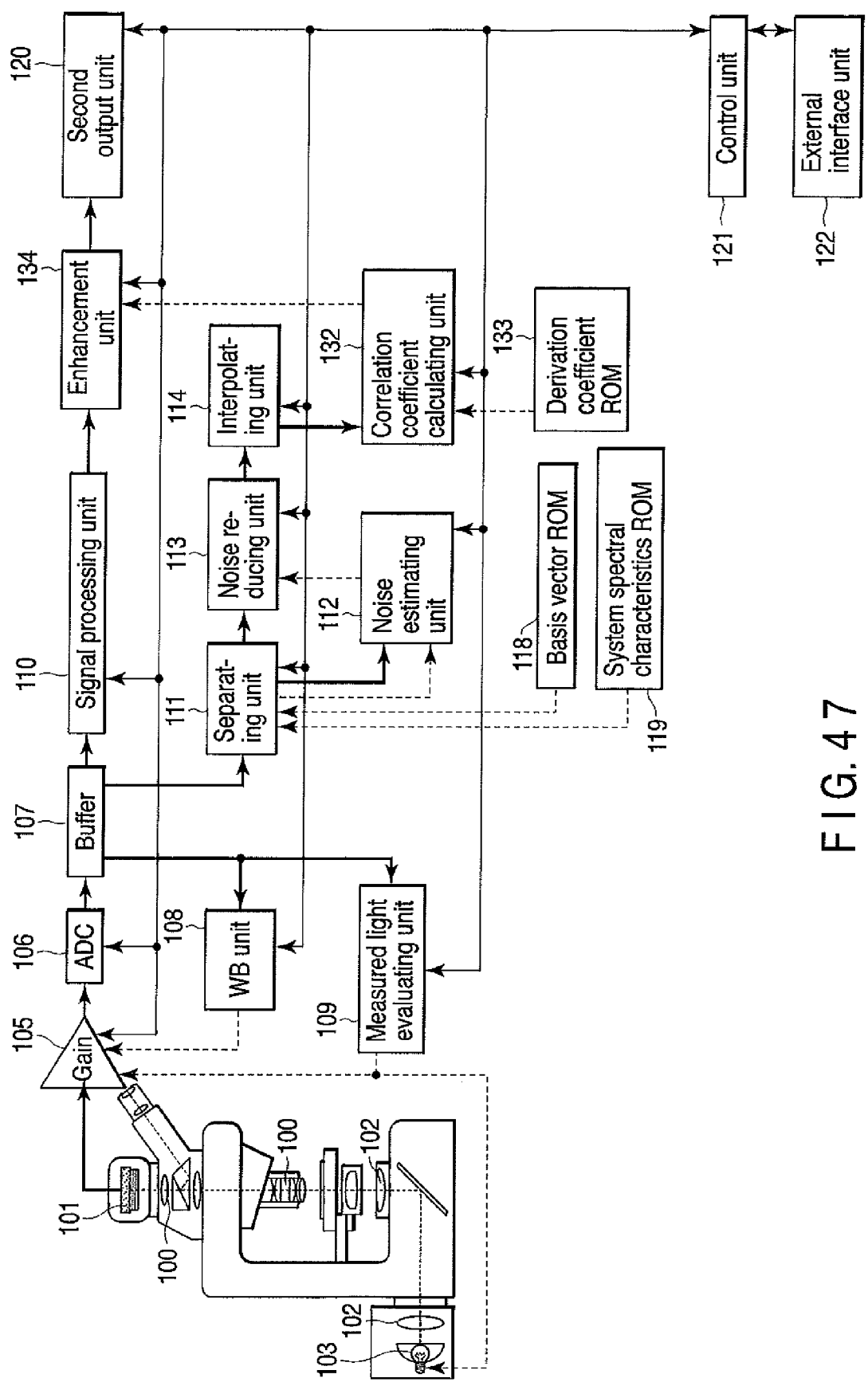
F I G. 47

DISCRIMINATION APPARATUS, DISCRIMINATION METHOD AND PROGRAM RECORDING MEDIUM

CROSS-REFERENCE TO RELATED APPLICATIONS

This application is based upon and claims the benefit of priority from prior Japanese Patent Application No. 2008-306464, filed Dec. 1, 2008, the entire contents of which are incorporated herein by reference.

BACKGROUND OF THE INVENTION

1. Field of the Invention

The present invention relates to a discrimination apparatus and a discrimination method for discriminating a subject, and a program recording medium storing a program for causing a computer to perform procedures according to the discrimination method.

2. Description of the Related Art

Jpn. Pat. Appln. KOKAI Publication No. 2003-93336 discloses an example calculating image signals of a particular narrowband by performing signal processing with the use of broadband light as observation light. Through this processing, high-quality image signal of a narrowband with less noise can be obtained. A subject having the spectral characteristics of particular parts, such as blood vessels, is discriminated in accordance with the image signal, and the discrimination result is displayed on a display monitor. By doing so, observation of the subject to be discriminated becomes easier.

BRIEF SUMMARY OF THE INVENTION

According to a first aspect of the present invention, there is provided a discrimination apparatus, comprising:

a separating unit configured to separate kinds (N being a natural number of 2 or greater) of color signals forming an image signal obtained by image acquisition of a subject with a color imaging system into kinds (M being a natural number of 1 or greater, M≦N) of wavelength ranges, based on known spectral characteristics of a subject to be discriminated, at least one of the separated wavelength ranges including a plurality of color signals;

a noise estimating unit configured to estimate a noise amount in each predetermined unit area in each of the wavelength ranges separated by the separating unit;

a noise reducing unit configured to perform a noise reducing processing on each of the wavelength ranges separated by the separating unit, based on the noise amount estimated by the noise estimating unit; and a discriminating unit configured to perform a discriminating processing on the subject to be discriminated, based on the color signals in the wavelength ranges noise-reduced by the noise reducing unit.

According to a second aspect of the present invention, there is provided a discrimination method comprising:

acquiring an image signal formed with (N being a natural number of 2 or greater) color signals, the image signal being obtained by image acquisition of a subject with a color imaging system, the subject including a subject that has known spectral characteristics and is to be discriminated;

separating the kinds of color signals into M kinds (M being a natural number of 1 or greater, MN) of wavelength ranges, at least one of the separated wavelength ranges including a plurality of color signals;

estimating a noise amount in each predetermined unit area in each of the separated wavelength ranges;

performing a noise reducing processing on each of the separated wavelength ranges, based on the estimated noise amount; and performing a discriminating processing on the subject to be discriminated, based on the color signals in the noise-reduced wavelength ranges.

According to a third aspect of the present invention, there is provided a program recording medium storing a program for causing a computer to:

acquire an image signal formed with (N being a natural number of 2 or greater) color signals, the image signal being obtained by image acquisition of a subject with a color imaging system, the subject including a subject that has known spectral characteristics and is to be discriminated;

separate the kinds of color signals into kinds (M being a natural number of 1 or greater, M≦N) of wavelength ranges, at least one of the separated wavelength ranges including a plurality of color signals;

estimate a noise amount in each predetermined unit area in each of the separated wavelength ranges;

perform a noise reducing processing on each of the separated wavelength ranges, based on the estimated noise amount; and perform a discriminating processing on the subject to be discriminated, based on the color signals in the noise-reduced wavelength ranges.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 15 shows an example structure of the noise reducing unit;

FIG. 16 shows an example structure of the calculating unit;

FIG. 17 illustrates the structure of a discrimination apparatus in accordance with a modification of the first embodiment;

FIG. 18 illustrates the structure of a discrimination apparatus in accordance with another modification of the first embodiment;

FIG. 19 illustrates the structure of a discrimination apparatus in accordance with another modification of the first embodiment;

FIG. 20 is a flowchart of software processing to perform signal processing in accordance with another modification of the first embodiment;

FIG. 21 is a flowchart of the calculating processing;

FIG. 22 is a flowchart of the separating processing;

FIG. 23 is a flowchart of the noise estimating processing;

FIG. 24 is a flowchart of the noise reducing processing;

FIG. 26 illustrates the structure of a filter formed with four kinds of color filters;

FIG. 27 shows the spectral characteristics of each of the color filters of FIG. 26;

FIG. 28 shows an example structure of the separating unit;

FIG. 29 shows examples of basis vectors;

FIG. 34 shows an example structure of the second separating unit;

FIG. 35 shows an example structure of the second noise estimating unit;

FIG. 38 shows an example structure of the second noise reducing unit;

FIG. 39 illustrates the structure of an endoscope including a discrimination apparatus in accordance with a modification of the second embodiment;

FIG. 40 is a flowchart of software processing to perform signal processing in accordance with another modification of the second embodiment;

FIG. 41 is a flowchart of the separating processing;

FIG. 42 is a flowchart of the second separating processing;

FIG. 43 is a flowchart of the second noise estimating processing;

FIG. 44 is a flowchart of the second noise reducing processing;

FIG. 45 illustrates the structure of a microscope including a discrimination apparatus in accordance with a third embodiment of the present invention;

FIG. 46 shows an example structure of the correlation coefficient calculating unit;

FIG. 47 illustrates the structure of a microscope including a discrimination apparatus in accordance with a modification of the third embodiment;

FIG. 48 shows an example structure of the emphasizing unit;

FIG. 49 shows an example of a gain table for emphasis recorded on the emphasis function ROM;

DETAILED DESCRIPTION OF THE INVENTION

Figure 1:
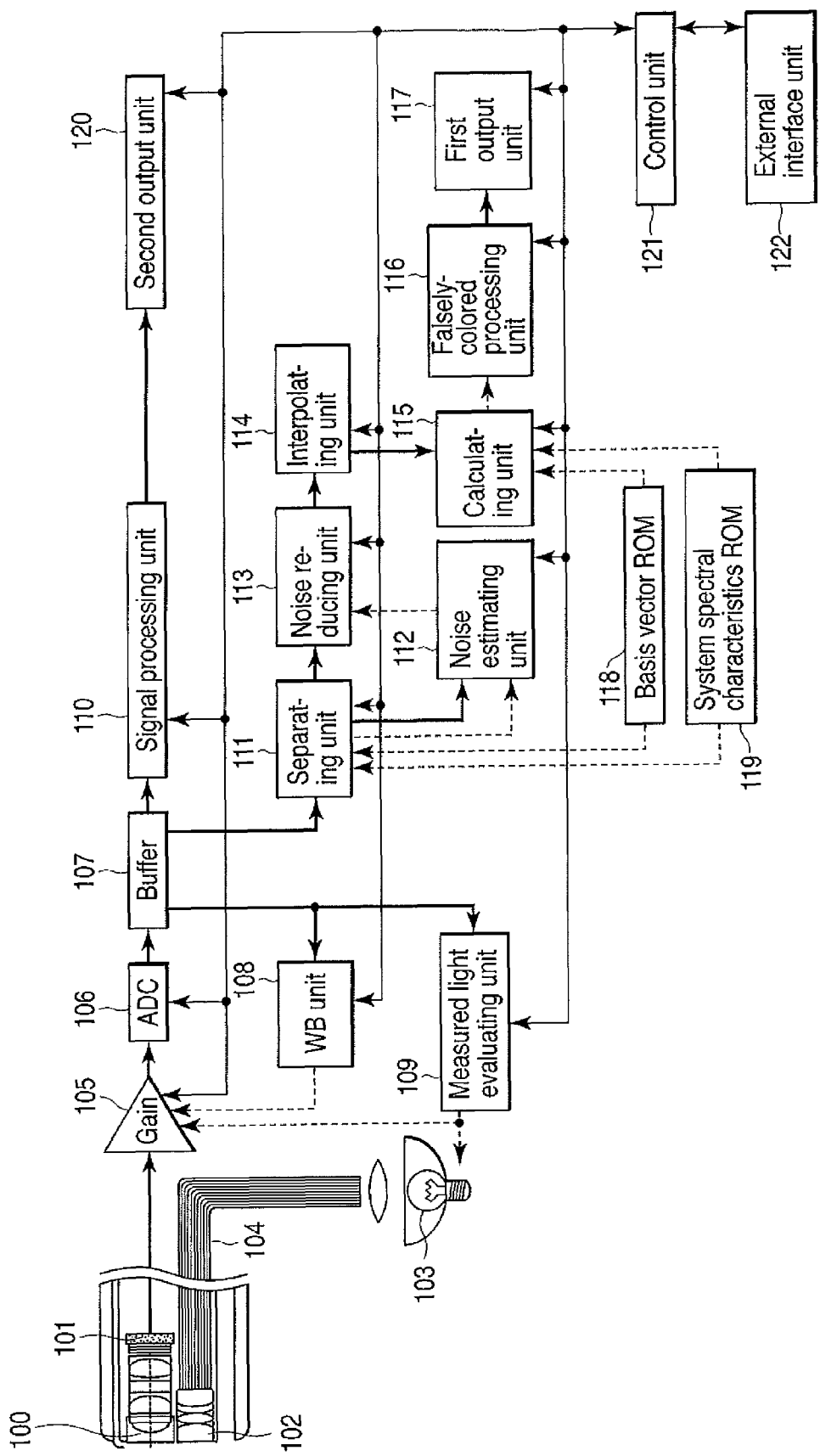
FIG. 1 illustrates the structure of an endoscope including a discrimination apparatus in accordance with a first embodiment of the present invention.

By referring to FIG. 1, the structure of an endoscope that includes a discrimination apparatus in accordance with a first embodiment of the present invention is described. In the drawing, the arrows with bold lines indicate the flows of image signals, the arrows with thin lines indicate the flows of control signals, and the arrows with dashed lines indicate the flows of other signals (the same applies to the other drawings).

A color imaging system including an imaging lens unit 100 and a CCD 101 is provided at the tip end of an endoscope to be inserted into a human body to be tested. An illuminating lens unit 102 is further provided at the tip end of the endoscope. An illuminating light source 103 is also provided at the rear end side of the endoscope. The illuminating light from the illuminating light source 103 is guided to the illuminating lens unit 102 via optical fibers 104 extending in the endoscope, and is emitted onto the subject (not shown) via the illuminating lens unit 102. The CCD 101 acquires image of the illuminated subject. A image signal obtained by this image acquisition processing is amplified at an amplifier unit (referred to as "Gain" in the drawing) 105, and is then converted into a digital signal at an ADC 106.

The digital image signal converted by the ADC 106 is buffered by a buffer 107, and is then transferred to a WB unit 108, a measured light evaluating unit 109, a signal processing unit 110, and a separating unit 111. The WB unit 108 is connected to the amplifier unit 105. The measured light evaluating unit 109 is connected to the illuminating light source 103 and the amplifier unit 105.

The separating unit 111 is connected to a noise estimating unit 112 and a noise reducing unit 113. The noise estimating unit 112 is connected to the noise reducing unit 113. The noise reducing unit 113 is connected to an interpolating unit 114, and the interpolating unit 114 is connected to a calculating unit 115. The calculating unit 115 is connected to a falsely-colored processing unit 116, and the falsely-colored processing unit 116 is connected to a first output unit 117 such as a liquid crystal display.

A basis vector ROM 118 and a system spectral characteristics ROM 119 are connected to the separating unit 111 and the calculating unit 115.

The signal processing unit 110 is connected to a second output unit 120 such as a liquid crystal display.

A control unit 121 is a microcomputer or the like. The control unit 121 is bidirectionally connected to the amplifier unit 105, the ADC 106, the WB unit 108, the measured light evaluating unit 109, the signal processing unit 110, the separating unit 111, the noise estimating unit 112, the noise reducing unit 113, the interpolating unit 114, the calculating unit 115, the falsely-colored processing unit 116, the first output unit 117, and the second output unit 120. An external interface unit 122 is also bidirectionally connected to the control unit 121. The external interface unit 122 includes a power switch, a shutter button, and an interface for setting various modes for image acquisition.

In the following, the signal flows shown in FIG. 1 are described. A user sets the image acquisition conditions including the subject to be discriminated as described later, the color imaging system, and the illuminating light, via the external interface unit 122. The user then presses the shutter button of the external interface unit 122, to put the endoscope into an image acquisition mode.

In the image acquisition mode, the image signals obtained at the CCD 101 are continuously output as an analog signal from the CCD 101 at predetermined time intervals. Hereinafter, the image signals that are continuously output will be referred to as a image signal, and one frame of the image signal will be referred to as the frame signal. In this embodiment, 1/30 second is assumed as the predetermined time interval (hereinafter referred to as one frame time).

Figure 2:
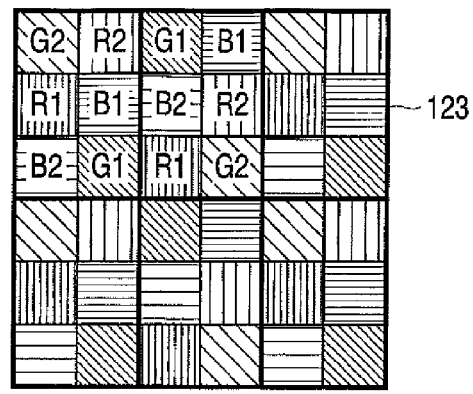
FIG. 2 illustrates the structure of a filter formed with six kinds of color filters.

The CCD 101 is a single CCD that has six kinds of color filters placed on the front face. FIG. 2 illustrates the structure of a filter 123 with the six kinds of color filters. This filter 123 has unit cells each 2×3 pixels. In this unit cell, the six kinds of color filters of blue-based filters (B1, B2), green-based filters (G1, G2), and red-based filters (R1, R2) are arranged pixel by pixel from the short wavelength side. In this case, two kinds of base units with different arrangement patterns of the six kinds of color filters are alternately arranged.

Figure 3:
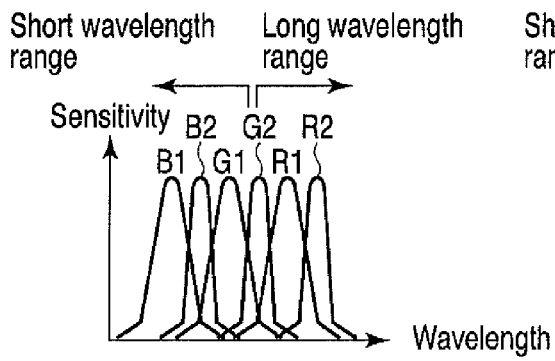
FIG. 3 shows an example of the spectral characteristics of each of the color filters of FIG. 2.

FIG. 3 shows the spectral characteristics of the six kinds of color filters. In this embodiment, with the resistance of the regular color image signal to noise being taken into consideration, R1, G1, and B1 are assumed to have broadband sensitivity characteristics equivalent to the color filters of blue, green and red, which are used in a Bayer-type single CCD. Those color filters are used for generating the later described regular color image signal. Meanwhile, R2, G2, and B2 have the characteristics of narrower bands than R1, G1, and B1, and are used along with R1, G1, and B1 in the later described signal processing with the use of a basis vector. By using this filter 123, the analog signals generated from the CCD 101 turn into image signal formed with six kinds of color signals. In this embodiment, color signals are generated by an image sensor formed with the CCD 101 and the filter 123 in the color imaging system.

Figure 4:
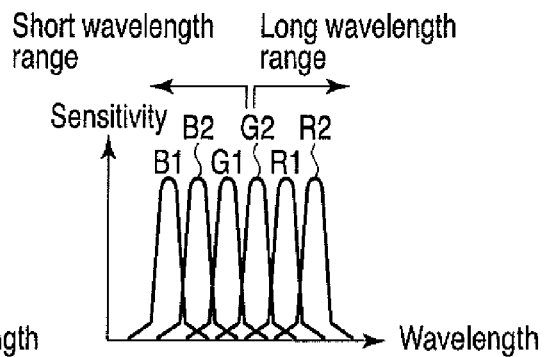
FIG. 4 shows another example of the spectral characteristics of each of the color filters of FIG. 2.

In the six kinds of color filters, the bands of the color filters of B1, G1, and R1 are not necessarily limited to be wider than the bands of the color filters of B2, G2, and R2, as shown in FIG. 3. For example, all the color filters may be of narrow bands, as shown in FIG. 4. In such a case, the resistance of regular color image signal to noise decreases, but the precision in the later described signal processing based on the basis vector can be increased.

The analog signals are amplified at the amplifier unit 105 by a predetermined amount, and are converted into digital signals at the ADC 106, then the digital signals are transferred to the buffer 107. The buffer 107 can record the signals of one frame, and older frame signals are overwritten sequentially, as the image acquisition progresses. The frame signal in the buffer 107 is intermittently transferred to the WB unit 108 and the measured light evaluating unit 109 at predetermined time intervals under the control of the control unit 121.

The WB unit 108 calculates a white balance coefficient by integrating signals of predetermined levels such as the intermediate level for each of the colors corresponding to the color filters of the above mentioned filter 123. The white balance coefficient is transferred to the amplifier unit 105, and is multiplied by gains that vary among the color signals, in order to perform a white balance adjustment. The measured light evaluating unit 109 controls the light quantity of the illuminating light source 103 to perform appropriate exposure, and the amplification factor of the amplifier unit 105.

Under the control of the control unit 121, the signal processing unit 110 reads a single frame signal formed with the three-color signals of R1, G1, and B1 from the buffer 107. Here, R1, G1, and B1 are set in a wider range than the spectral characteristics of the three-color signals of R2, G2, and B2, which are not used at the signal processing unit 110. The signal processing unit 110 performs known interpolating, gradation processing, and enhancement processing on the single frame signal formed with the three-color signals of R1, G1, and B1, to calculate a regular color image signal. The calculated regular color image signal is transferred to the second output unit 120, and the second output unit 120 displays the regular color image signal as the second output signal.

Under the control of the control unit 121, the separating unit 111 selects and separates the color signals corresponding to (M being a natural number of 1 or greater, $M \leq N$) kinds of frequency ranges from the single frame signal formed with (N being a natural number of 2 or greater) kinds of color signals recorded on the buffer 107. The separated color signals are used in signal processing with the use of the later described basis vector. In this embodiment, N is six, and M is two. Accordingly, the separating unit 111 separates the frame signal formed with the six kinds of color signals corresponding to the filter 123 shown in FIG. 2 into two, short wavelength range signals and long wavelength range signals, as the signals of frequency ranges to be used in the signal processing with the use of the basis vector, for example. In this case, each wavelength range includes a plurality of color signals. More specifically, the separating unit 111 separates the color signals of B1, B2, and G1 as the short wavelength range signals, and the color signals of G2, R1, and R2 as the long wavelength range signals respectively, and then transfers the separated signals to the noise estimating unit 112 and the noise reducing unit 113. In this manner, the separating unit 111 separates signals of the frequency ranges to be used in the signal processing with the use of the basis vector from the frame signal formed with several kinds of color signals recorded on the buffer 107, so that the image signal of each wavelength range is formed with color signals continuous in the wavelength direction when the color signals B1, B2, G1, G2, R1, and R2 are arranged in the wavelength direction based on the dominant wavelength in the spectral characteristics of those color signals.

The basis vector ROM 118 stores special basis vectors based on the known spectral characteristics of each of the subjects to be discriminated. The system spectral characteristics ROM 119 stores a plurality of the spectral characteristics with respect to each of color imaging systems, and a plurality of the spectral characteristics with respect to the illuminating light of each of the kinds used in image acquisition. In this embodiment, the spectral characteristics with respect to the color imaging system are the spectral sensitivity characteristics of the CCD 101 to which the spectral transmittance characteristics of the imaging lens unit 100 are additionally considered. The spectral characteristics with respect to illuminating light are the spectral luminance characteristics of the illuminating light source 103 to which the spectral transmittance characteristics of the optical fiber 104 for transfer and the illuminating lens unit 102 are additionally considered.

Under the control of the control unit 121, the noise estimating unit 112 estimates the amount of noise in each of the wavelengths ranges area separated by the separating unit 111 by the predetermined unit. Under the control of the control unit 121, the noise reducing unit 113 performs a noise reducing processing for each of the wavelengths separated by the separating unit 111, based on the amount of noise estimated by the noise estimating unit 112. Under the control of the control unit 121, the interpolating unit 114 reads the signal of each of the noise-reduced wavelength ranges from the noise reducing unit 113, and generates six kinds of frame signals formed with six kinds of color signals by performing a known interpolating processing. The generated six kinds of frame signals are sequentially transferred to the calculating unit 115 one by one. The calculating unit 115 and the falsely-colored processing unit 116 then perform processing in synchronization with each other for each frame signal, under the control of the control unit 121.

Under the control of the control unit 121 in accordance with the above image acquisition conditions set through the external interface unit 122, the calculating unit 115 reads the following information from the basis vector ROM 118 and the system spectral characteristics ROM 119. From the basis vector ROM 118, the calculating unit 115 reads the special basis vector based on the known spectral characteristics of a subject to be discriminated, and a basis vector based on a spectral characteristics of subject other than the subject to be discriminated. From the system spectral characteristics ROM 119, the calculating unit 115 reads the spectral characteristics of the imaging system, including the spectral characteristics with respect to one color imaging system to be used to acquire image of subjects including the subject to be discriminated, and the spectral characteristics with respect to the illuminating light to be used to image acquisition of the subject to be acquired by the color imaging system. After that, for the six kinds of frame signals formed with the six kinds of color signals B1, B2, G1, G2, R1, and R2 transferred from the interpolating unit 114, the calculating unit 115 calculates the weighting coefficients with respect to the special basis vectors, using the read special basis vectors, the spectral characteristics with respect to the color imaging system, and the spectral characteristics with respect to the illuminating light. The weighting coefficients of the special basis vectors are proportional to the existence of the subject to be discriminated, as will be described later. The weighting coefficients of the special basis vectors are transferred to the output signal calculating unit formed with the falsely-colored processing unit 116 and the first output unit 117. The falsely-colored processing unit 116 first normalizes the weighting coefficients transferred from the calculating unit 115, so that the weighting coefficients conform to the signal levels of the image signal. Since the weighting coefficients calculated by the calculating unit 115 have values of "0" to "1", the weighting coefficients are normalized to values between "0" and "255" if each signal level is represented by 8 bits. The falsely-colored processing unit 116 generates false color image signals by assigning different colors to the respective normalized weighting coefficients. In this embodiment, red is assigned to the weighting coefficients of B1, B2, and G1 in the short wavelength range, and cyan is assigned to the weighting coefficients of G2, R1, and R2 in the long wavelength range, respectively. The falsely-colored processing unit 116 transfers the false color image signals generated in this manner to the first output unit 117. The first output unit 117 in turn displays the false color image signals of the wavelength ranges independently of each other with respect to the subject to be discriminated. More specifically, the first output unit 117 displays output signal combined with the falsely-colored weighting coefficients of the short wavelength range and the falsely-colored weighting coefficients of the long wavelength range. Accordingly, the portion in which the subject to be discriminated exists only in the short wavelength range is displayed in red. The portion in which the subject to be discriminated exists only in the long wavelength range is displayed in cyan, the portion in which the subject to be discriminated exists in both the short wavelength range and the long wavelength range is displayed in white (red+cyan), and the portion in which the subject to be discriminated exists neither in the short wavelength range nor in the long wavelength range is displayed in black. In this manner, the output signal as the results of discrimination of the subject is output. The short wavelength range represents the information about the surface layer of the subject, and the long wavelength range represents the information about the deep layer of the object, respectively. The first output unit 117 and the second output unit 120 are not limited to liquid crystal displays, and may be other recording media such as hard disks or memory cards on which frame signals are sequentially recorded and stored.

As described above, the calculating unit 115, the falsely-colored processing unit 116, the first output unit 117, the basis vector ROM 118, and the system spectral characteristics ROM 119 function as the discriminating unit that performs a discriminating processing on a subject to be discriminated, based on the color signals in wavelength ranges on which a noise reducing processing has been performed by the noise reducing unit 113.

Figure 5:
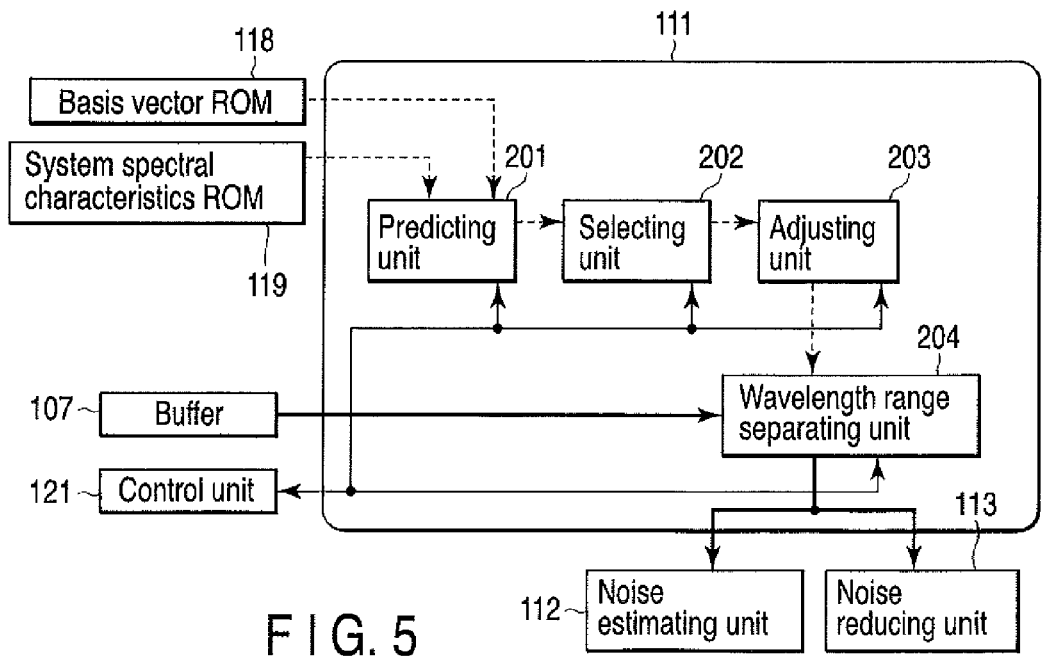
FIG. 5 illustrates an example structure of the separating unit.

The separating unit 111 includes a predicting unit 201, a selecting unit 202, an adjusting unit 203, and a wavelength range separating unit 204, as shown in FIG. 5. The basis vector ROM 118 and the system spectral characteristics ROM 119 are connected to the predicting unit 201. The predicting unit 201 is connected to the selecting unit 202. The selecting unit 202 is connected to the adjusting unit 203. The adjusting unit 203 is connected to the wavelength range separating unit 204. The wavelength range separating unit 204 is connected to the noise estimating unit 112 and the noise reducing unit 113. The buffer 107 is connected to the wavelength range separating unit 204. The control unit 121 is bidirectionally connected to the predicting unit 201, the selecting unit 202, the adjusting unit 203, and the wavelength range separating unit 204.

The predicting unit 201 receives the information about the subject to be discriminated of the above described image acquisition conditions set through the external interface unit 122, from the control unit 121. According to the information, the predicting unit 201 reads the special-purpose basis vector based on the known spectral characteristics of the subject to be discriminated, from the basis vector ROM 118.

Figure 6:
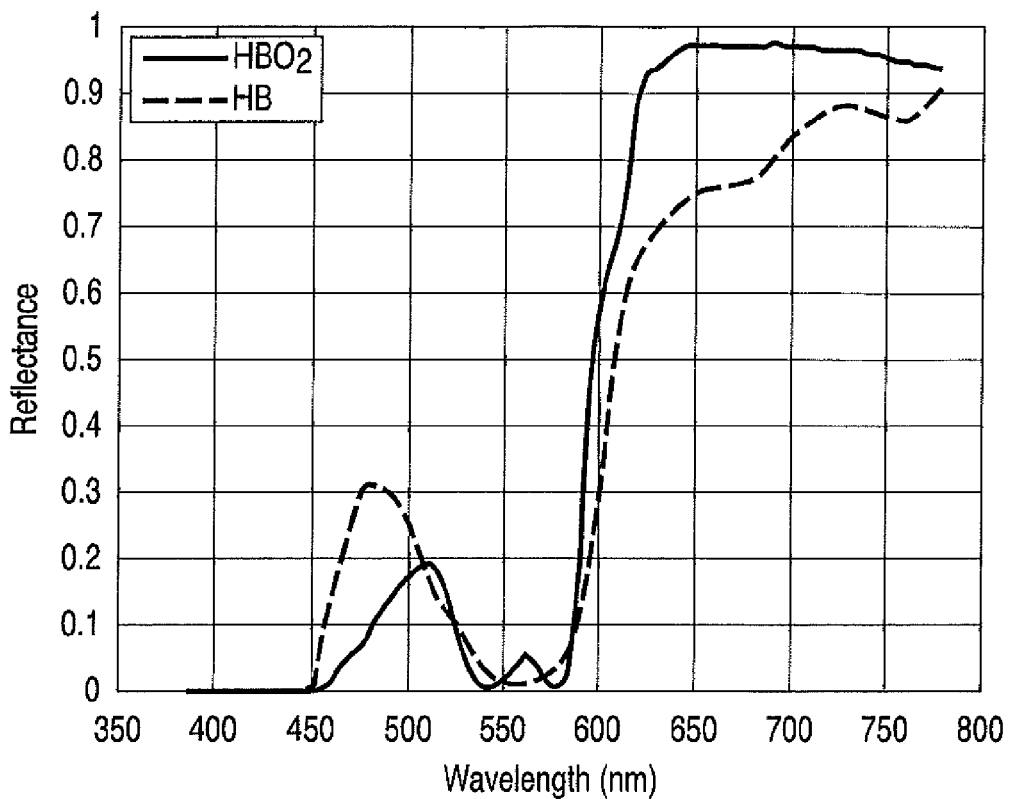
FIG. 6 shows the spectral reflectance characteristics of oxyhemoglobin and deoxyhemoglobin.

FIG. 6 shows the spectral reflectance characteristics of oxyhemoglobin ($HBO_2$) contained in large amounts in arteries, and the spectral reflectance characteristics of deoxyhemoglobin (HB) contained in large amounts in veins, the arteries and veins being blood vessels that are essential in diagnosis with an endoscope.

The special basis vectors of the subject to be discriminated, such as the basis vectors based on the spectral reflectance characteristics of oxyhemoglobin and deoxyhemoglobin, or the basis vectors based on the spectral luminance characteristics of auto-fluorescence of collagen as a main subject in fluorescent observation, or the like are stored in the basis vector ROM 118 in advance. If the subject to be discriminated is an artery, for example, the predicting unit 201 reads the special basis vector based on the spectral reflectance characteristics of oxyhemoglobin.

Figure 7:
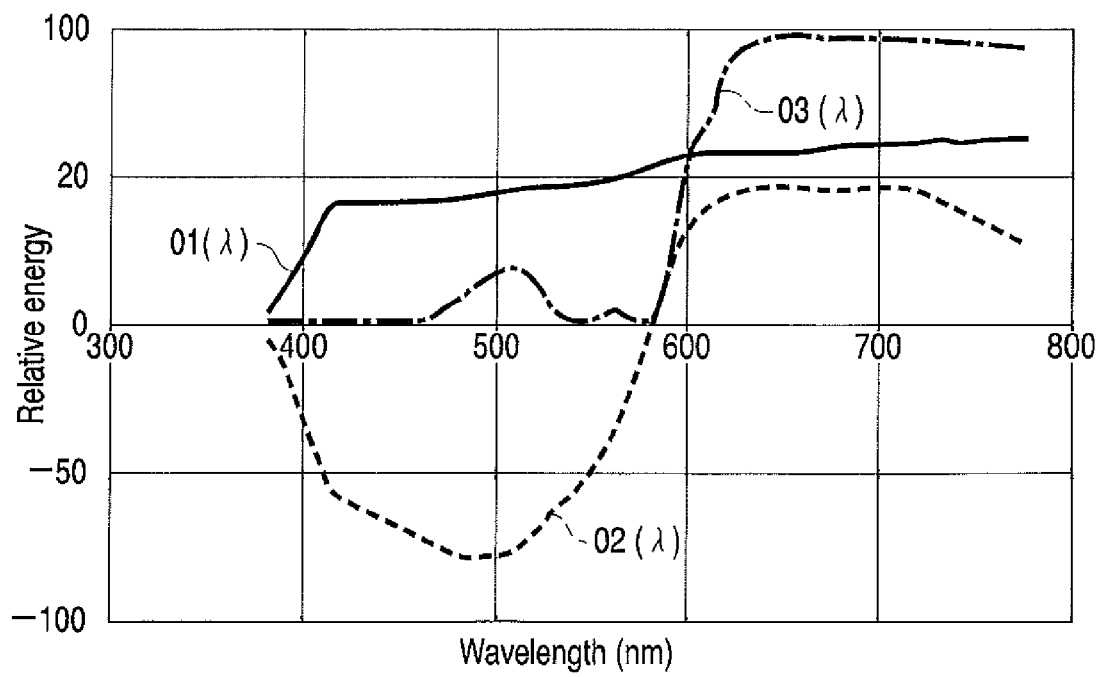
FIG. 7 shows examples of basis vectors.

FIG. 7 shows examples of basis vectors stored beforehand in the basis vector ROM 118. The examples of the basis vectors are the basis vectors (O1($\lambda$) and O2($\lambda$)) of two subjects not to be discriminated, and the special basis vector (O3($\lambda$)) of one subject (oxyhemoglobin in this example) to be discriminated. The basis vector ROM 118 may store only the special-purpose basis vectors of the subjects to be discriminated, or may store both the special-purpose basis vectors of the subjects to be discriminated and the basis vectors of subjects not to be discriminated, as shown in FIG. 7. The basis vectors of the subjects not to be discriminated may be upper basis vectors with higher contribution ratios selected by the principal component analysis for the spectral reflectance characteristics of the Munsell color chart or the like.

The predicting unit 201 further receives the information about the color imaging system and illuminating light of the above described image acquisition conditions set through the external interface unit 122, from the control unit 121. According to the information, the predicting unit 201 reads the spectral characteristics of the imaging system, including the spectral characteristics with respect to the color imaging system to be used to capture an image of the subject and the spectral characteristics with respect to the illuminating light to be used to capture an image of the subject with the color imaging system, from the system spectral characteristics ROM 119.

Figure 8:
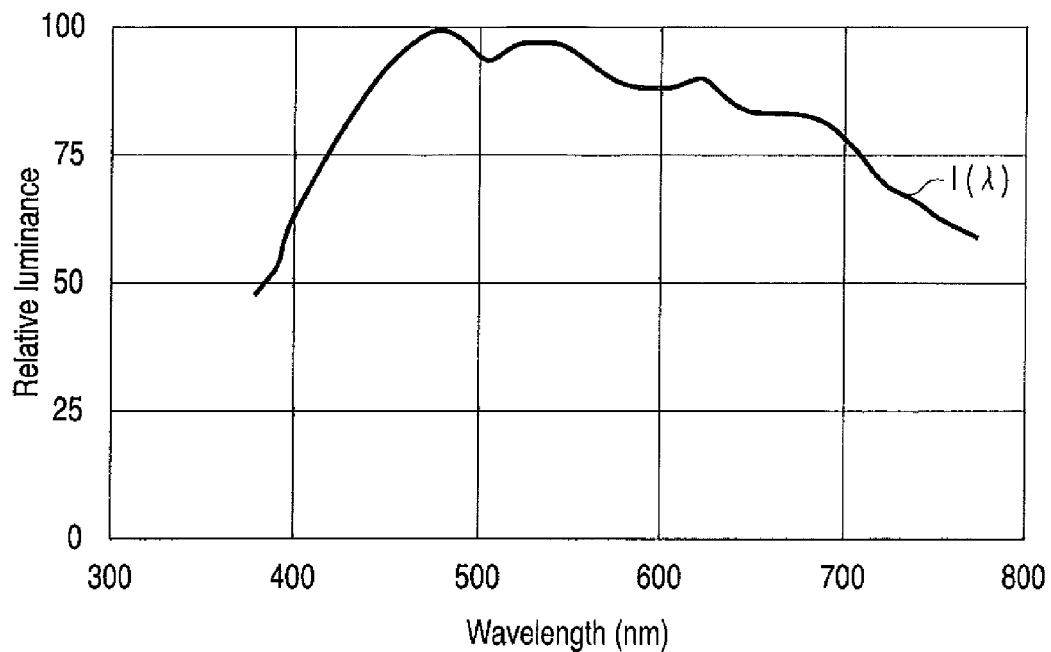
FIG. 8 shows the spectral luminance characteristics of the light source.
Figure 9:
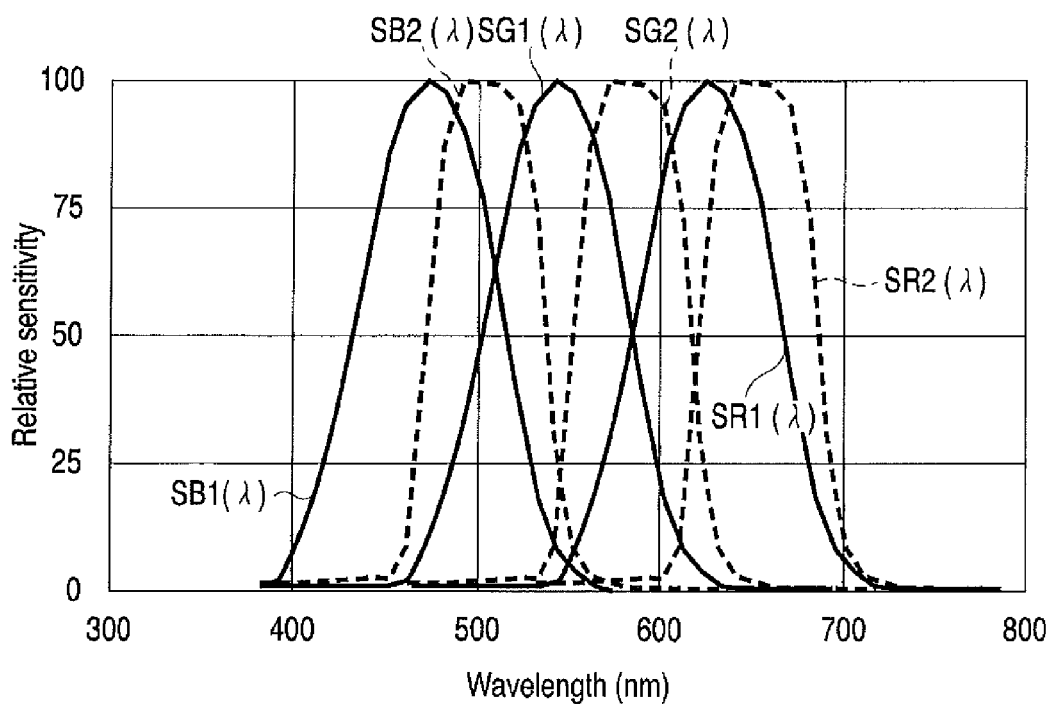
FIG. 9 shows the spectral sensitivity characteristics of the color imaging system.

FIG. 8 shows the spectral luminance characteristics (I($\lambda$)) of the light source as the spectral characteristics about the illuminating light to be used to capture an image of the subject. Here, the characteristics of a xenon light source are shown as an example. FIG. 9 shows the spectral sensitivity characteristics (SB1($\lambda$), SB2($\lambda$), SG1($\lambda$), SG2($\lambda$), SR1($\lambda$), and SR2($\lambda$)) of the color imaging system formed with the six color filters of B1, B2, G1, G2, R1, and R2, as the spectral characteristics about the color imaging system.

The predicting unit 201 predicts the output value of each color signal, based on the special basis vector that is read from the basis vector ROM 118 and is based on the known spectral characteristics of the subject to be discriminated, and the spectral characteristics of the imaging system that are read from the system spectral characteristics ROM 119 and are based on the spectral characteristics about the color imaging system to be used to capture image of subjects including the subject to be discriminated and the spectral characteristics about the illuminating light to be used to capture image of the subjects with the color imaging system.

Under the control of the control unit 121, the selecting unit 202 selects the color signals having output values similar to the output values of the respective color signals predicted by the predicting unit 201. For example, by a known clustering technique, the selecting unit 202 determines color signals having similar signal values to one another, or being in a predetermined range, and puts those color signals into the same group.

Under the control of the control unit 121, the adjusting unit 203 adjusts the number of groups of color signals selected by the selecting unit 202, so as to determine M kinds (two kinds in this embodiment) of wavelength ranges. Accordingly, when M+1 or more kinds are selected by the selecting unit 202, the two signals most similar to each other are forcibly combined so as to perform processing on M kinds of color signals. In this manner, the number of kinds of color signals is adjusted to M or less.

Under the control of the control unit 121, the wavelength range separating unit 204 selects the color signals corresponding to the M kinds of frequency ranges from the single frame signal formed with N kinds of color signals recorded on the buffer 107, based on the wavelength range determined by the adjusting unit 203. The wavelength range separating unit 204 then outputs the selected color signals to the noise estimating unit 112 and the noise reducing unit 113.

For example, there is a case where the filter 123 formed with the six kinds of color filters of B1, B2, G1, G2, R1, and R2 as shown in FIG. 2 is used to discriminate oxyhemoglobin and deoxyhemoglobin as subjects having the spectral reflectance characteristics shown in FIG. 6. In this case, the wavelength range separating unit 204 selectively reads B1, B2, and G1 or selectively reads G2, R1, and R2 from the single frame signal formed with the six kinds of color signals recorded on the buffer 107. The wavelength range separating unit 204 then separates the frame signal into the color signals corresponding to the M kinds of frequency ranges (two in this embodiment).

The color signals corresponding to the M kinds of frequency ranges (two kinds in this embodiment) separated in this manner are transmitted to the noise estimating unit 112 and the noise reducing unit 113. The noise estimating unit 112 and the noise reducing unit 113 are configured to perform the noise reducing processing disclosed by the inventor in US Patent Application Publication No. 2006/00667736 A1.

In the following, the noise reducing processing is described in detail.

Figure 10:
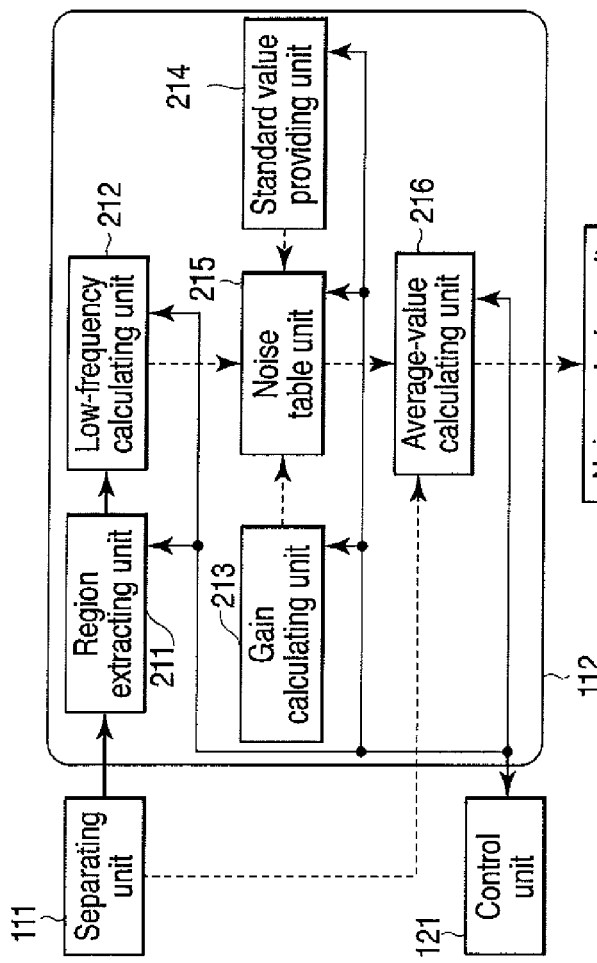
FIG. 10 shows an example structure of the noise estimating unit.

As shown in FIG. 10, the noise estimating unit 112 includes a region extracting unit 211, a low-frequency calculating unit 212, a gain calculating unit 213, a standard value providing unit 214, a noise table unit 215, and an average-value calculating unit 216. The separating unit 111 is connected to the region extracting unit 211 and the average-value calculating unit 216. The region extracting unit 211 is connected to the low-frequency calculating unit 212. The low-frequency calculating unit 212, the gain calculating unit 213, and the standard value providing unit 214 are connected to the noise table unit 215. The noise table unit 215 is connected to the average-value calculating unit 216. The average-value calculating unit 216 is connected to the noise reducing unit 113. The control unit 121 is bidirectionally connected to the region extracting unit 211, the low-frequency calculating unit 212, the gain calculating unit 213, the standard value providing unit 214, the noise table unit 215, and the average-value calculating unit 216.

In a conventional noise reducing processing using a Bayer-type single CCD, a single frame signal formed with three kinds of color signals is separated into the respective color signals, and a processing for each color is performed independently of the colors. In this case, unit blocks each consisting of 10×10 pixels containing target pixel blocks formed with target pixel of each color signal are sequentially extracted from the single frame signal, and 5×5 pixels with respect to the target pixel for each color signal is separated as a sub block. Smoothing is then performed on each sub block.

If this method of separating the color signals from one another is used in a case where the filter 123 formed with the six kinds of color filters of B1, B2, G1, G2, R1, and R2 as shown in FIG. 2, 10×15 pixels are to be extracted as a unit block. As a result, the pixel spacing among the color signals widens, and the homogeneity in each separated sub block of 5×5 pixels is degraded. This leads to performance deterioration in the noise reducing processing.

In this embodiment, on the other hand, frame signal is not separated into color signals, but N kinds of color signals are separated into M kinds of wavelength ranges in accordance with the known spectral characteristics of the subject to be discriminated. Here, at least one of M kinds of wavelength ranges contain a plurality of color signals. For example, where the subject to be discriminated is oxyhemoglobin and deoxyhemoglobin, the six kinds of color signals are separated into the two kinds of wavelength ranges: B1, B2, and G1 in the short wavelength range, and G2, R1, and R2 in the long wavelength range.

Under the control of the control unit 121, the region extracting unit 211 of the noise estimating unit 112 extracts a pixel region that includes the target pixel group to be subjected to a noise reduction, from the wavelength range separated in this manner by the separating unit 111. Under the control of the control unit 121, the region extracting unit 211 further extracts the color pixel regions that include the target pixels of the respective color signals from the extracted pixel region. For example, as indicated by the bold-line frames in FIG. 11, the three pixels of G2, R1, and R2, or the three pixels of B1, B2, and G1 are regarded as the target pixel group 124, and a unit block of 8×7 pixels is set as the basic block for noise reduction. The region extracting unit 211 extracts 4×7 pixels as a sub block including a target pixel group 124 in each wavelength range, as shown in FIG. 12. This sub block is the pixel region of a predetermined unit area that includes the target pixel group formed with the target pixel of each color signal to be subjected to a noise reduction. Further, the region extracting unit 211 extracts a region for each color signal by selecting only G2 in one pixel region and only R1 in another pixel region, for example. This region is the color pixel region that includes the target pixel of each color signal.

Under the control of the control unit 121, the low-frequency calculating unit 212 calculates the low-frequency component from each color pixel region extracted by the region extracting unit 211.

The gain calculating unit 213 calculates the information about the gain value of image signal at the amplifier unit 105, based on the information about ISO sensitivity and exposure conditions transferred from the control unit 121. The control unit 121 also obtains the information about the temperature value related to the color imaging system, using a temperature sensor (not shown) or the like. Accordingly, the gain calculating unit 213 and the control unit 212 function as a collecting unit that collects the information about the gain value and temperature value.

Under the control of the control unit 121, the standard value providing unit 214 functions as a provider unit that provides a standard value about information that is not obtained by the collecting unit.

Under the control of the control unit 121, the noise table unit 215 outputs the noise amount $N_c$ (the suffix "c" indicating the type of signal) of each color signal in the color pixel regions, with the inputs being the information supplied from the collecting unit or the standard value providing unit 214 and the low-frequency components of the color pixel regions calculated by the low-frequency calculating unit 212. The noise table unit 215 is a lookup table that stores the relationships among the gain, temperature, signal value level, and noise amount. This lookup table is constructed by the technique disclosed in US Patent Application Publication No. 2006/0066736 A1.

The average-value calculating unit 216 calculates the average value of the noise amounts $N_c$ of the respective color signals calculated by the noise table unit 215, as the noise amount of the entire color pixel region of each color signal. The average-value calculating unit 216 then assigns the calculated average value as the uniform noise amount $N_b$ (the suffix "b" indicating the type of wavelength range) to the three target pixels constituting the target pixel group 124 included in the pixel region, such as the three pixels of B1, B2, and G1 surrounded by the bold-line frames in FIG. 11. The average-value calculating unit 216 also calculates the average value of the low-frequency components of each color signal from the low-frequency calculating unit 212, as the average value $AV_b$ of the pixels in the pixel region.

In this manner, the noise amount in each wavelength range separated by the separating unit 111 is estimated for each pixel region of the predetermined unit area. The estimated noise amount $N_b$ is then output along with the average value $AV_b$ of the pixels in the pixel region to the noise reducing unit 113 for each wavelength range.

In the noise amount calculation, there is no need to determine the information such as the temperature t and the gain g for each image acquisition. Desired information may be recorded in the standard value providing unit 214 in advance, and the calculation may be skipped. In this manner, higher-speed operations and power saving can be realized.

Figure 11:
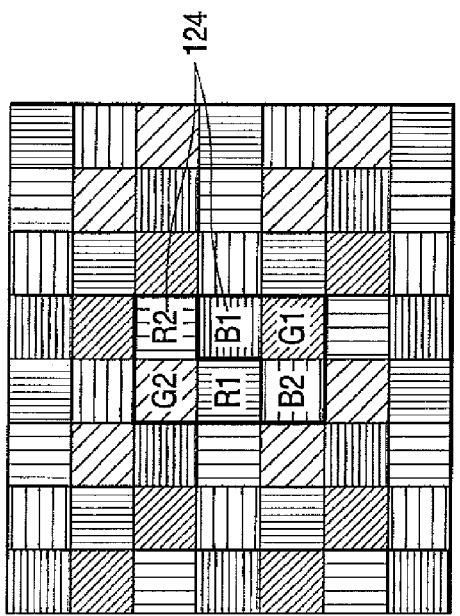
FIG. 11 shows an example of a unit block as the basic block in a noise reduction.
Figure 12:
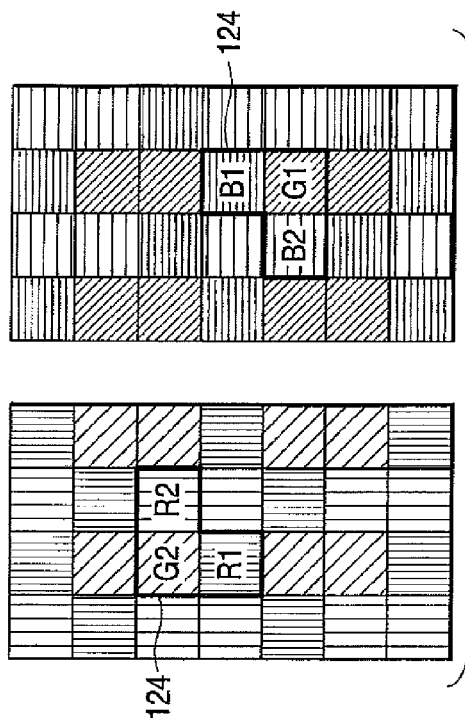
FIG. 12 shows examples of pixel regions each having a predetermined unit area including a target pixel group.

In this embodiment, the unit block to be the basic block in a noise reducing processing is extracted as an 8×7 pixel region, with the target pixel groups 124 being located in the middle, as shown in FIG. 11. The region extracting unit 211 extracts 4×7 pixel regions, each including the target pixel group 124, as the pixel regions each having the predetermined unit area for each wavelength range, as shown in FIG. 12. However, the present invention is not limited to this arrangement, and any size and shape may be set for pixel regions.

Figure 13:
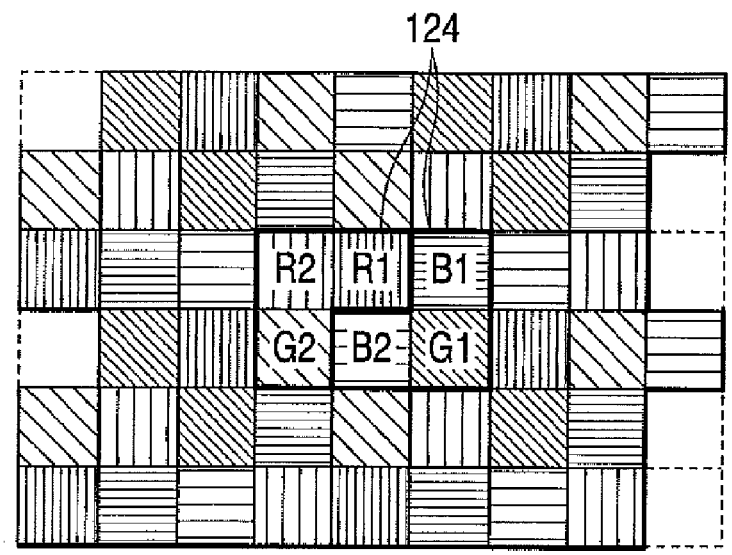
FIG. 13 shows another example of a unit block as the basic block in a noise reduction.
Figure 14:
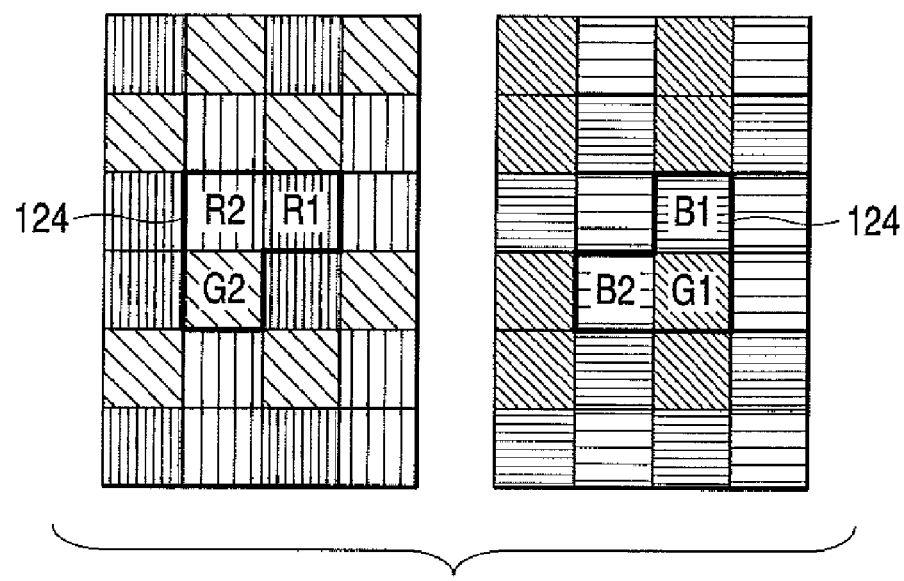
FIG. 14 shows other examples of pixel regions each having a predetermined unit area including a target pixel group.

For example, a 9×6 pixel region having target pixel groups 124 in the middle as shown in FIG. 13 may be extracted as the unit block, and 4×6 pixel regions each including a target pixel group 124 as shown in FIG. 14 may be extracted as pixel regions.

Also, the noise amount may not be extracted from the color pixel region of each color signal extracted from the pixel regions of the predetermined unit area. Instead, the noise amount may be extracted from each pixel region. In the noise estimating unit 112 in such a case, the region extracting unit 211 extracts a pixel region of the predetermined unit area including the target pixel group 124 formed with the target pixels of the respective color signals to be subjected to a noise reduction, from each wavelength range separated by the separating unit 111. The low-frequency calculating unit 212 calculates the low-frequency component from the pixel region extracted by the region extracting unit 211. In this manner, the average value of the signal levels in the pixel region is calculated. The noise table unit 215 calculates the noise amount, with the inputs being the information supplied from the gain calculating unit 213 and the control unit 121 functioning as the collecting unit or the standard value providing unit 214 functioning as the provider unit, and the low-frequency component calculated by the low-frequency calculating unit 212. The noise amount is then assigned as the uniform noise amount $N_b$ to the three target pixels constituting the target pixel group 124 in the pixel region of the predetermined unit area. In this manner, the noise table unit 215 functions as a noise amount output unit that outputs the noise amount of the target pixel group 124, with the inputs being the information supplied from the collecting unit or the providing unit and the low-frequency components calculated by the low-frequency calculating unit. Accordingly, the average-value calculating unit 216 becomes unnecessary in this case.

As shown in FIG. 15, the noise reducing unit 113 includes a region extracting unit 221, a range setting unit 222, a switching unit 223, a first smoothing unit 224, and a second smoothing unit 225. The separating unit 111 is connected to the region extracting unit 221. The region extracting unit 221 is connected to the range setting unit 222 and the switching unit 223. The noise estimating unit 112 is connected to the range setting unit 222. The range setting unit 222 is connected to the switching unit 223, the first smoothing unit 224, and the second smoothing unit 225. The switching unit 223 is connected to the first smoothing unit 224 and the second smoothing unit 225. The first smoothing unit 224 and the second smoothing unit 225 are connected to the interpolating unit 114. The control unit 121 is bidirectionally connected to the region extracting unit 221, the range setting unit 222, the switching unit 223, the first smoothing unit 224, and the second smoothing unit 225.

Like the region extracting unit 211 of the noise estimating unit 112, the region extracting unit 221, under the control of the control unit 121, extracts a pixel region of a predetermined unit area including the target pixel group 124 formed with the target pixels of the respective color signals to be subjected to noise reduction, from the wavelength range separated by the separating unit 111.

Under the control of the control unit 121, the range setting unit 222 sets a noise range of the target pixel group 124, based on the noise amount $N_b$ estimated by the noise estimating unit 112. More specifically, under the control of the control unit 121, the range setting unit 222 reads the average value $AV_b$ and the noise amount $N_b$ of the pixels in the region extracted by the region extracting unit 211, from the noise estimating unit 112. After that, the range setting unit 222 sets the upper limit Noise_$Up_b$ and the lower limit Noise_$Low_b$ as the acceptable noise amount range, according to the following equations (1):

$$\text{Noise\_}Up_b = AV_b + N_b/2$$

$$\text{Noise\_}Low_b = AV_b - N_b/2 \qquad (1)$$

The noise range, namely, the acceptable range of Noise_$Up_b$ to Noise_$Low_b$ set in the above manner, is transferred to the switching unit 223. The range setting unit 222 further transfers the average value $AV_b$ and the noise amount $N_b$ read from the noise estimating unit 112 to the first smoothing unit 224 and the second smoothing unit 225.

Under the control of the control unit 121, the switching unit 223 reads the pixel values $P_c$ of the target values constituting the target pixel group 124 from the region extracting unit 221, or the pixel values $P_c$ of the three target pixels in the example illustrated in FIG. 11. The switching unit 223 then determines whether the pixel values $P_c$ fall within the acceptable range. The determination result is one of the following three: "within the noise range", "higher than the noise range", and "lower than the noise range". In the case of "within the noise range", the switching unit 223 transfers the pixel values $P_c$ of the target pixel group 124 to the first smoothing unit 224. In the other cases, the switching unit 223 transfers the pixel values $P_c$ of the target pixel group 124 to the second smoothing unit 225.

The first smoothing unit 224 performs smoothing on the values of all the pixels in the pixel region extracted by the region extracting unit 221, and sets the result as the value of the target pixel group 124. More specifically, the first smoothing unit 224 performs the smoothing processing to assign the average value $AV_b$ supplied from the range setting unit 222, to each of the pixel values $P_c$ of the target pixels constituting the target pixel group 124 supplied from the switching unit 223, as expressed by the following equation (2):

$$P_c = AV_b \qquad (2)$$

When the pixel values $P_c$ of the target pixel group 124 in the pixel region extracted by the region extracting unit 221 do not fall within the noise range set by the range setting unit 222, the second smoothing unit 225 performs a correcting processing. More specifically, the second smoothing unit 225 performs a correcting processing on the pixel values $P_c$ of the target pixel group 124 supplied from the switching unit 223, using the average value $AV_b$ and the noise value $N_b$ supplied from the range setting unit 222.

First, in the case of "higher than the noise range", a correcting processing is performed according to the following equation (3):

$$P_c = AV_b - N_b/2 \qquad (3)$$

In the case of "lower than the noise range", a correcting processing is performed according to the following equation (4):

$$P_c = AV_b + N_b/2 \qquad (4)$$

The processing result of the first smoothing unit 224 or the second smoothing unit 225 is transferred to the interpolating unit 114.

With the above described structures of the noise estimating unit 112 and the noise reducing unit 113, noise amount estimation can be performed in accordance with dynamically varying conditions such as the signal level, the temperature at the time of image capturing, and the gain. Also, an optimum noise reduction in the entire screen can be performed and high-quality signals can be obtained. Even if the above mentioned information is not obtained, noise amount estimation can be performed with the use of the standard value. Accordingly, a stable noise reducing effect can be achieved. Furthermore, by purposefully omitting a parameter calculation, an imaging system that requires lower costs and less power can be provided. Also, with the use of a lookup table in the noise amount calculation, high-speed noise amount estimation can be performed. Since the acceptable range is set according to noise amounts in a noise reducing processing, the original signals can be retained with high precision, and a noise reducing processing which discontinuity is prevented can be performed.

As shown in FIG. 16, the calculating unit 115 includes a data selecting unit 231, an integrating unit 232, a buffer 233, an inverse-matrix calculating unit 234, a buffer 235, a coefficient selecting unit 236, and a multiplying/adding unit 237. The basis vector ROM 118 and the system spectral characteristics ROM 119 are connected to the data selecting unit 231. The data selecting unit 231 is connected to the coefficient selecting unit 236 via the integrating unit 232, the buffer 233, the inverse-matrix calculating unit 234, and the buffer 235. The coefficient selecting unit 236 and the interpolating unit 114 are connected to the multiplying/adding unit 237. The multiplying/adding unit 237 is connected to the falsely-colored processing unit 116. The control unit 121 is bidirectionally connected to the data selecting unit 231, the integrating unit 232, the inverse-matrix calculating unit 234, the coefficient selecting unit 236, and the multiplying/adding unit 237.

The data selecting unit 231 receives the information about the subject to be discriminated of the image acquisition conditions set through the external interface unit 122, from the control unit 121. According to the information, the data selecting unit 231 reads the special basis vector based on the known spectral characteristics of the subject to be discriminated and the basis vectors based on the spectral characteristics of the subjects not to be discriminated, from the basis vector ROM 118. In this manner, the basis vector ROM 118 and the data selecting unit 231 function as a basis vector acquiring unit.

The special basis vectors of subjects to be discriminated and the basis vectors of subjects not to be discriminated are stored beforehand in the basis vector ROM 118. The special basis vectors of the subjects to be discriminated include basis vectors of arteries that are essential in diagnosis with an endoscope, such as basis vectors based on the spectral reflectance characteristics of oxyhemoglobin contained in the blood vessels and basis vectors based on the spectral reflectance characteristics of deoxyhemoglobin contained in large amounts in veins, or basis vectors based on the spectral luminance characteristics of auto-fluorescence of collagen as a main subject in fluorescent observation. In this embodiment, oxyhemoglobin is assumed as the subject to be discriminated. Accordingly, the data selecting unit 231 reads the basis vector based on the spectral reflectance characteristics of oxyhemoglobin as the basis vector of the subject to be discriminated. Upper basis vectors with higher contribution ratios selected by the principal component analysis for the spectral reflectance characteristics of the Munsell color chart or the like are stored as the basis vectors of subjects not to be discriminated. In this embodiment, a single CCD having the filter 123 formed with six kinds of color filters at the front face is used as the CCD 101, and three kinds of the color filters are respectively allocated both to the short wavelength range and the long wavelength range. Since the total number of basis vectors is three, the data selecting unit 231 reads the two basis vectors with higher contribution ratios as the basis vectors based on the spectral characteristics of subjects not to be discriminated.

In this case, the basis vector ROM 118 stores M basis vectors for each wavelength range in accordance with M kinds of wavelength ranges. For example, two basis vectors for the short wavelength range and the long wavelength range are stored in this embodiment. More specifically, the basis vectors ($O1(\lambda_s)$ and $O2(\lambda_s)$) of two subjects not to be discriminated, and the special basis vector ($O3(\lambda_s)$) of one subject to be discriminated are stored as the basis vectors of the short wavelength range. Here, $\lambda_s$ represents a wavelength in the short wavelength range, and the short wavelength range in this embodiment is assumed as $\lambda_s=380$ nm to 650 nm. The basis vectors ($O1(\lambda_l)$ and $O2(\lambda_l)$) of two subjects not to be discriminated, and the special basis vector ($O3(\lambda_l)$) of one subject to be discriminated are stored as the basis vectors of the long wavelength range. Here, $\lambda_l$ represents a wavelength in the long wavelength range, and the long wavelength range in this embodiment is assumed as $\lambda_s=550$ nm to 780 nm.

The data selecting unit 231 further receives the information about the color imaging system and illuminating light under the image acquisition conditions set through the external interface unit 122, from the control unit 121. According to the information, the data selecting unit 231 reads the spectral characteristics of the imaging system, including the spectral characteristics about the color imaging system to be used to capture image of subjects and the spectral characteristics about the illuminating light to be used to capture images of the subjects, from the system spectral characteristics ROM 119. In this manner, the system spectral characteristics ROM 119 and the data selecting unit 231 also function as a system spectral characteristics acquiring unit.

In this case, the system spectral characteristics ROM 119 stores M sets of spectral characteristics of the imaging system for each wavelength range in accordance with M kinds of wavelength ranges. In this embodiment, two sets of spectral characteristics with respect to the short wavelength range and the long wavelength range are stored, for example. More specifically, the spectral luminance characteristics ($I(\lambda_s)$) of the light source of the short wavelength range and the spectral luminance characteristics ($I(\lambda_l)$) of the light source of the long wavelength range are stored as the spectral characteristics about the illuminating light to be used to capture image of the subjects. Also, the spectral sensitivity characteristics (SB1 ($\lambda_s$), SB2($\lambda_s$), and SG1($\lambda_s$)) of the color imaging system of the short wavelength range formed with the three color filters of B1, B2, and G1, and the spectral sensitivity characteristics (SG2($\lambda_l$), SR1($\lambda_l$), and SR2($\lambda_l$)) of the color imaging system of the long wavelength range formed with the three color filters of G2, R1, and R2 are stored as the spectral characteristics about the color imaging system.

The data selecting unit 231 transfers the basis vectors ($O1(\lambda_s)$, $O2(\lambda_s)$, and $O3(\lambda_s)$) and ($O1(\lambda_l)$, $O2(\lambda_l)$, and $O3(\lambda_l)$), the spectral luminance characteristics ($I(\lambda_s)$ and $I(\lambda_l)$) of the light source, and the spectral sensitivity characteristics (SB1 ($\lambda_s$), SB2($\lambda_s$), and SG1($\lambda_s$)) and (SG2($\lambda_1$), SR1($\lambda_l$), and SR2 ($\lambda_l$)) of the color imaging system, to the integrating unit 232.

Under the control of the control unit 121, the integrating unit 232 functions as a matrix calculating unit that calculates the system matrix independently with respect to a 3×3 imaging system for each of the short and long wavelength ranges. More specifically, the integrating unit 232 calculates the system matrix $M_s$ of the short wavelength range expressed by the following equation (5), and the system matrix $M_l$ of the long wavelength range expressed by the following equation (6):

$$M_s = \begin{bmatrix} \sum_{\lambda_s=380,650} I(\lambda_s) \cdot SB1(\lambda_s) \cdot O1(\lambda_s) & \sum_{\lambda_s=380,650} I(\lambda_s) \cdot SB1(\lambda_s) \cdot O2(\lambda_s) & \sum_{\lambda_s=380,650} I(\lambda_s) \cdot SB1(\lambda_s) \cdot O3(\lambda_s) \\ \sum_{\lambda_s=380,650} I(\lambda_s) \cdot SB2(\lambda_s) \cdot O1(\lambda_s) & \sum_{\lambda_s=380,650} I(\lambda_s) \cdot SB2(\lambda_s) \cdot O2(\lambda_s) & \sum_{\lambda_s=380,650} I(\lambda_s) \cdot SB2(\lambda_s) \cdot O3(\lambda_s) \\ \sum_{\lambda_s=380,650} I(\lambda_s) \cdot SG1(\lambda_s) \cdot O1(\lambda_s) & \sum_{\lambda_s=380,650} I(\lambda_s) \cdot SG1(\lambda_s) \cdot O2(\lambda_s) & \sum_{\lambda_s=380,650} I(\lambda_s) \cdot SG1(\lambda_s) \cdot O3(\lambda_s) \end{bmatrix} \quad (5)$$

$$M_l = \begin{bmatrix} \sum_{\lambda_1=550,780} I(\lambda_1) \cdot SG2(\lambda_1) \cdot O1(\lambda_1) & \sum_{\lambda_1=550,780} I(\lambda_1) \cdot SG2(\lambda_1) \cdot O2(\lambda_1) & \sum_{\lambda_1=550,780} I(\lambda_1) \cdot SG2(\lambda_1) \cdot O3(\lambda_1) \\ \sum_{\lambda_1=550,780} I(\lambda_1) \cdot SR1(\lambda_1) \cdot O1(\lambda_1) & \sum_{\lambda_1=550,780} I(\lambda_1) \cdot SR1(\lambda_1) \cdot O2(\lambda_1) & \sum_{\lambda_1=550,780} I(\lambda_1) \cdot SR1(\lambda_1) \cdot O3(\lambda_1) \\ \sum_{\lambda_1=550,780} I(\lambda_1) \cdot SR2(\lambda_1) \cdot O1(\lambda_1) & \sum_{\lambda_1=550,780} I(\lambda_1) \cdot SR2(\lambda_1) \cdot O2(\lambda_1) & \sum_{\lambda_1=550,780} I(\lambda_1) \cdot SR2(\lambda_1) \cdot O3(\lambda_1) \end{bmatrix} \quad (6)$$

The system matrixes $M_s$ and $M_l$ calculated by the integrating unit 232 are transferred to and stored in the buffer 233. Under the control of the control unit 121, the inverse-matrix calculating unit 234 reads the system matrixes $M_s$ and $M_l$ from the buffer 233, and calculates the inverse matrixes $M_s^{-1}$ and $M_l^{-1}$ of the system matrixes $M_s$ and $M_l$. The calculated inverse matrixes $M_s^{-1}$ and $M_l^{-1}$ are transferred to and stored in the buffer 235.

With the use of the inverse matrixes $M_s^{-1}$ and $M_l^{-1}$ of the system matrixes, a three-color frame signal formed with B1, B2, and G1, and a three-color frame signal formed with G2, R1, and R2, the weighting coefficients ($w1_{sij}$, $w2_{sij}$, and $w3_{sij}$) and ($w1_{lij}$, $w2_{lij}$, and $w3_{lij}$) with respect to the basis vectors ($O1(\lambda_s)$, $O2(\lambda_s)$, and $O3(\lambda_s)$) and ($O1(\lambda_l)$, $O2(\lambda_l)$, and $O3(\lambda_l)$) can be determined for each pixel according to the following equations (7) and (8). In the following equations (7) and (8), i and j represent the x- and y-direction coordinates of the frame signal, $m_s$ and $m_l$ represent the elements of the inverse matrixes $M_s^{-1}$ and $M_l^{-1}$ of the system matrixes or the coefficients of the inverse matrixes $M_s^{-1}$ and $M_l^{-1}$.

$$\begin{bmatrix} w1_{sij} \\ w2_{sij} \\ w3_{sij} \end{bmatrix} = M_s^{-1} \begin{bmatrix} B1_{ij} \\ B2_{ij} \\ G1_{ij} \end{bmatrix} = \begin{bmatrix} m_{s11} & m_{s12} & m_{s13} \\ m_{s21} & m_{s22} & m_{s23} \\ m_{s31} & m_{s32} & m_{s33} \end{bmatrix} \begin{bmatrix} B1_{ij} \\ B2_{ij} \\ G1_{ij} \end{bmatrix} \quad (7)$$

$$\begin{bmatrix} w1_{lij} \\ w2_{lij} \\ w3_{lij} \end{bmatrix} = M_l^{-1} \begin{bmatrix} G2_{ij} \\ R1_{ij} \\ R2_{ij} \end{bmatrix} = \begin{bmatrix} m_{l11} & m_{l12} & m_{l13} \\ m_{l21} & m_{l22} & m_{l23} \\ m_{l31} & m_{l32} & m_{l33} \end{bmatrix} \begin{bmatrix} G2_{ij} \\ R1_{ij} \\ R2_{ij} \end{bmatrix} \quad (8)$$

In this embodiment, the subject to be discriminated is oxyhemoglobin that is contained in large amounts in the blood vessels, essential in diagnosis with an endoscope. Therefore, only the weighting coefficients ($w3_{sij}$) and ($w3_{lij}$) with respect to the special basis vectors ($O3(\lambda_s)$) and ($O3(\lambda_l)$) should be determined. Accordingly, the coefficients of the inverse matrix $M^{-1}$ of the required system matrix are the six elements $m_{s31}$, $m_{s32}$, $m_{s33}$, $m_{l31}$, $m_{l32}$, and $m_{l33}$.

Under the control of the control unit 121, the coefficient selecting unit 236 selects the elements $m_{s31}$, $m_{s32}$, and $m_{s33}$ and the elements $m_{l31}$, $m_{l32}$, and $m_{l33}$ of the inverse matrixes $M_s^{-1}$ and $M_l^{-1}$ of the system matrixes, from the buffer 235 and transfers the selected elements to the multiplying/adding unit 237. Under the control of the control unit 121, the multiplying/adding unit 237 reads the frame signal $B1_{ij}$, $B2_{ij}$, $G1_{ij}$ and the frame signal $G2_{ij}$, $R1_{ij}$, $R2_{ij}$ from the interpolating unit 114 for each pixel, after the elements $m_{s31}$, $m_{s32}$, and $m_{s33}$, and the elements $m_{l31}$, $m_{l32}$, and $m_{l33}$ of the inverse matrixes $M_s^{-1}$ and $M_l^{-1}$ of the system matrixes are transferred from the coefficient selecting unit 236. The multiplying/adding unit 237 then performs the multiplying and adding operations expressed by the following equations (9) and (10), to determine the weighting coefficients ($w3_{sij}$) and ($w3_{lij}$) with respect to the special basis vectors ($O3(\lambda_s)$) and ($O3(\lambda_l)$) of the subject to be discriminated:

$$w3_{sij} = m_{s31} \cdot B1_{ij} + m_{s32} \cdot B2_{ij} + m_{s33} \cdot G1_{ij} \quad (9)$$

$$w3_{lij} = m_{l31} \cdot G2_{ij} + m_{l32} \cdot R1_{ij} + m_{l33} \cdot R2_{ij} \quad (10)$$

The weighting coefficients ($w3_{sij}$) and ($w3_{lij}$) are the ratios of contribution to the special basis vectors ($O3(\lambda_s)$) and ($O3(\lambda_l)$) of the subject to be discriminated. Therefore, the weighting coefficients ($w3_{sij}$) and ($w3_{lij}$) in this embodiment are values proportional to the existence of oxyhemoglobin. Accordingly, each weighting coefficient has a higher value when oxyhemoglobin exists, and has a lower value when oxyhemoglobin does not exist. The weighting coefficient ($w3_{sij}$) about the short wavelength range has a value proportional to the existence of oxyhemoglobin in surface tissues, and the weighting coefficient ($w3_{lij}$) about the long wavelength range has a value proportional to the existence of oxyhemoglobin in deep tissues. Accordingly, by converting the weighting coefficients ($w3_{sij}$) and ($w3_{lij}$) into image signals, the oxyhemoglobin existing in the surface tissues and the oxyhemoglobin existing in the deep tissues can be discriminated independently of each other, or the blood vessels in the surface layer and the blood vessels in the deep layer can be discriminated independently of each other.

The weighting coefficients ($w3_{sij}$) and ($w3_{lij}$) calculated by the multiplying/adding unit 237 are transferred one by one to the falsely-colored processing unit 116, and the above described normalizing processing is performed. Different colors are assigned to the weighting coefficients after the normalizing processing, to obtain false color image signals. The first output unit 117 functioning as a display monitor displays the false color image signals as the output signals indicating the results of the discrimination of the subject having the known spectral characteristics.

In the above description, the subject to be discriminated is oxyhemoglobin, which is contained in large amounts in arteries. However, the subject to be discriminated is not limited to that in the present invention. For example, if necessary, the subject to be discriminated may be switched to deoxyhemoglobin, which is contained in large amounts in veins, via the external interface unit 122.

As described above, in accordance with the first embodiment, the following procedures are carried out: separating N kinds (N being a natural number of 2 or greater) of color signals forming a image signal obtained by capturing an image of a subject with a color imaging system, into M kinds (M being a natural number of 1 or greater, M≦N) of wavelength ranges, based on the known spectral characteristics of the subject to be discriminated, at least one of the separated wavelength ranges including a plurality of color signals; estimating a noise amount in each predetermined unit area in each of the separated wavelength ranges; performing a noise reducing processing on each of the separated wavelength ranges, based on the estimated noise amount; and performing a discriminating processing on the subject to be discriminated, based on the color signals in the wavelength ranges subjected to the noise reduction. In this manner, when a subject to be discriminated is discriminated from image signal obtained by a color imaging system for acquiring image of subjects including the subject to be discriminated, the N kinds of color signals forming the image signal are separated into the M kinds of wavelength ranges, based on the known spectral characteristics of the subject to be discriminated. A noise reducing processing is performed on each of the separated wavelength ranges. A discriminating processing is then performed, based on the color signals in the wavelength ranges subjected to the noise reduction. In this manner, the subject to be discriminated can be discriminated with high reliability. Since the discriminating processing is performed based on the color signals in the wavelength ranges subject to the noise reduction, highly-reliable discrimination with excellent resistance to noise can be performed.

The N kinds of color signals constituting the image signal are preferably four or more kinds of color signals, and the M kinds of separated wavelength ranges are preferably two or more kinds of wavelength ranges. With the N being four or greater, M being two or greater, each wavelength range can include a plurality of color signals after a plurality of wavelength ranges are separated from one another. Accordingly, the pixel spacing among the pixels to be used becomes narrower. In this manner, a larger noise reducing effect can be achieved.

The output value of each color signal about the subject to be discriminated is predicted, and color signals having similar output values to the predicted output values are selected. The number of groups of selected color signals is adjusted to determine the wavelength ranges. The color signals of the subject to be discriminated that have output values similar to one another are selected, to set the wavelength range. Accordingly, the noise levels in the wavelength range become almost the same, and a noise reducing processing can be performed with higher precision. Since the number of groups of selected color signals is adjusted, more than one wavelength range can be processed with the same processing system, and the costs of the system can be lowered. Each wavelength range is calculated based on the spectral characteristics of the subject to be discriminated, the spectral characteristics about the color imaging system, and the spectral characteristics about the illuminating light to be used for image acquisition. Accordingly, it is possible to flexibly cope with changing subjects to be discriminated, updating the system, and the like.

The various kinds of information about the noise amount are dynamically acquired every time an image is captured, and a standard value is set for information that cannot be acquired, so as to determine the noise amount according to a lookup table. Accordingly, it becomes possible to dynamically cope with varying conditions every time an image is captured, and perform high-precision and stable noise amount estimation. Also, since the lookup table is used to calculate the noise amount, high-speed noise amount estimation can be performed.

A check is made to determine whether the pixel value of the target pixel group falls within the noise range, based on the estimated noise amount of the target pixel group. When the pixel value falls within the noise range, a smoothing processing is performed on the pixel value. When the pixel value does not fall within the noise range, a correcting processing is performed on the pixel value. By making a determination about a noise reducing processing based on the noise amount, an optimum noise reducing processing can be performed. Also, discontinuity due to the noise reducing processing can be prevented, and high-quality image signal can be generated.

Further, the special basis vector based on the known spectral characteristics of the subject to be discriminated is used, so that a weighting coefficient with a value proportional to the existence of the subject to be discriminated can be calculated. Therefore, there is no need to perform a signal processing that may include errors, such as an approximation based on the conventional least-squares method. Accordingly, fewer errors are caused by signal processing, and highly-reliable discrimination can be performed. Also, since the regular illuminating light of a wide range is used, the influence of noise can be reduced, and stable discrimination can be performed. Further, since output signal is calculated directly from the weighting coefficients about the special basis vector, processing can be performed at higher speed and at lower cost.

The inverse matrixes of the system matrixes based on the special basis vector and the spectral characteristics of the imaging system are calculated, and coefficients related to the special basis vector are selected from the inverse matrixes. The weighting coefficients about the special basis vector are calculated, based on the selected coefficients and image signal. Accordingly, the weighting coefficients of the special basis vector, i.e., the subject to be discriminated, can be calculated through a signal processing based on the spectral characteristics of the subject to be discriminated and the spectral characteristics of the imaging system. With this arrangement, highly-reliable discrimination with fewer errors caused by signal processing can be performed.

Since four or more kinds of color signals constitute image signal, each of the separated wavelength ranges can include a plurality of color signals. Accordingly, the pixel spacing among the pixels to be used becomes narrower, and a larger noise reducing effect can be achieved.

Since color image signal subjected to regular processing is also calculated independently, the entire image signal can be discriminated, and the user friendliness is enhanced accordingly. Further, the spectral characteristics of the color signals required to calculate the regular color image signal are set in a wider band than the spectral characteristics of the other color signals. Accordingly, the noise of the color signals required to calculate the regular color image signal is reduced, and high-quality image signal can be obtained. In the calculation of the regular color image signal, a noise reducing processing is not performed, and an increase in system costs can be restricted.

Although an example case where video image is processed has been described in the above description, a still image may be captured by operating the shutter button (not shown) of the external interface unit 122, and the same processing as above may be performed on the still image.

In the first embodiment, the two output units, the first output unit 117 and the second output unit 120, are provided, but the present invention is not limited to that structure.

For example, one output unit may be used by switching as needed, as illustrated in FIG. 17. The endoscope illustrated in FIG. 17 has the same structure as the structure illustrated in FIG. 1, except that the second output unit 120 is eliminated, and a switching unit 125 is added. The basic structure is the same as that illustrated in FIG. 1, and the same components as those in the first embodiment are referred to using the same names and denoted by the same reference numerals as those in the first embodiment. In the following, only the different aspects from the first embodiment are described.

The buffer 107 is connected to the switching unit 125. The switching unit 125 is connected to the signal processing unit 110 and the separating unit 111. The signal processing unit 110 is connected to the first output unit 117. The switching unit 125 and the control unit 121 are bidirectionally connected to each other.

When an instruction to display the regular color image is issued from the user via the external interface unit 122, the switching unit 125 enters a regular mode, under the control of the control unit 121. In the regular mode, the switching unit 125 selects single frame signal formed with the three color signals of R1, G1, and B1 from the buffer 107, and transfers the frame signal to the signal processing unit 110. The signal processing unit 110 then performs the processing described in the above first embodiment, and transfers the regular color image signal to the first output unit 117. The first output unit 117, which is a display monitor, for example, displays the regular color image signal.

When an instruction to output the results of discrimination of the subject to be discriminated is issued from the user via the external interface unit 122, the switching unit 125 enters a discrimination mode, under the control of the control unit 121. In the discrimination mode, the switching unit 125 reads the single frame signal formed with N kinds (N being a natural number of 2 or greater, for example, 6) of color signals from the buffer 107, and transfers the frame signal to the separating unit 111. The separating unit 111, the noise estimating unit 112, the noise reducing unit 113, the interpolating unit 114, the calculating unit 115, and the falsely-colored processing unit 116 perform the processing described in the first embodiment. The frame signal about the existence of the subject to be discriminated is transferred to and displayed on the output unit 117. Accordingly, the separating unit 111, the noise estimating unit 112, the noise reducing unit 113, the interpolating unit 114, the calculating unit 115, and the falsely-colored processing unit 116 function when the switching unit 125 is in the discrimination mode.

As described above, switching can be made between the discrimination mode and the regular mode. Accordingly, the applicability of the system is improved, and the system can be used in a wider variety of fields.

Alternatively, the signal processing unit 110 and the second output unit 120 may be removed from the structure illustrated in FIG. 1, as shown in FIG. 18.

In this structure, the regular color image signal is not output, and only the results of discrimination are output.

In the first embodiment, the discrimination apparatus is a structure integrally formed with the image acquisition unit including the imaging lens unit 100, the CCD 101, the illuminating lens unit 102, the illuminating light source 103, the optical fibers 104, the amplifier unit 105, the ADC 106, the WB unit 108, and the measured light evaluating unit 109. However, the present invention is not limited to that structure.

For example, image signal generated from an independent image acquisition device may be stored as unprocessed Raw data on a recording medium such as a hard disk or a memory card, with additional information being recorded on the header portion. The additional information indicates the image acquisition conditions with respect to the subject to be discriminated, the color imaging system, the illuminating light, and the like. The signal and the header information may be read from the recording medium, and be processed. Alternatively, signal and header information transmitted via a wireless or wired network may be received and processed.

FIG. 19 illustrates a discrimination apparatus that is the same as the structure illustrated in FIG. 1, except that the imaging lens unit 100, the CCD 101, the illuminating lens unit 102, the illuminating light source 103, the optical fibers 104, the amplifier unit 105, the ADC 106, the WB unit 108, and the measured light evaluating unit 109 are removed, and an input unit 126 and a header information analyzing unit 127 are added. The basic structure is the same as the structure illustrated in FIG. 1, and the same components as those in the first embodiment are referred to using the same names and denoted by the same reference numerals as those in the first embodiment. In the following, only the different aspects from the first embodiment are described.

The input unit 126 is connected to the buffer 107 and the header information analyzing unit 127. The control unit 121 is bidirectionally connected to the input unit 126 and the header information analyzing unit 127. When the user starts a replaying processing through the external interface unit 122, such as a mouse or a keyboard, the signal and the header information stored on the recording medium, such as a hard disk or a memory card, or the signal and the header information received via a network, are read from the input unit 126. The image signal is sequentially read in frame by frame at predetermined time intervals, or at one-frame time interval in this modification. The signal from the input unit 126 is transferred to the buffer 107, and the header information from the input unit 126 is transferred to the header information analyzing unit 127 respectively. The header information analyzing unit 127 extracts the information about the image capturing from the header information, and transfers the extracted information to the control unit 121. The procedures to be carried out hereafter are the same as those illustrated in FIG. 1.

It is of course possible to apply this modification to either video image or still image.

In the above described first embodiment, the processing is assumed to be conducted by the hardware. However, this is not limiting; for example, processing may be performed by software through a computer (not shown). In such a case, an image signal from the CCD 101 is stored as unprocessed Raw data and the information such as the image acquisition conditions of the subject to be discriminated, the color imaging system, and the illuminating light, the temperature value of the color imaging system, and the gain value with respect to the image signal is output as header information from the control unit 121. The image signal and the header information are then input to the computer.

FIG. 20 is a flowchart of a software signal processing to be performed by the computer (not shown).

First, the computer receives a image signal and the header information about the information such as the image acquisition conditions of the subject to be discriminated, the color imaging system, and the illuminating light, the temperature value, the gain value, and the like (step S101). In this modification, image signal supplied from a single CCD having the filter 123 formed with the six kinds of color filters of FIG. 2 at the front face are to be processed. However, the header information need not contain any of the information about the temperature value, the gain value, and the like.

After step S101, basis vectors as shown in FIG. 7 are input to the computer (step S102). Also, spectral luminance characteristics of the light sources shown in FIG. 8 and spectral sensitivity characteristics of color imaging systems shown in FIG. 9 are input (step S103). A noise amount table designed for determining a noise amount from the signal level and information such as the temperature value and the gain value is input (step S104). Here, the basis vectors, the spectral characteristics of imaging systems, and the noise amount table may be loaded from a recording medium provided in the computer or a recording medium detachably attached to the computer, or may be loaded via a network.

A calculating processing that will be described later in detail is then performed to calculate the predetermined coefficients or the elements $m_{s31}$, $m_{s32}$, and $m_{s33}$, and the elements $m_{l31}$, $m_{l32}$ and $m_{l33}$ of the inverse matrixes $M_s^{-1}$ and $M_l^{-1}$ of the system matrixes to be used for calculating the weighting coefficients of the basis vectors (step S105). The frame signals are then sequentially extracted from the input image signal (step S106).

The color signals for generating the regular color image signal are separated, and missing color signals are generated by a known interpolating technique. In this manner, frame signal formed with the color signals for generating the regular color image signal is generated, and signal processing such as the known gradation processing and enhancement processing is performed to generate the regular color image signal (step S107). The regular color image signal is output in frame signal unit to a display monitor or the like (not shown) connected to the computer (step S108). A check is then made to determine whether all of the frame signals have been processed (step S109). If the processing on all the frame signals is not completed, the processing returns to step 106. If the processing on all the frame signals is completed, the processing comes to an end.

In parallel with the signal processing of step S107, a separating processing, which will be described later in detail, is performed to select and separate the color signals corresponding to the M kinds (M being a natural number of 1 or greater) of frequency ranges (two kinds in this embodiment) to be used in signal processing with the use of basis vectors, from the image signal formed with the N kinds (N being a natural number of 2 or greater, M≦N) of color signals (six kinds in this embodiment) that are input at step S101 (step S110).

After that, the pixel region of a predetermined unit area including the target pixel group consisting of the target pixels of the respective color signals to be subjected to a noise reduction is extracted from one of the separated wavelength ranges (step S111). For example, 4×7 pixels including the target pixel group 124 as shown in FIG. 12 are extracted as the pixel region with respect to each wavelength range. A noise estimating processing that will be described later in detail is then performed to estimate a noise amount about the extracted pixel region (step S112). Further, a noise reducing processing that will be described later in detail is performed based on the estimated noise amount, to reduce the noise in the target pixel group in the pixel region (step S113). A check is then made to determine whether the noise reducing processing has been performed on the entire pixel region in the separated wavelength ranges (step S114). If the noise reducing processing is not completed, the processing returns to step S111, and the target pixel group is updated to extract the next pixel region.

If the noise reducing processing is determined to have been performed on the entire pixel region at step S114, a check is made to determine whether the noise reducing processing has been performed on all the wavelength ranges separated at step S110 (step S115). If the noise reducing processing has not been performed on all the wavelength ranges, the processing returns to step S111, and the pixel region of the predetermined unit area including the target pixel group to be subjected to a noise reduction is extracted from the next wavelength range.

If the noise reducing processing is determined to have been performed on all the wavelength ranges at step S115, six kinds of frame signals formed with the six kinds of color signals are generated from the signals of the respective noise-reduced wavelength ranges by the known interpolating technique (step S116). A multiplying and adding processing is then performed on the frame signals, to calculate the weighting coefficients with respect to the special basis vectors according to the equation (9) or (10) (step S117). For example, the weighting coefficient ($w3_{sij}$) with respect to the special basis vector ($O3(\lambda_s)$) is calculated according to the equation (9), for the three frame signals of the color signals in the short wavelength range. The weighting coefficient ($w3_{lij}$) with respect to the special basis vector ($O3(\lambda_l)$) is calculated according to the equation (10), for the three frame signals of the color signals in the long wavelength range. The calculated weighting coefficients are normalized, and different colors between the wavelength ranges are assigned to the normalized weighting coefficients, to generate false color image signal (step S118). For example, the weighting coefficient ($w3_{sij}$) is normalized, and red is assigned to the normalized weighting coefficient. The weighting coefficient ($w3_{lij}$) is normalized, and cyan is assigned to the normalized weighting coefficient. In this manner, the false color image signals are generated. The false color image signals about the existence of the subject to be discriminated are then output in frame signal unit to a display monitor (not shown) connected to the computer (step S108). After that, a check is made to determine whether all the frame signals have been processed (step S109). If the processing is not completed, the processing returns to step S106. If the processing is completed, the processing comes to an end.

At step S108, the regular color image signal and the false color image signals as the result of discrimination are output. Two or more display monitors or the like may be connected to the computer, and the regular color image signal may be displayed separately from the false color image signals. Alternatively, only one display monitor or the like may be connected to the computer, and the regular color image signal may be displayed in a window other than the window in which the false color image signals are displayed.

Also, the display on a single display monitor may be switched by a user. In such a case, the procedure of step S107 and the procedures of steps S110 through S118 are not necessarily carried out in parallel, and a user may select either the procedure of step S107 or the procedures of steps S110 through S118.

In the calculating processing at step S105, data selection is first performed (step S201), as shown in FIG. 21. More specifically, the basis vectors, the spectral luminance characteristics of the light source, and the spectral sensitivity characteristics of the color imaging system that are to be used in this processing are selected from the basis vectors that are input at step S102, and the spectral luminance characteristics of light sources and the spectral sensitivity characteristics of color imaging systems that are input at step S103, based on the image acquisition conditions of the subject to be discriminated, the color imaging system, and the illuminating light in the header information that is input at step S101. For example, the basis vectors ($O1(\lambda)$, $O2(\lambda)$, and $O3(\lambda)$ shown in FIG. 7, the spectral luminance characteristics of the light source shown in FIG. 8, and the spectral sensitivity characteristics of the color imaging system shown in FIG. 9 are selected.

After that, the integrating processing to calculate system matrixes according to the equation (5) or (6) is performed (step S202), and the inverse matrixes of the system matrixes are further calculated (step S203). For example, system matrixes $M_s$ and $M_l$ are calculated, and the inverse matrixes $M_s^{-1}$ and $M_l^{-1}$ of the system matrixes $M_s$ and $M_l$ are also calculated. The elements of the inverse matrixes required to calculate the weighting coefficients of the basis vectors are then selected as the predetermined coefficients (step S204), and the selected elements of the inverse matrixes are output (step S205). For example, the elements $m_{s31}$, $m_{s32}$, and $m_{s33}$ of the inverse matrix $M_s^{-1}$ required to calculate the weighting coefficient ($w3_{sij}$) of the basis vector ($O3(\lambda_s)$), and the elements $m_{l31}$, $m_{l32}$, and $m_{l33}$ of the inverse matrix $M_l^{-1}$ required to calculate the weighting coefficient ($w3_{lij}$) of the basis vector ($O3(\lambda_l)$) are selected and output.

In the separating processing at step S110, the output value of each color signal is first predicted (step S211), as shown in FIG. 22. More specifically, the basis vectors, the spectral luminance characteristics of the light source, and the spectral sensitivity characteristics of the color imaging system that are to be used in this processing are selected from the basis vectors that are input at step S102, and the spectral luminance characteristics of light sources and the spectral sensitivity characteristics of color imaging systems that are input at step S103, based on the image acquisition conditions of the subject to be discriminated, the color imaging system, and the illuminating light contained in the header information that is input at step S101. Based on the selected basis vectors, spectral luminance characteristics, and spectral sensitivity characteristics, the output value of each color signal is predicted.

After that, based on the predicted output values of the respective color signals, color signals having similar output values to the predicted ones are selected (step S212). This procedure is carried out by selecting color signals having similar signal values to one another or color signals falling within a predetermined range, and putting those color signals into the same group by a known clustering technique. After that, the number of selected color signal groups is adjusted, to determine the M kinds (two kinds in this embodiment) of wavelength ranges (step S213). Based on the determined wavelength ranges, the color signals corresponding to the M kinds of frequency ranges are selected and separated from the image signal that is the single frame signal formed with the N kinds of color signals and is input at step S101 (step S214).

In the noise estimating processing at step S112, the information such as the temperature value and the gain value contained in the header information that is input at step S101 is first set as the noise-related information to be used in the noise estimating processing (step S221), as shown in FIG. 23. If the information such as the temperature value and the gain value is not contained in the header information, a standard value may be loaded from a recording medium provided in the computer or a recording medium detachably attached to the computer, or may be loaded via a network.

After that, the color pixel region including the target pixel of a color signal is extracted from the pixel region that is extracted at step S111 and includes the target pixel group to be subjected to a noise reduction (step S222). For example, the region of the color signal, such as only G2 or only R1 or the like in each pixel region formed with 4×7 pixels including the target pixel group 124 shown in FIG. 12, is selected as a color pixel region. The low-frequency components are then calculated from the extracted color pixel region (step S223). With the use of the noise amount table that is input at step S104, the noise amount of the pixels in the color pixel region is calculated from the noise-related information that is set at step S221 and the low-frequency components calculated at step S223 (step S224). After that, a check is made to determine whether the noise amount calculating processing has been performed on all the color pixel regions in the pixel region (step S225). If the noise amount calculating processing is not completed, the processing returns to step S222, and the next color pixel region is extracted.

If the noise amount calculating processing is determined to have been performed on all the color pixel regions in the pixel region at step S225, an average value is calculated (step S226). More specifically, the average value of the calculated noise amounts $N_c$ of the respective color signals is calculated as the noise amount of the entire color pixel region of each color signal, and the average value is assigned as the uniform noise amount $N_b$ to the three target pixels forming the target pixel group included in the pixel region, such as the three pixels of B1, B2, and G1 surrounded by the bold-line frames in FIG. 11. The average value of the low-frequency components of the color signals calculated at step S223 is calculated as the average value $AV_b$ of the pixels in the pixel region. The noise amount $N_b$ estimated in the pixel region of the predetermined unit area and the average value $AV_b$ of the pixels in the pixel region are then output (step S227).

In the noise reducing processing at step S113, the upper limit Noise_Up$_b$ and the lower limit Noise_Low$_b$ as the acceptable noise amount range according to the equations (1) are first set, based on the average value $AV_b$ and the noise amount $N_b$ of the pixels estimated in the noise estimating processing of step S112 (step S231), as shown in FIG. 24.

After that, the pixel value $P_c$ of the target pixel group 124 is read from the pixel region extracted at step S111, and a check is made to determine whether the pixel value $P_c$ falls within the acceptable range (step S232). The determination result is one of the following three: "within the noise range", "higher than the noise range", and "lower than the noise range".

If the pixel value $P_c$ of the target pixel group 124 in the extracted pixel region is determined to fall within the noise range, the first smoothing processing according to the equation (2) is performed to set the average value $AV_b$ as the value of the target pixel group 124 (step S233).

If the pixel value $P_c$ of the target pixel group 124 in the extracted pixel region is determined not to fall within the noise range, the second smoothing processing according to the equation (3) or (4) is performed to correct the pixel value $P_c$ of the target pixel group 124 with the use of the average value $AV_b$ and the noise amount $N_b$ estimated at step S112 (step S234).

The result of the first smoothing processing or the second smoothing processing is then output as a noise-reduced signal (step S235).

In this modification, the color pixel region of each color signal is extracted from pixel regions of the predetermined unit area, and the noise amount is then extracted. However, it is of course possible to extract noise amounts from the pixel regions.

Figure 25:
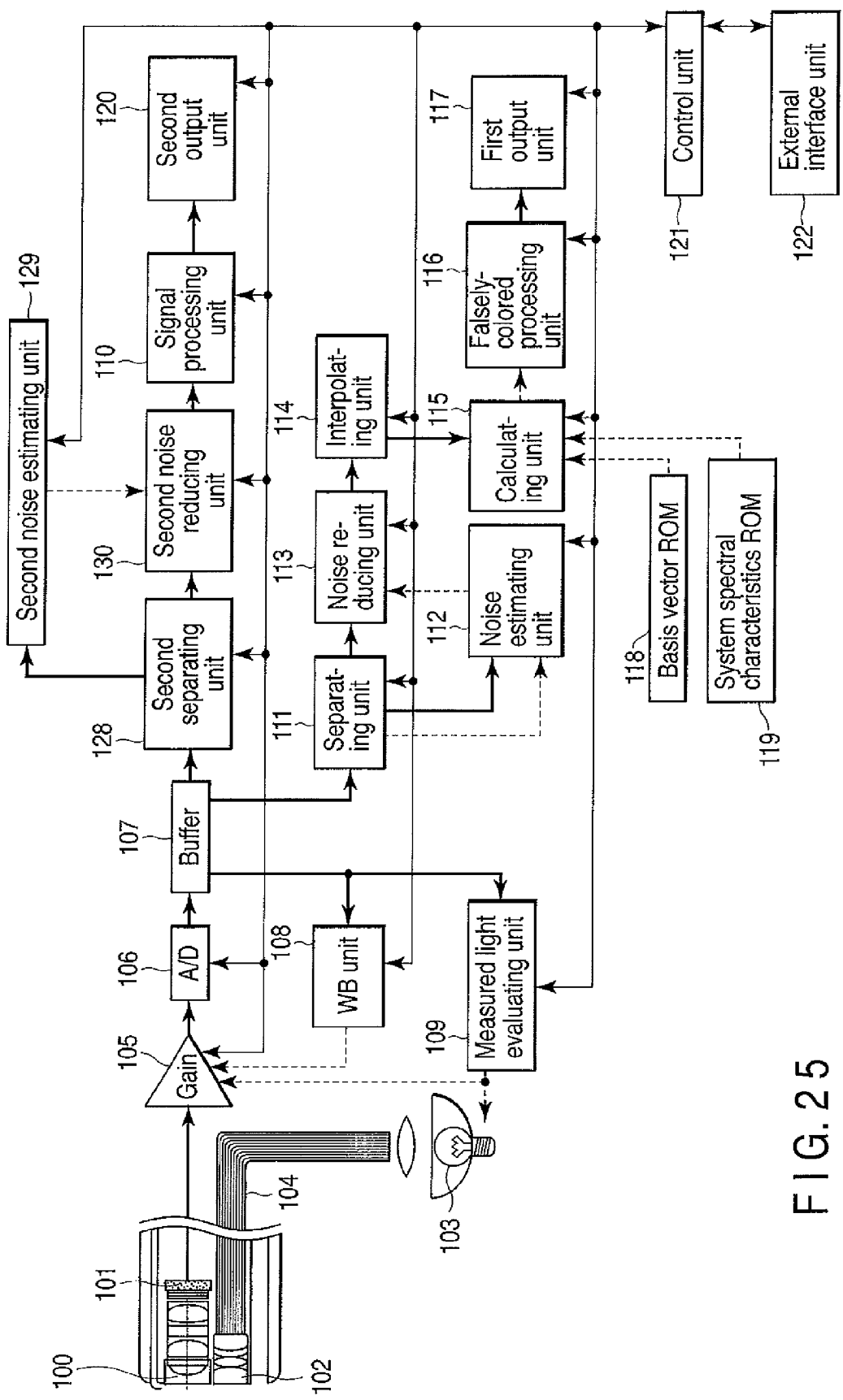
FIG. 25 illustrates the structure of an endoscope including a discrimination apparatus in accordance with a second embodiment of the present invention.

By referring now to FIG. 25, a second embodiment of the present invention is described. An endoscope including a discrimination apparatus in accordance with the second embodiment is the same as the structure of the first embodiment illustrated in FIG. 1, except that a second separating unit 128, a second noise estimating unit 129, and a second noise reducing unit 130 are added. The basic structure is the same as the structure of the first embodiment, and the same components as those in the first embodiment are referred to using the same names and denoted by the same reference numerals as those in the first embodiment. In the following, only the different aspects from the first embodiment are described.

The buffer 107 is connected to the second separating unit 128. The second separating unit 128 is connected to the second noise estimating unit 129 and the second noise reducing unit 130. The second noise estimating unit 129 is connected to the second noise reducing unit 130. The second noise reducing unit 130 is connected to the second output unit 120 such as a liquid crystal display via the signal processing unit 110. The control unit 121 is bidirectionally connected to the second separating unit 128, the second noise estimating unit 129, and the second noise reducing unit 130.

The functions of the discrimination apparatus in accordance with the second embodiment are basically the same as the first embodiment, and only the different aspects from the first embodiment are described in the following.

By referring to FIG. 25, the flows of signals are described. In this embodiment, the CCD 101 is assumed to be a single CCD having four kinds of color filters placed at its front face. FIG. 26 illustrates the structure of a filter 131 formed with the four kinds of color filters. This filter 131 has 2×2 pixels as basic units, and is formed with blue (B), green (G), yellow (Ye), and red (R) from the short wavelength side. FIG. 27 shows the spectral characteristics of the four kinds of color filters forming the filter 131. Through the filter 131, analog signal supplied from the CCD 101 turns into image signal formed with four kinds of color signals.

The image signal from the CCD 101 is then converted into digital signal in the same manner as in the first embodiment, and is transferred to the buffer 107.

Under the control of the control unit 121, the separating unit 111 selects and separates the color signals corresponding to M kinds (M being a natural number of 1 or greater) of wavelength ranges (two kinds in this embodiment) to be used in signal processing with the use of basis vectors, from single frame signal formed with N kinds (N being a natural number of 2 or greater, M≦N) of color signals (four kinds in this embodiment) recorded in the buffer 107. In this embodiment, two kinds of wavelength ranges are also set as the signals of the frequency ranges that are to be used in the signal processing with the use of the basis vectors and are to be separated from the frame signal formed with the four kinds of color signals corresponding to the filter 131 shown in FIG. 26. The color signals forming the separated wavelength ranges are set in accordance with the subject to be discriminated. The signals of wavelength ranges separated by the separating unit 111 are transferred to the noise estimating unit 112 and the noise reducing unit 113.

As shown in FIG. 28, the separating unit 111 of this embodiment includes a wavelength range table unit 205, instead of the predicting unit 201, the selecting unit 202, and the adjusting unit 203 of the first embodiment. The wavelength range table unit 205 is connected to the wavelength range separating unit 204 and the noise estimating unit 112. The wavelength range separating unit 204 is connected to the noise estimating unit 112 and the noise reducing unit 113. The buffer 107 is connected to the wavelength range separating unit 204. The control unit 121 is bidirectionally connected to the wavelength range table unit 205 and the wavelength range separating unit 204.

The wavelength range table unit 205 outputs wavelength ranges, based on the known spectral characteristics of the subject to be discriminated. For example, FIG. 29 shows the basis vector ($O3(\lambda)$) of oxyhemoglobin ($HBO_2$) contained in large amounts in the blood vessels such as arteries that are essential in diagnosis with an endoscope, and the basis vector ($O4(\lambda)$) of the auto-fluorescence of collagen as a main subject in fluorescent observation. The wavelength range table unit 205 stores the M kinds (two kinds in this embodiment) of wavelength ranges corresponding to the respective special basis vector based on the known spectral characteristics of the subject to be discriminated. When the information about the subject to be discriminated under the image acquisition conditions that are set through the external interface unit 122 is input, the wavelength range table unit 205 outputs the M kinds of wavelength ranges suitable for the subject.

Under the control of the control unit 121, the wavelength range separating unit 204 selects the color signals corresponding to the M kinds of frequency ranges from the single frame signal formed with the N kinds of color signals recorded in the buffer 107, based on the wavelength ranges that are output from the wavelength range table unit 205. The wavelength range separating unit 204 then outputs the selected color signals to the noise estimating unit 112 and the noise reducing unit 113.

Where the filter 131 including the four kinds of color filters of B, G, Ye, and R shown in FIG. 26 is used, for example, the wavelength range separating unit 204 selectively reads B and G, and also selectively reads Ye and R from the single frame signal formed with the four kinds of color signals recorded in the buffer 107, if oxyhemoglobin having the spectral reflectance characteristics shown in FIG. 29 is the subject to be discriminated. In this manner, the wavelength range separating unit 204 separates the color signals corresponding to the M kinds (two kinds in this embodiment) of wavelength ranges. More specifically, the wavelength range separating unit 204 separates the color signals into a short wavelength range and a long wavelength range. If the subject to be discriminated is collagen having the spectral luminance characteristics shown in FIG. 29, the wavelength range separating unit 204 selectively reads B and R, and also selectively reads G and Ye from the single frame signal formed with the four kinds of color signals recorded in the buffer 107. In this manner, the wavelength range separating unit 204 separates the color signals corresponding to the M kinds (two kinds in this embodiment) of wavelength ranges. More specifically, the wavelength range separating unit 204 separates the color signals into two, a long/short wavelength range and a medium wavelength range.

Figure 31:
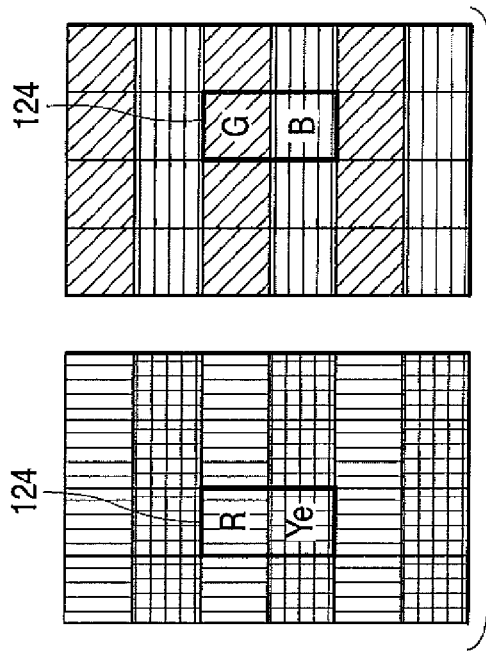
FIG. 31 shows examples of pixel regions each having a predetermined unit area including a target pixel group in the case where the subject to be discriminated is oxyhemoglobin.
Figure 33:
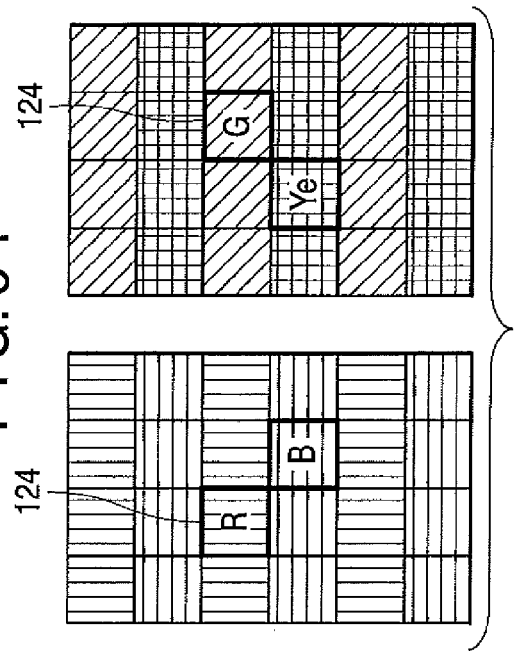
FIG. 33 shows examples of pixel regions each having a predetermined unit area including a target pixel group in the case where the subject to be discriminated is collagen.
Figure 30:
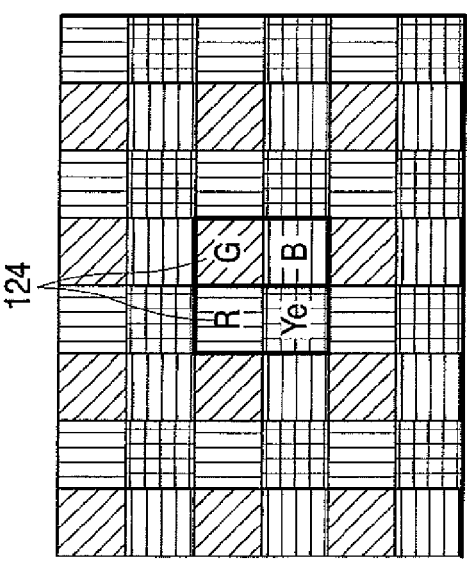
FIG. 30 shows an example of a unit block as the basic block in a noise reduction in a case where the subject to be discriminated is oxyhemoglobin.
Figure 32:
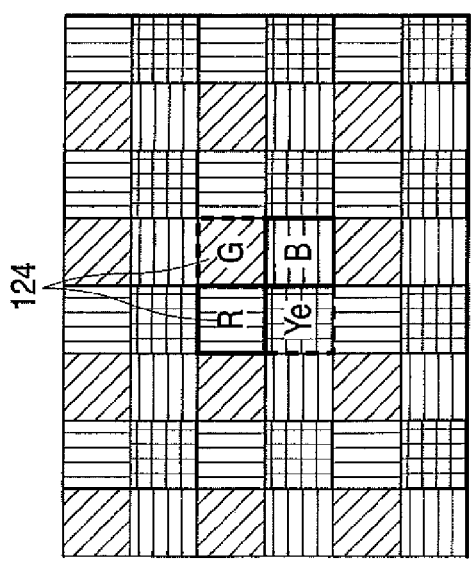
FIG. 32 shows an example of a unit block as the basic block in a noise reduction in a case where the subject to be discriminated is collagen.

The noise estimating unit 112, the noise reducing unit 113, the interpolating unit 114, the calculating unit 115, the falsely-colored processing unit 116, the first output unit 117, the basis vector ROM 118, and the system spectral characteristics ROM 119 are the same as those of the first embodiment. The region extracting unit 211 of the noise estimating unit 112 and the region extracting unit 221 of the noise reducing unit 113 each extract a pixel region of a predetermined unit area including a target pixel group. More specifically, when the subject to be discriminated is oxyhemoglobin, the region extracting unit 211 and the region extracting unit 221 each determines the target pixel groups 124 being formed with the two pixels of Ye and R and the two pixels of B and G, respectively, as indicated by the bold-line frames in FIG. 30, and a unit block of 8×6 pixels being the basic block in a noise reducing processing. Then, the region extracting unit 211 and the region extracting unit 221 each extract 4×6 pixels including the target pixel group 124 shown in FIG. 31 for each wavelength range. When the subject to be discriminated is collagen, the region extracting unit 211 and the region extracting unit 221 each determines the target pixel groups 124 being formed with the two pixels of B and R and the two pixels of G and Ye, respectively, as indicated by the bold-line frames and the dashed-line frames in FIG. 32, and a unit block of 8×6 pixels being the basic block in a noise reducing processing. Then, the region extracting unit 211 and the region extracting unit 221 each extract 4×6 pixels including the target pixel group 124 shown in FIG. 33 for each wavelength range.

Under the control of the control unit 121, the calculating unit 115 calculates the system matrixes with respect to the 2×2 size imaging system for each of the separated wavelength ranges, which are two wavelength ranges in this embodiment. If the subject to be discriminated is oxyhemoglobin, for example, the calculating unit 115 calculates the system matrix $M_1$ of the short wavelength range according to the equation (11) shown below, and the system matrix $M_2$ of the long wavelength range according to the equation (12) shown below. Here, $\lambda_1$ and $\lambda_2$ represents the wavelengths of the separated wavelength ranges.

$$M_1 = \begin{bmatrix} \sum I(\lambda_1) \cdot SB(\lambda_1) \cdot O3(\lambda_1) & \sum I(\lambda_1) \cdot SB(\lambda_1) \cdot O4(\lambda_1) \\ \sum I(\lambda_1) \cdot SG(\lambda_1) \cdot O3(\lambda_1) & \sum I(\lambda_1) \cdot SG(\lambda_1) \cdot O4(\lambda_1) \end{bmatrix} \quad (11)$$

$$M_2 = \begin{bmatrix} \sum I(\lambda_2) \cdot SYe(\lambda_2) \cdot O3(\lambda_2) & \sum I(\lambda_2) \cdot SYe(\lambda_2) \cdot O4(\lambda_2) \\ \sum I(\lambda_2) \cdot SR(\lambda_2) \cdot O3(\lambda_2) & \sum I(\lambda_2) \cdot SR(\lambda_2) \cdot O4(\lambda_2) \end{bmatrix} \quad (12)$$

After that, using the inverse matrixes $M_1^{-1}$ and $M_2^{-1}$ of the above system matrixes, the B and G signals, and the Ye and R signals, the calculating unit 115 calculates the weighting coefficients ($w3_{1ij}$ and $w4_{1ij}$) and ($w3_{2ij}$ and $w4_{2ij}$) about the basis vectors ($O3(\lambda_1)$ and $O4(\lambda_1)$) and ($O3(\lambda_2)$ and $O4(\lambda_2)$) for each pixel, according to the following equations (13) and (14):

$$\begin{bmatrix} w3_{1ij} \\ w4_{1ij} \end{bmatrix} = M_1^{-1} \begin{bmatrix} B_{ij} \\ G_{ij} \end{bmatrix} = \begin{bmatrix} m_{111} & m_{112} \\ m_{121} & m_{122} \end{bmatrix} \begin{bmatrix} B_{ij} \\ G_{ij} \end{bmatrix} \quad (13)$$

$$\begin{bmatrix} w3_{2ij} \\ w4_{2ij} \end{bmatrix} = M_2^{-1} \begin{bmatrix} Ye_{ij} \\ R_{ij} \end{bmatrix} = \begin{bmatrix} m_{211} & m_{212} \\ m_{221} & m_{222} \end{bmatrix} \begin{bmatrix} Ye_{ij} \\ R_{ij} \end{bmatrix} \quad (14)$$

In other words, the weighting coefficients ($w3_{1ij}$ and $w4_{1ij}$) and ($w3_{2ij}$ and $w4_{2ij}$) about the basis vectors ($O3(\lambda_1)$ and $O4(\lambda_1)$) and ($O3(\lambda_2)$ and $O4(\lambda_2)$) are calculated according to the following equations (15) through (18):

$$w3_{1ij} = m_{111} \cdot B_{ij} + m_{112} \cdot G_{ij} \quad (15)$$

$$w4_{1ij} = m_{121} \cdot B_{ij} + m_{122} \cdot G_{ij} \quad (16)$$

$$w3_{2ij} = m_{211} \cdot Ye_{ij} + m_{212} \cdot R_{ij} \quad (17)$$

$$w4_{2ij} = m_{221} \cdot Ye_{ij} + m_{222} \cdot R_{ij} \quad (18)$$

The weighting coefficients ($w3_{1ij}$ and $w4_{1ij}$) and ($w3_{2ij}$ and $w4_{2ij}$) calculated in the above manner are transferred to the falsely-colored processing unit 116.

Meanwhile, the second separating unit 128, under the control of the control unit 121, selects and separates the color signals required to calculate the regular color image signal, from the single frame signal formed with the N kinds (N being a natural number of 2 or greater) of color signals (four kinds in this embodiment) recorded in the buffer 107. For example, the four-color signals of B, G, Ye, and R are separated independently of one another, from the frame signal formed with the four kinds of color signals corresponding to the filter 131 shown in FIG. 26. The separated color signals are then transferred to the second noise estimating unit 129 and the second noise reducing unit 130.

As shown in FIG. 34, the second separating unit 128 includes a filter table unit 241 and a color signal separating unit 242. The filter table unit 241 is connected to the color signal separating unit 242. The color signal separating unit 242 is connected to the second noise estimating unit 129 and the second noise reducing unit 130. The buffer 107 is connected to the color signal separating unit 242. The control unit 121 is bidirectionally connected to the filter table unit 241 and the color signal separating unit 242.

The filter table unit 241 stores the wavelength ranges of each kind of color filter of CCD 101. When the information about the color imaging system under the above described image acquisition conditions that are set through the external interface unit 122 is input from the control unit 121, the filter table unit 241 outputs the wavelength ranges corresponding to the information about the color imaging system.

Under the control of the control unit 121, the color signal separating unit 242 separates the N kinds of color signals independently of each other from the single frame signal formed with the N kinds of color signals recorded in the buffer 107, in accordance with the wavelength ranges that are output from the filter table unit 241. The color signal separating unit 242 then outputs the separated color signals to the second noise estimating unit 129 and the second noise reducing unit 130.

The second noise estimating unit 129 estimates a noise amount of each of the color signals separated by the second separating unit 128 in each second predetermined unit area.

As shown in FIG. 35, the second noise estimating unit 129 includes a region extracting unit 251, a low-frequency calculating unit 252, a gain calculating unit 253, a standard value providing unit 254, and a noise table unit 255. The second separating unit 128 is connected to the region extracting unit 251. The region extracting unit 251 is connected to the low-frequency calculating unit 252. The low-frequency calculating unit 252, the gain calculating unit 253, and the standard value providing unit 254 are connected to the noise table unit 255. The noise table unit 255 is connected to the second noise reducing unit 130. The control unit 121 is bidirectionally connected to the region extracting unit 251, the low-frequency calculating unit 252, the gain calculating unit 253, the standard value providing unit 254, and the noise table unit 255.

Figure 36:
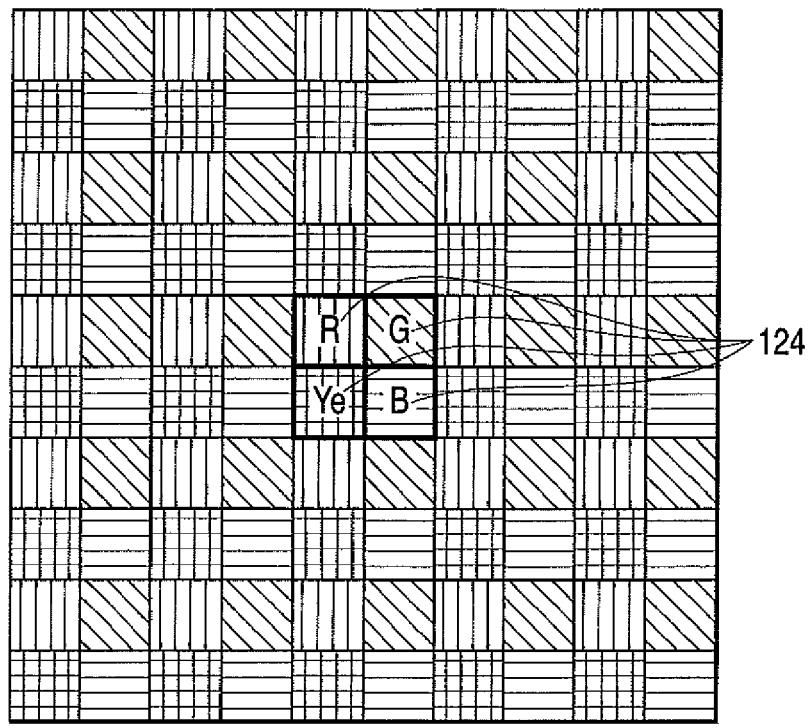
FIG. 36 shows an example of a basic block in a noise reduction for a regular color image signal.
Figure 37:
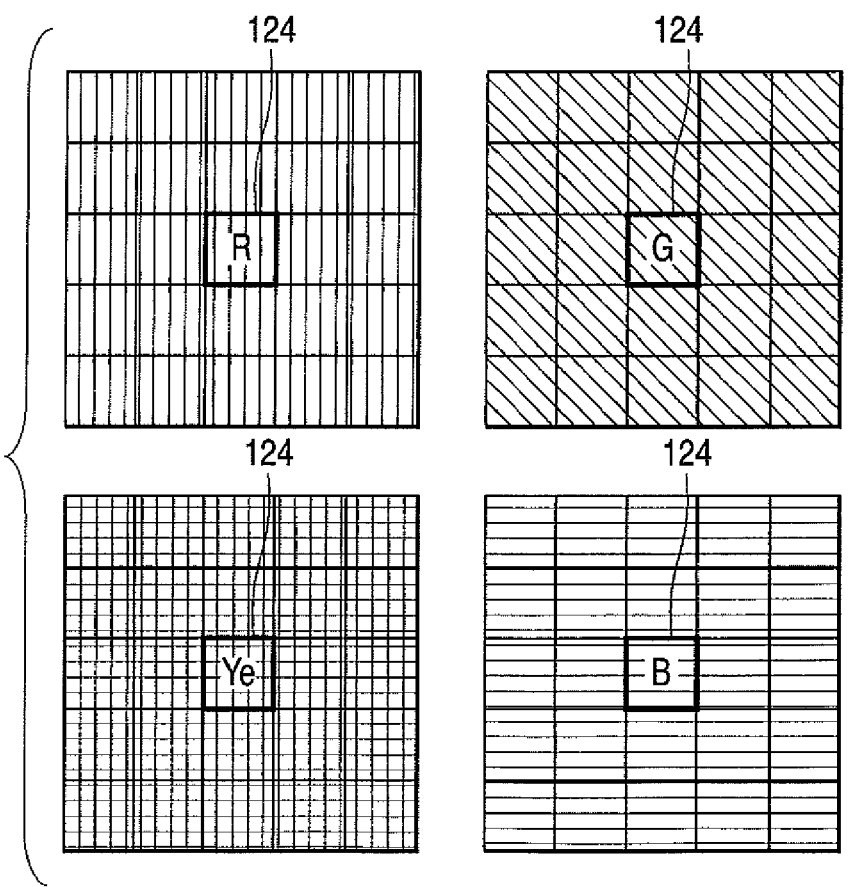
FIG. 37 shows examples of regions each having a second predetermined unit area including a target pixel group.

Under the control of the control unit 121, the region extracting unit 251 extracts a region including a target pixel group formed with the target pixels of each color signal to be subjected to a noise reduction, from the color signals separated by the second separating unit 128. For example, as indicated by the bold-line frames in FIG. 36, each of the four pixels of R, G, Ye, and B is regarded as a target pixel group 124, and a unit block of 10×10 pixels is set as the basic block for a noise reducing processing. In this case, each one target pixel group is formed with one target pixel. The region extracting unit 251 extracts 5×5 pixel blocks as sub blocks each including one target pixel group 124 as shown in FIG. 37 for the respective color signals. The sub blocks are the regions each having the second predetermined unit area including one target pixel group to be subjected to a noise reduction.

Under the control of the control unit 121, the low-frequency calculating unit 252 calculates the low-frequency components from the regions extracted by the region extracting unit 251.

Based on the information about the ISO sensitivity and the exposure conditions transferred from the control unit 121, the gain calculating unit 253 calculates the information about the gain values with respect to the image signal at the amplifier unit 105. The control unit 121 obtains the information about the temperature value of the color image acquisition unit with the use of a temperature sensor (not shown), as described in the first embodiment. Accordingly, the gain calculating unit 253 and the control unit 121 function as a collecting unit to collect the information about gain values and temperature values.

Under the control of the control unit 121, the standard value providing unit 254 functions as a provider unit to provide a standard value with respect to information that cannot be obtained by the collecting unit.

Under the control of the control unit 121, the noise table unit 255 outputs the noise amount of each target pixel group 124 included in the regions, with the inputs being the information provided from the collecting unit or the standard value providing unit 254 and the low-frequency components of the region of the second predetermined unit area calculated by the low-frequency calculating unit 252. More specifically, a noise amount $N_c$ is assigned to the target pixel groups 124 included in the regions, and is output to the second noise reducing unit 130. The low-frequency components of the respective color signals calculated by the low-frequency calculating unit 252 are output as the average value $AV_c$ of the pixels in the regions extracted by the region extracting unit 251, to the second noise reducing unit 130.

In the noise amount calculation, there is no need to obtain the information such as a temperature t and a gain g in each image acquisition processing. By storing given information beforehand in the standard value providing unit 254, the calculating processing may be omitted. In this manner, high-speed processing and power saving can be realized.

Based on the noise amount estimated by the second noise estimating unit 129, the second noise reducing unit 130 performs a noise reducing processing for each of the color signals separated by the second separating unit 128.

As shown in FIG. 38, the second noise reducing unit 130 includes a region extracting unit 261, a range setting unit 262, a switching unit 263, a first smoothing unit 264, and a second smoothing unit 265. The second separating unit 128 is connected to the region extracting unit 261. The region extracting unit 261 is connected to the range setting unit 262 and the switching unit 263. The second noise estimating unit 129 is connected to the range setting unit 262. The range setting unit 262 is connected to the switching unit 263, the first smoothing unit 264, and the second smoothing unit 265. The switching unit 263 is connected to the first smoothing unit 264 and the second smoothing unit 265. The first smoothing unit 264 and the second smoothing unit 265 are connected to the signal processing unit 110. The control unit 121 is bidirectionally connected to the region extracting unit 261, the range setting unit 262, the switching unit 263, the first smoothing unit 264, and the second smoothing unit 265.

Like the region extracting unit 251 of the second noise estimating unit 129, the region extracting unit 261 under the control of the control unit 121 extracts a region of the second predetermined unit area including the target pixel groups 124 to be subjected to a noise reduction, from the color signals separated by the second separating unit 128.

Under the control of the control unit 121, the range setting unit 262 sets a noise range with respect to the target pixel groups 124, based on the noise amount $N_c$ estimated by the second noise estimating unit 129. More specifically, under the control of the control unit 121, the range setting unit 262 reads the average value $AV_c$ and the noise amount $N_c$ of the pixels in the region extracted by the region extracting unit 261, from the second noise estimating unit 129. After that, the range setting unit 262 sets the upper limit Noise_Up$_c$ and the lower limit Noise_Low$_c$ as the acceptable noise amount range, according to the following equations (19):

$$\text{Noise\_Up}_c = AV_c + N_c/2$$

$$\text{Noise\_Low}_c = AV_c - N_c/2 \tag{19}$$

The noise range, namely, the acceptable range of Noise_Up$_c$ to Noise_Low$_c$ set in the above manner, is transferred to the switching unit 263. The range setting unit 262 further transfers the average value $AV_c$ and the noise amount $N_c$ read from the second noise estimating unit 129 to the first smoothing unit 264 and the second smoothing unit 265.

Under the control of the control unit 121, the switching unit 263 reads the pixel value $P_c$ of the target pixel group 124 from the region extracting unit 261. The switching unit 263 then determines whether the pixel value $P_c$ falls within the acceptable range. The determination result is one of the following three: "within the noise range", "higher than the noise range", and "lower than the noise range". In the case of "within the noise range", the switching unit 263 transfers the pixel value $P_c$ of the target pixel group 124 to the first smoothing unit 264. In other cases, the switching unit 263 transfers the pixel value $P_c$ of the target pixel group 124 to the second smoothing unit 265.

The first smoothing unit 264 performs the smoothing processing to assign the average value $AV_c$ supplied from the range setting unit 262, to the pixel value $P_c$ of the target pixel group 124 supplied from the switching unit 263, as expressed by the following equation (20):

$$P_c = AV_c \tag{20}$$

When the value of the target pixel group 124 in the pixel region extracted by the region extracting unit 261 does not fall within the noise range set by the range setting unit 262, the second smoothing unit 265 performs a correcting processing on the pixel value. More specifically, the second smoothing unit 265 performs a correcting processing on the pixel value $P_c$ of the target pixel group 124 supplied from the switching unit 263, using the average value $AV_c$ and the noise value $N_c$ supplied from the range setting unit 262.

First, in the case of "higher than the noise range", a correcting processing is performed according to the following equation (21):

$$P_c = AV_c - N_c/2 \tag{21}$$

In the case of "lower than the noise range", a correcting processing is performed according to the following equation (22):

$$P_c = AV_c + N_c/2 \tag{22}$$

The processing result of the first smoothing unit 264 or the second smoothing unit 265 is transferred to the signal processing unit 110.

With the above described structures of the second noise estimating unit 129 and the second noise reducing unit 130, noise amount estimation can be performed in accordance with dynamically varying conditions such as the signal level, the temperature at the time of image capturing, and the gain. Also, an optimum noise reduction in the entire screen can be performed. Accordingly, high-quality signals can be obtained. Even if the above mentioned information is not obtained, noise amount estimation can be performed with the use of the standard values. Accordingly, a stable noise reducing effect can be achieved. Furthermore, by purposefully omitting a part of parameter calculations, an imaging system that requires lower costs and less power consumption can be provided. Also, with the use of a lookup table in the noise amount calculation, high-speed noise amount estimation can be performed. Since the acceptable range is set according to noise amounts in a noise reducing processing, the original signals can be retained with high precision, and discontinuity can be prevented.

Under the control of the control unit 121, the signal processing unit 110 converts the frame signal that is formed with the noise-reduced four-color signals of B, G, Ye, and R, and is transferred from the second noise reducing unit 130, into frame signal formed with the regular three-color signals B, G, and R. The signal processing unit 110 then performs known gradation processing and enhancement processing on the converted frame signal, to calculate the regular color image signal. The calculated regular color image signal is transferred to the second output unit 120, and the second output unit 120 displays the regular color image signal as the second output signal.

As described above, in accordance with the second embodiment, color image signal processed in a regular manner is calculated independently. Accordingly, an entire image signal can be recognized, and higher user friendliness can be achieved. Also, a noise amount is estimated for each of the color signals required to calculate the regular color image signal from image signal. Based on the estimated noise amount, a noise reducing processing is performed, and regular color image signal is calculated from the noise-reduced color signals. Since a noise reducing processing is also performed on the color image signal processed in a regular manner, the visibility can be improved for users.

In the above described second embodiment, a structure is configured to perform two types of noise reducing processing with the noise estimating unit 112 and the noise reducing unit 113, and the second noise estimating unit 129 and the second noise reducing unit 130. However, the present invention is not limited to that structure.

For example, the noise estimating unit 112 and the noise reducing unit 113 also have the functions of the second noise estimating unit 129 and the second noise reducing unit 130 through appropriate switching processing.

In such a case, as shown in FIG. 39, the second output unit 120, the second noise estimating unit 129, and the second noise reducing unit 130 are removed from the structure illustrated in FIG. 25, and a switching unit 125 is added to the structure. The basic structure is the same as the structure illustrated in FIG. 25, and the same components as those in the second embodiment are referred to using the same names and denoted by the same reference numerals as those in the second embodiment. In the following, only the different aspects from the second embodiment are described.

The buffer 107 is connected to the switching unit 125. The switching unit 125 is connected to the separating unit 111 and the second separating unit 128. The second separating unit 128 is connected to the noise estimating unit 112 and the noise reducing unit 113. The noise reducing unit 113 is connected to the signal processing unit 110 and the interpolating unit 114. The signal processing unit 110 is connected to the first output unit 117. The switching unit 125 and the control unit 121 are bidirectionally connected.

When an instruction to display the regular color image is issued from a user via the external interface unit 122, the switching unit 125 enters a regular mode, under the control of the control unit 121. In the regular mode, the switching unit 125 selects a single frame signal formed with the four-color signals of R, Ye, G, and B from the buffer 107, and transfers the frame signal to the second separating unit 128. The second separating unit 128 then separates the color signals in the manner described in the above second embodiment, and outputs the separated color signals to the noise estimating unit 112 and the noise reducing unit 113. Under the control of the control unit 121, the noise estimating unit 112 and the noise reducing unit 113 are switched to the same noise reducing processing as the noise reducing processing performed by the second noise estimating unit 129 and the second noise reducing unit 130 in the second embodiment. The noise reducing unit 113 then output noise-reduced four-color signals to the signal processing unit 110. The signal processing unit 110 then performs the processing described in the above second embodiment, and transfers the regular color image signal to the first output unit 117. The first output unit 117, which is a display monitor, for example, displays the regular color image signal.

When an instruction to output the results of discrimination of the subject to be discriminated is issued from a user via the external interface unit 122, the switching unit 125 enters a discrimination mode, under the control of the control unit 121. In the discrimination mode, the switching unit 125 reads the single frame signal formed with four-color signals, and transfers the frame signal to the separating unit 111. The separating unit 111 separates the input frame signal into wavelength ranges suitable for the subject to be discriminated, as described in the second embodiment, and outputs the separated frame signals to the noise estimating unit 112 and the noise reducing unit 113. Under the control of the control unit 121, the noise estimating unit 112 and the noise reducing unit 113 are switched to the noise reducing processing described in the first embodiment, and transfer the frame signal about the existence of the discrimination subject to the output unit 117 via the interpolating unit 114, the calculating unit 115, and the falsely-colored processing unit 116. The transferred frame signal is then displayed.

In the above described second embodiment, the discrimination apparatus is a structure integrally formed with the image acquisition unit including the imaging lens unit 100, the CCD 101, the illuminating lens unit 102, the illuminating light source 103, the optical fibers 104, the amplifier unit 105, the ADC 106, the WB unit 108, and the measured light evaluating unit 109. However, the present invention is not limited to that structure.

For example, as described as a modification of the first embodiment with reference to FIG. 19, an image signal generated from an independent image acquisition device may be stored as unprocessed Raw data on a recording medium such as a hard disk or a memory card, with additional information being recorded on the header portion. The additional information indicates the image acquisition conditions with respect to the subject to be discriminated, the color imaging system, the illuminating light, and the like. The signal and the header information may be read from the recording medium. Alternatively, an image signal transmitted via a wireless or wired network may be received and processed.

In the above described second embodiment, the processing is conducted by the hardware. However, the present invention is not limited to such. For example, processing may be performed by software through a computer (not shown). In such a case, an image signal from the CCD 101 is stored as unprocessed Raw data and the information such as the image acquisition conditions of the subject to be discriminated, the color imaging system, and the illuminating light, the temperature value of the color imaging system, and the gain value with respect to the image signal is output as header information from the control unit 121. The image signal and the header information are then input to the computer.

FIG. 40 is a flowchart of a software signal processing to be performed by the computer (not shown). This modification is basically the same as the modification of the first embodiment illustrated in FIG. 20, and only the different aspects from the modification of the first embodiment are described in the following.

The procedures of steps S101 through S106 are the same as those of the corresponding modification of the first embodiment. In this modification, image signal from a single CCD having the filter 131 formed with the four kinds of color filters shown in FIG. 26 is assumed to be processed. At step S105, particular coefficients such as the elements $m_{111}$ and $m_{112}$ and the elements $m_{211}$ and $m_{222}$ of the inverse matrixes $M_1^{-1}$ and $M_2^{-1}$ to be used to calculate the weighting coefficients about basis vectors are calculated, for example.

The procedures of steps S110 through S118 and steps S108 and S109 are also carried out as described in the corresponding modification of the first embodiment. In the noise estimating processing of step S111, however, the procedures of step S222, S225, and S226 are omitted. In the multiplying and adding processing of step S117, a multiplying and adding processing to calculate the weighting coefficients about the special basis vectors is performed according to the equation (15) and the equation (17), if the subject to be discriminated is oxyhemoglobin, for example. More specifically, the weighting coefficient ($w3_{1ij}$) about the special basis vector ($O3(\lambda_1)$) is calculated according to the equation (15) for the four frame signals of the color signals in the short wavelength range, and the weighting coefficient ($w3_{2ij}$) about the special basis vector ($O3(\lambda_2)$) is calculated according to the equation (17) for the four frame signals of the color signals in the long wavelength range.

If an instruction to output regular color image signal is detected at step S107, the second separating processing, described later in detail, is performed to separate the color signals for generating the regular color image signal from the image signal formed with the N kinds (N being a natural number of 2 or greater) of color signals (four kinds in this embodiment) that are input at step S101 (step S119).

After that, a region of the second predetermined unit area including a target pixel group formed with the target pixel of each of the color signals to be subjected to a noise reduction is extracted from one of the separated color signals (step S120). The second noise estimating processing, described later in detail, is then performed to estimate the noise amount with respect to the extracted region (step S121). Further, the second noise reducing processing, described later in detail, is performed to reduce noise with respect to the target pixel group in the region, based on the estimated noise amount (step S122). After that, a check is made to determine whether the noise reducing processing has been performed on all the pixel regions of the separated color signal (step S123). If the noise reducing processing is not completed, the processing returns to step S120. The target pixel group is then updated, and the next region is extracted.

If the noise reducing processing is determined to have been performed on all the pixel regions at step S123, a check is made to determine whether the noise reducing processing has been performed on all the color signals separated at step S120 (step S124). If the noise reducing processing is determined not to have been performed on all the color signals, the processing returns to step S120, and a region of the second predetermined unit area including a target pixel group to be subjected to a noise reduction is extracted from the next color signal.

If the noise reducing processing is determined to have been performed on all the color signals at step S124, the noise-reduced frame signal formed with four-color signals is converted into a frame signal formed with regular three-color signals R, G, and B, and missing color signals are generated by a known interpolating technique. In this manner, a frame signal formed with color signals for generating regular color image signal is generated. Signal processing such as the known gradation processing and enhancement processing is then performed, to generate the regular color image signal (step S107). The regular color image signal is then output in frame signal unit to a display monitor or the like (not shown) connected to the computer (step S108). After that, a check is made to determine whether all the frame signals have been processed (step S109). If the processing on all the frame signals is not completed, the processing returns to step S106. If the processing is completed, the processing comes to an end.

In the separating processing at step S110, a wavelength range table that outputs wavelength ranges based on the known spectral characteristics of the subject to be discriminated is first input (step S215), as shown in FIG. 41. The wavelength range table may be loaded from a recording medium provided in the computer or a recording medium detachably attached to the computer, or may be loaded via a network.

Based on the information about the subject to be discriminated in the header information that is input at step S101, wavelength ranges are determined from the wavelength range table. Based on the determined wavelength ranges, the color signals corresponding to the M kinds of frequency ranges are selected and separated from the image signal that is the single frame signal formed with the N kinds of color signals that are input at step S101 (step S216).

In the second separating processing at step S119, a filter table that outputs wavelength ranges based on the information about the color imaging system is first input (step S241), as shown in FIG. 42. This filter table may be loaded from a recording medium provided in the computer or a recording medium detachably attached to the computer, or may be loaded via a network.

Based on the information about the color imaging system in the header information that is input at step S101, wavelength ranges are determined from the filter table. Based on the determined wavelength ranges, the color signals corresponding to the M kinds of frequency ranges are selected and separated from the image signal that is the single frame signal formed with the N kinds of color signals that are input at step S101 (step S242).

In the second noise estimating processing at step S121, the information such as the temperature value and the gain value contained in the header information that is input at step S101 is first set as the noise-related information to be used in the noise estimating processing (step S251), as shown in FIG. 43. If the information such as the temperature value and the gain value is not contained in the header information, standard values may be loaded from a recording medium provided in the computer or a recording medium detachably attached to the computer, or may be loaded via a network.

After that, the low-frequency components are calculated from the region of the second predetermined unit area extracted at step S111, to calculate the low-frequency components of the regions of the respective color signals (step S252). With the use of the noise amount table that is input at step S104, the noise amount $N_c$ of the pixels in the region is calculated from the noise-related information that is set at step S251 and the signal level that is calculated at step S252 (step S253). The calculated noise amount $N_c$ of each color signal is assigned to the target pixel group 124 included in the region, and the low-frequency components of each color signal calculated at step S252 is output as the average value $AV_c$ of the pixels in the region. In this manner, the noise amount $N_c$ and the average value $AV_c$ are output (step S254).

In the second noise reducing processing at step S122, the upper limit Noise_Up$_c$ and the lower limit Noise_Low$_c$ as the acceptable noise amount range according to the equations (19) are first set, based on the average value $AV_c$ and the noise amount $N_c$ of the pixels estimated in the second noise estimating processing of step S121 (step S261), as shown in FIG. 44.

After that, the pixel value $P_c$ of the target pixel group 124 is read from the region extracted at step S120, and a check is made to determine whether the pixel value $P_c$ falls within the acceptable range (step S262). The determination result is one of the following three: "within the noise range", "higher than the noise range", and "lower than the noise range".

If the pixel value $P_c$ of the target pixel group 124 in the extracted region is determined to fall within the noise range, the first smoothing processing according to the equation (20) is performed to set the average value $AV_c$ as the value of the target pixel group 124 (step S263).

If the pixel value $P_c$ of the target pixel group 124 in the extracted pixel region is determined not to fall within the noise range, the second smoothing processing according to the equation (21) or (22) is performed to correct the pixel value $P_c$ of the target pixel group 124 with the use of the average value $AV_c$ and the noise amount $N_c$ estimated at step S121 (step S264).

The result of the first smoothing processing or the second smoothing processing is then output as a noise-reduced signal (step S235).

The regular color image signal and the false color image signals as the result of discrimination are output at step S108. A plurality of display monitors or the like may be connected to the computer, and the regular color image signal may be displayed separately from the false color image signals. Alternatively, only one display monitor or the like may be connected to the computer, and the regular color image signal may be displayed in a window other than the window in which the false color image signals are displayed.

Also, the display on a single display monitor may be switched by a user. In such a case, the procedures of steps S119 through 5124 and step S107 and the procedures of steps S110 through S118 are not necessarily carried out in parallel, and a user may select either the procedures of steps S119 through S124 and step S107 or the procedures of steps S110 through S118.

By referring now to FIG. 45, a microscope including a discrimination apparatus in accordance with a third embodiment of the present invention is described. The structure of the discrimination apparatus in accordance with this embodiment is the same as that of the first embodiment illustrated in FIG. 1, except that the calculating unit 115 is replaced with a correlation coefficient calculating unit 132 and a derivation coefficient ROM 133. The correlation coefficient calculating unit 132, the derivation coefficient ROM 133, the falsely-colored processing unit 116, and the first output unit 117 function as a discriminating unit that performs a discriminating processing on the subject to be discriminated, based on the color signals in the wavelength ranges that are noise-reduced by the noise reducing unit 113. The basic structure is the same as the structure of the first embodiment, and the same components as those in the first embodiment are referred to using the same names and denoted by the same reference numerals as those in the first embodiment. In the following, only the different aspects from the first embodiment are described.

In this embodiment, an image signal formed by the CCD 101 of the microscope is amplified by the amplifier unit 105, and is converted into digital signal by the ADC 106. The illuminating light emitted from the illuminating light source 103 is guided onto the object stage of the microscope via the illuminating lens unit 102. The interpolating unit 114 is connected to the correlation coefficient calculating unit 132. The derivation coefficient ROM 133 is connected to the correlation coefficient calculating unit 132. The correlation coefficient calculating unit 132 is connected to the falsely-colored processing unit 116. The control unit 121 is bidirectionally connected to the correlation coefficient calculating unit 132.

The functions of the discrimination apparatus of this embodiment are also basically the same as those of the first embodiment, and therefore, only the different aspects from the first embodiment are described below.

By referring to FIG. 45, the signal flows are described. After the image acquisition conditions about the subject to be discriminated as described later are set by a user through the external interface unit 122, a shutter button (not shown) provided on the external interface unit 122 is pressed halfway, to put the microscope into a pre-image acquisition mode. An image signal acquired at the CCD 101 is output as analog signal. The analog signal is amplified by the amplifier unit 105 by predetermined amounts, and is converted into digital signal by the ADC 106. The digital signal is transferred to the buffer 107. The image signal in the buffer 107 is then transferred to the WB unit 108 and the measured light evaluating unit 109, under the control of the control unit 121. The WB unit 108 performs a white balancing processing, and the measured light evaluating unit 109 performs an exposure controlling processing, as in the first embodiment.

The user then presses the shutter button provided on the external interface unit 122, to perform image acquisition. An image signal is transferred to the buffer 107, as in the pre-image acquisition mode. The image signal in the buffer 107 is read by the signal processing unit 110 and the separating unit 111.

As described in the first embodiment, the signal processing unit 110 calculates a regular color image signal, and the second output unit 120 displays the regular color image signal, under the control of the control unit 121.

As described in the first embodiment, the separating unit 111, under the control of the control unit 121, selects and separates the color signals corresponding to M kinds (M being a natural number of 1 or greater) of frequency ranges (two kinds in this embodiment) to be used in the later described signal processing with the use of basis vectors, from a single frame signal formed with N kinds (N being a natural number of 2 or greater, $M \leq N$) of color signals (six kinds in this embodiment) recorded in the buffer 107. Under the control of the control unit 121, the noise estimating unit 112 estimates noise amounts in predetermined unit areas in each of the wavelength ranges separated by the separating unit 111, as described in the first embodiment. Under the control of the control unit 121, the noise reducing unit 113 performs a noise reducing processing on each of the wavelength ranges separated by the separating unit 111, based on the noise amounts estimated by the noise estimating unit 112, as described in the first embodiment. Under the control of the control unit 121, the interpolating unit 114 reads the signals of the noise-reduced wavelength ranges from the noise reducing unit 113, and generates six kinds of frame signals formed with six kinds of color signals by a known interpolating technique, as described in the first embodiment. The six kinds of frame signals are sequentially transferred in frame signal unit to the correlation coefficient calculating unit 132.

In the derivation coefficient ROM 133, the derivation coefficients that derive the correlations between the known spectral characteristics of the subject to be discriminated and the color signals in the wavelength ranges, which are noise-reduced by the noise reducing unit 113 and interpolated and generated by the interpolating unit 114, are stored for each subject to be discriminated. The derivation coefficients are calculated beforehand, based on the known spectral characteristics of the subject, the spectral characteristics about the color imaging system to be used to capture image of the subject, and the spectral characteristics about the illuminating light to be used to capture image of the subject. The calculated derivation coefficients are stored beforehand in the derivation coefficient ROM 133 for each subject to be discriminated.

The correlation coefficient calculating unit 132 reads the derivation coefficients from the derivation coefficient ROM 133, under the control of the control unit 121 that functions in accordance with the selection of the subject to be discriminated under the image acquisition conditions set through the external interface unit 122. After that, the correlation coefficients between the known spectral characteristics of the subject to be discriminated and the signals in the wavelength ranges are calculated with the use of the loaded derivation coefficients, for each of the color signals transferred from the interpolating unit 114. The correlation coefficients calculated by the correlation coefficient calculating unit 132 are values proportional to the existence of the subject to be discriminated, and are transferred to an output signal calculating unit formed with the falsely-colored processing unit 116 and the first output unit 117.

The falsely-colored processing unit 116 first normalizes the correlation coefficients transferred from the correlation coefficient calculating unit 132, to the signal level of image signal ("0" to "255", if the signal level is 8 bits). Different colors are then assigned to the normalized correlation coefficients, to generate false color image signals. In this embodiment, red is assigned to the correlation coefficients of B1, B2, and G1 of the short wavelength range, and cyan is assigned to the correlation coefficients of G2, R1, and R2 of the long wavelength range. The falsely-colored processing unit 116 transfers the false color image signals generated in this manner to the first output unit 117. The first output unit 117 then displays the false color image signals of the wavelength ranges independently of each other with respect to the subject to be discriminated. Since the first output unit 117 displays the output signal combined with the falsely-colored correlation coefficients of the short wavelength range and the falsely-colored correlation coefficients of the long wavelength range, the portion in which the subject to be discriminated exists only in the short wavelength range is displayed in red. Likewise, the portion in which the subject to be discriminated exists only in the long wavelength range is displayed in cyan. The portion in which the subject to be discriminated exists both in the short wavelength range and the long wavelength range is displayed in white (red+cyan). The portion in which the subject to be discriminated exists neither in the short wavelength range nor in the long wavelength range is displayed in black. In this manner, the output signal as the results of discrimination of the subject to be discriminated is output. The short wavelength range represents the information about the surface layer of the subject, and the long wavelength range represents the information about the deep layer of the subject.

The first output unit 117 and the second output unit 120 are not limited to liquid crystal displays, but may be other recording media such as hard disks or memory cards on which frame signals are sequentially recorded and stored.

As shown in FIG. 46, the correlation coefficient calculating unit 132 includes a coefficient selecting unit 271 and a multiplying/adding unit 272. The derivation coefficient ROM 133 is connected to the multiplying/adding unit 272 via the coefficient selecting unit 271. The interpolating unit 144 is connected to the multiplying/adding unit 272. The multiplying/adding unit 272 is connected to the falsely-colored processing unit 116. The control unit 121 is bidirectionally connected to the coefficient selecting unit 271 and the multiplying/adding unit 272.

The coefficient selecting unit 271 receives the information about the subject to be discriminated under the image acquisition conditions set through the external interface unit 122, from the control unit 121. According to the information, the coefficient selecting unit 271 reads the derivation coefficients to derive the correlations between the known spectral characteristics of the subject to be discriminated and the respective color signals, from the derivation coefficient ROM 133. In this manner, the derivation coefficient ROM 133 and the coefficient selecting unit 271 function as a derivation coefficient acquiring unit. In the derivation coefficient ROM 133, the elements of the inverse matrixes $M^{-1}$ of the system matrixes expressed by the equations (5) and (6) are stored as the derivation coefficients. Since the two wavelength ranges are assumed in this embodiment, the number of inverse matrixes $M^{-1}$ of the system matrixes is also two. The size of each inverse matrix of the system matrixes is 3×3 in each wavelength range. In the microscope of this embodiment, the spectral characteristics about the color imaging system to be used to capture image of subject and the spectral characteristics about the illuminating light to be used to capture image of subject with the color imaging system are assumed to be fixed. In this case, the inverse matrixes $M^{-1}$ of the system matrixes finally obtained are fixed. Accordingly, the calculations expressed by the equations (5) and (6) can be omitted, provided the inverse matrixes $M^{-1}$ are recorded.

Several kinds of basis vectors based on the known spectral characteristics of the subjects to be discriminated are prepared in advance, and the inverse matrixes $M^{-1}$ of the system matrixes are recorded. The derivation coefficients are transferred to the multiplying/adding unit 272.

Under the control of the control unit 121, the multiplying/adding unit 272 reads the derivation coefficients from the coefficient selecting unit 271, and the color signals of each of the wavelength ranges in pixels from the interpolating unit 114. After that, the weighting coefficients are determined according to the equations (9) and (10). The weighting coefficients serve as the correlation coefficients representing the correlations between the known spectral characteristics of the subject to be discriminated and the color signals in the wavelength ranges. The correlation coefficients are sequentially transferred to the falsely-colored processing unit 116.

As described above, in accordance with the third embodiment, the correlation coefficients between the known spectral characteristics of the subject to be discriminated and the color signals are determined for the respective noise-reduced wavelength ranges independently of one another, from the derivation coefficients based on the known spectral characteristics of the subject to be discriminated. The correlation coefficients are values proportional to the existence of the subject to be discriminated. Based on the correlation coefficients, output signals as the results of discrimination of the subject to be discriminated with the known spectral characteristics are calculated. As described above, the derivation coefficients based on the spectral characteristics of the subject to be discriminated are used, so that the correlation coefficients having the values proportional to the existence of the subject to be discriminated can be calculated in the third embodiment. Accordingly, there is no need to perform signal processing allowing errors such as approximations according to the conventional least squares method. In this manner, errors caused by signal processing are reduced, and highly-reliable discrimination can be performed.

Since the regular broadband illuminating light is used, the influence of noise can be reduced, and stable discrimination can be performed. Furthermore, it is easy to calculate the correlation coefficients from the derivation coefficients, and an output signal is calculated directly from the correlation coefficients. Accordingly, high-speed operations and lower costs can be realized.

Since signal processing is performed for the color signals independently of one another in particular wavelength ranges, the blood vessels in the surface layer can be discriminated from the color signals of the short wavelength range, for example, and the blood vessels in the deep layer can be discriminated from the color signals of the long wavelength range, for example. In this manner, information at desired depths can be obtained.

Also, since an output signal is obtained by normalizing the correlation coefficients with respect to the derivation coefficients, high-precision output signal about the existence of the subject to be discriminated can be obtained in the third embodiment.

By assigning different colors independently of one another in each of the wavelength ranges, the separation capacity with respect to the wavelength ranges or the information about the respective depths is increased, and discrimination can be performed with high precision. Also, since an image signal subjected to conventional processing is output independently, entire image signal is easily recognized, and higher user friendliness can be achieved.

In the above description of the third embodiment, still image processing is performed in the microscope. However, the present invention is not limited to such. As long as the spectral characteristics about the color imaging system and the spectral characteristics about the illuminating light to be used to capture image of subject are fixed, the third embodiment, like the first and second embodiments, may be applied to video image processing in an endoscope of the frame sequential type. Also, the first and second embodiments may be applied to still image processing.

Further, an image signal generated from an independent image acquisition device may be stored as unprocessed Raw data on a recording medium, with additional information being recorded on the header portion. Here, additional information refers to the image acquisition conditions with respect to the subject to be discriminated and the like. The signal and the header information may be read from the recording medium, and processed. This embodiment may also be applied to a structure that obtains color signals with the use of two CCD or three CCD.

In the third embodiment, regular color image signal is displayed on the second output unit 120, and the false color image signals about the existence of the subject to be discriminated are displayed on the first output unit 117. However, the present invention is not limited to such arrangement.

For example, in the structure illustrated in FIG. 47, an enhancement processing may be performed on regular color image signal, based on the correlation coefficients with respect to the derivation coefficients, and the regular color image signal may be displayed as an output signal. The structure illustrated in FIG. 47 is the same as the structure illustrated in FIG. 45, except that the falsely-colored processing unit 116 and the first output unit 117 are removed, and an enhancement processing unit 134 is added. The basic structure is the same as the structure illustrated in FIG. 45, and the same components as those in the third embodiment are referred to using the same names and denoted by the same reference numerals as those in the third embodiment. In the following, only the different aspects from the third embodiment are described.

The signal processing unit 110 and the correlation coefficient calculating unit 132 are connected to the enhancement processing unit 134. The enhancement processing unit 134 is connected to the second output unit 120. The control unit 121 is bidirectionally connected to the enhancement processing unit 134. Regular color image signal is transferred from the signal processing unit 110 to the enhancement processing unit 134, and the correlation coefficients between the spectral characteristics of the subject to be discriminated and the color signals in the wavelength ranges are transferred from the correlation coefficient calculating unit 132 to the enhancement processing unit 134.

In this structure, the enhancement processing unit 134, under the control of the control unit 121, reads the regular color image signal from the signal processing unit 110, and reads the correlation coefficients from the correlation coefficient calculating unit 132. The enhancement processing unit 134 then performs an enhancement processing on the regular color image signal transferred from the signal processing unit 110, based on the correlation coefficients transferred from the correlation coefficient calculating unit 132. As the enhancement processing, a known saturation enhancement processing is performed, and the amounts of enhancement are proportional to the correlation coefficients. The enhanced frame signal is transferred to the second output unit 120. Accordingly, the second output unit 120 displays the regular color image signal enhancing the region in which the subject to be discriminated exists in each of the wavelength ranges. More specifically, only the region in which the subject such as oxyhemoglobin exists is enhanced, so that higher visibility can be achieved. Since the enhancement processing can be performed in the respective wavelength ranges independently of one another, the separation capacity with respect to the information about the respective depths is increased, and discrimination can be performed with high precision. Also, color image signal subjected to regular processing is output with respect to the regions in which the subject to be discriminated does not exist or the regions other than the region in which the subject exists. Accordingly, entire image signal can be more easily recognized, and the user friendliness becomes higher.

As shown in FIG. 48, the enhancement processing unit 134 includes a luminance and color-difference separating unit 281, a buffer 282, an emphasis gain calculating unit 283, an enhancement function ROM 284, a gain multiplying unit 285, and a luminance and color-difference combining unit 286. The signal processing unit 110 is connected to the buffer 282 via the luminance and color-difference separating unit 281. The buffer 282 is connected to the gain multiplying unit 285 and the luminance and color-difference combining unit 286. The correlation coefficient calculating unit 132 and the enhancement function ROM 284 are connected to the enhancement gain calculating unit 283. The enhancement gain calculating unit 283 is connected to the gain multiplying unit 285. The gain multiplying unit 285 is connected to the luminance and color-difference combining unit 286. The luminance and color-difference combining unit 286 is connected to the second output unit 120. The control unit 121 is bidirectionally connected to the luminance and color-difference separating unit 281, the enhancement gain calculating unit 283, the gain multiplying unit 285, and the luminance and color-difference combining unit 286.

Under the control of the control unit 121, the luminance and color-difference separating unit 281 calculates a luminance signal $Y_{ij}$ and color-difference signals $Cb_{ij}$ and $Cr_{ij}$ with respect to the regular color image signal $R_{ij}$, $G_{ij}$, $B_{ij}$, which is transferred from the signal processing unit 110. The calculation is performed according to the following equations (23):

$$Y_{ij} = 0.29900 R_{ij} + 0.58700 G_{ij} + 0.11400 B_{ij}$$

$$Cb_{ij} = -0.16874 R_{ij} - 0.33126 G_{ij} + 0.50000 B_{ij}$$

$$Cr_{ij} = 0.50000 R_{ij} - 0.41869 G_{ij} - 0.08131 B_{ij} \qquad (23)$$

The calculated luminance signal and the color-difference signals are transferred to and recorded in the buffer 282.

Meanwhile, the enhancement gain calculating unit 283 reads the correlation coefficients from the correlation coefficients, under the control of the control unit 121. The enhancement gain calculating unit 283 also reads a gain table for determining enhancement gains from the enhancement function ROM 284.

FIG. 49 shows an example of the enhancement gain table recorded in the enhancement function ROM 284. This table is a table that outputs enhancement gains, with the inputs being correlation coefficients. According to this table, the enhancement gain calculating unit 283 calculates the gains with respect to the loaded correlation coefficients. The correlation coefficients are assumed to have values of "0" to "1". In this embodiment, two correlation coefficients with respect to oxyhemoglobin and deoxyhemoglobin are obtained, but the average value of the two correlation coefficients is used to calculate the gains. The gains are calculated for the short wavelength range ($gain_{sij}$) and the long wavelength range ($gain_{lij}$) independently of each other.

The gains $\text{gain}_{sij}$ and $\text{gain}_{lij}$ calculated by the enhancement gain calculating unit 283 are transferred to the gain multiplying unit 285. Under the control of the control unit 121, the gain multiplying unit 285 reads the color-difference signals $Cb_{ij}$ and $Cr_{ij}$ from the buffer 282, and reads the gains $\text{gain}_{sij}$ and $\text{gain}_{lij}$ from the enhancement gain calculating unit 283. After that, the enhancement processing expressed by the following equations (24) is performed on the color-difference signals $Cb_{ij}$ and $Cr_{ij}$:

$$Cb'_{ij} = \text{gain}_{lij} \cdot Cb_{ij}$$

$$Cr'_{ij} = \text{gain}_{sij} \cdot Cr_{ij} \quad (24)$$

In the enhancement processing expressed by the above equations (24), Cb (the blue end) is emphasized based on the weighting coefficients of the long wavelength range about the blood vessels in the deep layer, and Cr (the red end) is emphasized based on the weighting coefficients of the short wavelength range about the blood vessels in the surface layer. Accordingly, the short wavelength range and the long wavelength range can be discriminated from each other. The color-difference signals $Cb'_{ij}$ and $Cr'_{ij}$ subjected to the enhancement are then transferred to the luminance and color-difference combining unit 286.

Under the control of the control unit 121, the luminance and color-difference combining unit 286 reads the luminance signal $Y_{ij}$ from the buffer 282, and reads the color-difference signals $Cb'_{ij}$ and $Cr'_{ij}$ subjected to the enhancement from the gain multiplying unit 285. The enhancement processing expressed by the following equations (25) is then performed to calculate the regular color image signal subjected to enhancement:

$$R'_{ij} = Y_{ij} + 1.40200 Cr'_{ij}$$

$$G'_{ij} = Y_{ij} - 0.34414 Cb'_{ij} - 0.71414 Cr'_{ij}$$

$$B'_{ij} = Y_{ij} + 1.77200 Cb'_{ij} \quad (25)$$

The regular color image signal subjected to the enhancement at the luminance and color-difference combining unit 286 are transferred to the second output unit 120.

In the above example, the surface layer is enhanced in red, and the deep layer is enhanced in blue. However, the present invention is not limited to that arrangement. By combining color signals Cb and Cr, enhancement can be performed with a desired color.

Since the subject to be discriminated is a blood vessel, the average value of the correlation coefficients about oxyhemoglobin and deoxyhemoglobin is used in the above example. However, the present invention is not limited to that arrangement. For example, oxyhemoglobin in the surface layer may be enhanced in red, deoxyhemoglobin in the surface layer may be enhanced in yellow, oxyhemoglobin in the deep layer may be enhanced in blue, and deoxyhemoglobin in the deep layer may be enhanced in green. In this manner, four kinds of subjects may be enhanced independently of one another.

In the third embodiment, hardware processing is performed, but the present invention is not limited to hardware processing. For example, an image signal from the CCD 101 may be stored as unprocessed Raw data and the information such as the image acquisition conditions of the subject to be discriminated and the like may be output as header information from the control unit 121. The image signal and the header information are then input to the computer, and are processed by the software.

Figure 50:
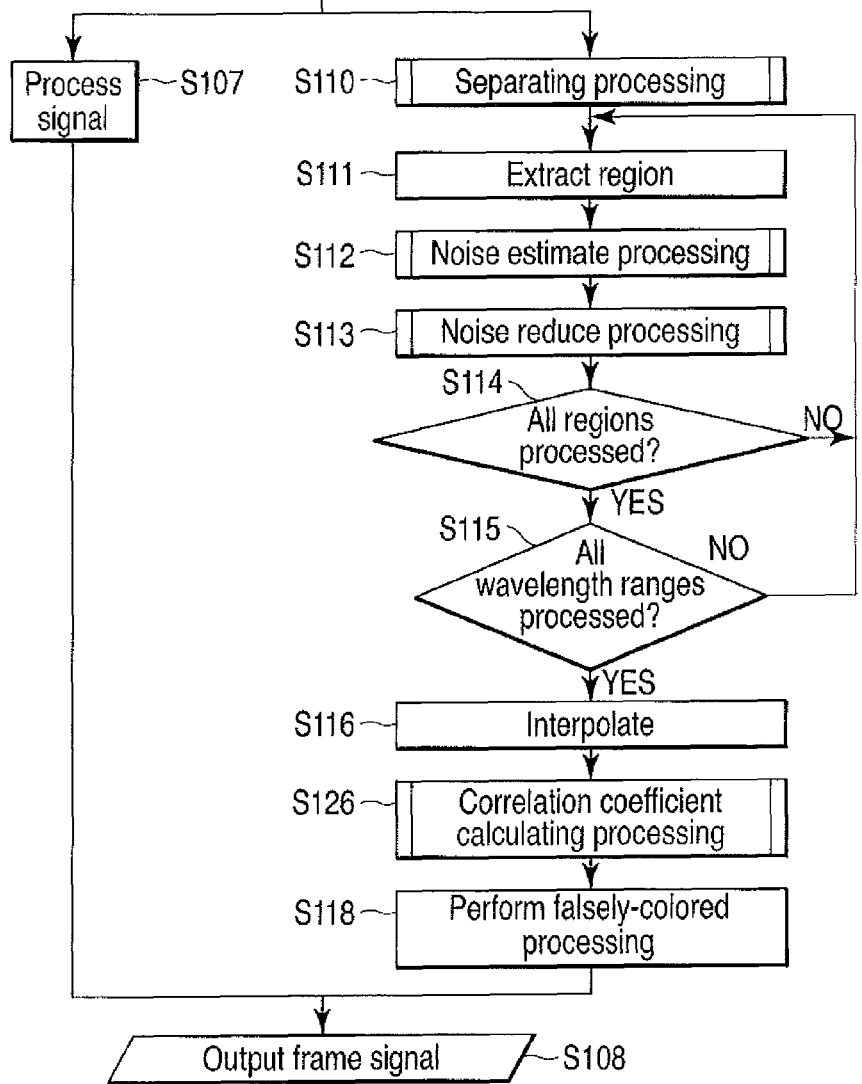
FIG. 50 is a flowchart of a software processing to perform signal processing in accordance with another modification of the third embodiment.

FIG. 50 is a flowchart of a software signal processing to be performed by the computer (not shown). The same steps as those of the flowchart of the signal processing in the first embodiment illustrated in FIG. 20 are denoted by the same reference numerals as those in FIG. 20.

As in the first embodiment, first, the computer is input with image signal and the header information about the information such as the image acquisition conditions of the subject to be discriminated, the color imaging system, and the illuminating light, the temperature value, and the gain value, basis vectors, system spectral characteristics, and a noise amount table at steps S101 through S104.

The computer is further input with derivation coefficients (step S125). The derivation coefficients may be loaded from a recording medium provided in the computer or a recording medium detachably attached to the computer, or may be loaded via a network.

After that, the color signals for generating regular color image signal are separated, and missing color signals are generated by a known interpolating technique. In this manner, a frame signal formed with the color signals for generating the regular color image signal is generated. Signal processing such as known gradation processing and enhancement processing is then performed to generate the regular color image signal (step S107). The regular color image signal is then output to a display monitor or the like (not shown) connected to the computer (step S108). The processing then comes to an end.

In the case of a microscope, still image is processed, instead of video image. Therefore, there is no need to make a check to determine whether all the frame signals have been processed, as in the first and second embodiments.

As in the first embodiment, at steps S110 through S115, the input image signal formed with the N kinds (N being a natural number of 2 or greater) of color signals (six kinds in this embodiment) is separated into the M kinds (M being a natural number of 1 or greater, M≦N) of wavelength ranges (two kinds in this embodiment), and a noise reducing processing is performed on each of the separated wavelength ranges. At step S116, a known interpolating processing is performed to generate six kinds of frame signals formed with six kinds of color signals from the signals of the noise-reduced wavelength ranges.

After that, the correlation coefficient calculating processing, described later in detail, is performed on the image signal formed with the color signals of each of the wavelength ranges, so as to calculate the correlation coefficients between the known spectral characteristics of the subject to be discriminated and the color signals in the wavelength ranges, based on the derivation coefficients that are input at step S125 (step S126).

The calculated correlation coefficients are normalized, and different colors independent of one another are assigned to the wavelength ranges with respect to the normalized correlation coefficients. In this manner, false color image signals are generated (step S118). The false color image signals about the existence of the subject to be discriminated are then output to a display monitor or the like (not shown) connected to the computer (step S108). The processing then comes to an end.

The regular color image signal and the false color image signals as the result of discrimination are output at step S108. Two or more display monitors or the like may be connected to the computer, and the regular color image signal may be displayed separately from the false color image signals. Alternatively, only one display monitor or the like may be connected to the computer, and the regular color image signal may be displayed in a window separated from the window in which the false color image signals are displayed.

Also, the display on a single display monitor may be switched by a user. In such a case, the procedure of step S107 and the procedures of steps S110 through S116 and steps S126 and S118 are not necessarily carried out in parallel, and a user may select either the procedure of step S107 or the procedures of steps S110 through S116 and steps S126 and 118.

Figure 51:
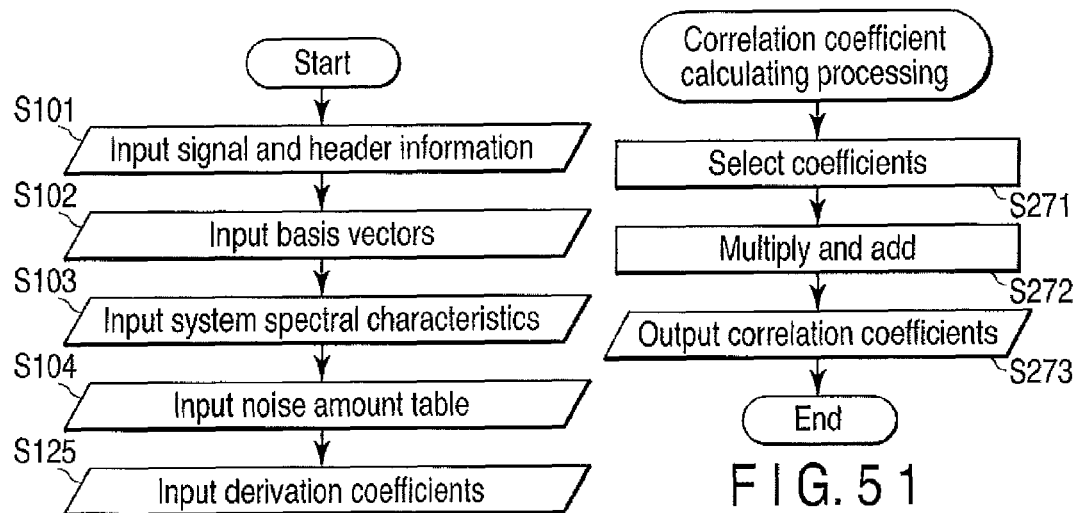
FIG. 51 is a flowchart of the correlation coefficient calculating processing.

In the correlation coefficient calculating processing at step S126, derivation coefficients are first selected from the derivation coefficients that are input at step S125, based on the information about the subject to be discriminated in the header information that is input at step S101 (step S271), as shown in FIG. 51. According to the equations (9) and (10), the correlation coefficients are then calculated based on the selected derivation coefficients (step S272), and the calculated correlation coefficients are output (step S273).

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A discrimination apparatus, comprising:
a separating unit configured to separate N kinds, N being a natural number of 3 or greater, of digital color signals forming a single frame digital image signal obtained by image acquisition of a subject with a color imaging system into M kinds, M being a natural number of 2 or greater, $M \leq N$, of wavelength ranges, based on known spectral characteristics of a subject to be discriminated, at least one of the M kinds of separated wavelength ranges including at least two of the N kinds of the digital color signals;
a noise estimating unit configured to estimate a noise amount in each predetermined unit area in each of the M kinds of wavelength ranges separated by the separating unit;
a noise reducing unit configured to perform a noise reducing processing on each of the M kinds of wavelength ranges separated by the separating unit, based on the noise amount estimated by the noise estimating unit; and
a discriminating unit configured to perform a discriminating processing on the subject to be discriminated, based on the digital color signals in the M kinds of wavelength ranges noise-reduced by the noise reducing unit.

2. The discrimination apparatus according to claim 1, further comprising
a signal processing unit configured to calculate a regular color image signal from the image signal formed with the N kinds of color signals obtained by image acquisition of the subject with the color imaging system.

3. The discrimination apparatus according to claim 2, further comprising
a switching unit configured to switch between a discrimination mode to acquire an image of the subject to be discriminated and a regular mode to obtain the regular color image signal,
wherein the separating unit, the noise estimating unit, and the noise reducing unit function when the switching unit switches to the discrimination mode.

4. The discrimination apparatus according to claim 2, wherein N is 4 or greater.

5. The discrimination apparatus according to claim 2, wherein spectral characteristics of color signals to be used at the signal processing unit are set in a wider band than spectral characteristics of color signals not to be used at the signal processing unit.

6. The discrimination apparatus according to claim 1, further comprising:
a second separating unit configured to separate color signals necessary for calculating a regular color image signal, from the image signal formed with the N kinds of color signals obtained by image acquisition of the subject with the color imaging system;
a second noise estimating unit configured to estimate a noise amount in each second predetermined unit area in each of the color signals separated by the second separating unit;
a second noise reducing unit configured to perform a noise reducing processing on each of the color signals separated by the second separating unit, based on the noise amount estimated by the second noise estimating unit; and
a signal processing unit configured to calculate the regular color image signal, based on the color signals noise-reduced by the second noise reducing unit.

7. The discrimination apparatus according to claim 6, wherein the second noise estimating unit comprises:
a region extracting unit configured to extract a region of the second predetermined unit area including a target pixel group formed with target pixels of each color signal to be subjected to a noise reduction, from the color signals separated by the second separating unit;
a low-frequency calculating unit configured to calculate a low-frequency component from the region extracted by the region extracting unit;
a collecting unit configured to collect information about a temperature value about the color imaging system and a gain value with respect to the image signal;
a providing unit configured to provide a standard value for information that is not collected by the collecting unit; and
a noise table unit configured to output a noise amount of the target pixel group included in the region of the second predetermined unit area, with inputs being the information supplied from one of the collecting unit and the providing unit and the low-frequency component calculated by the low-frequency calculating unit.

8. The discrimination apparatus according to claim 6, wherein the second noise reducing unit comprises:
a region extracting unit configured to extract a region including a target pixel group formed with target pixels of each color signal to be subjected to a noise reduction, from the color signals separated by the second separating unit;
a noise range setting unit configured to set a noise range for the target pixel group, based on the noise amount estimated by the second noise estimating unit;
a first smoothing unit configured to determine a value of the target pixel group to be a result of smoothing performed on values of all pixels in the region extracted by the region extracting unit, when the value of the target pixel group in the region extracted by the region extracting unit falls within the noise range that is set by the noise range setting unit; and
a second smoothing unit configured to correct the value of the target pixel group, when the value of the target pixel group in the region extracted by the region extracting unit does not fall within the noise range that is set by the noise range setting unit.

9. The discrimination apparatus according to claim 4, wherein spectral characteristics of color signals to be used at the signal processing unit are set in a wider band than spectral characteristics of color signals not to be used at the signal processing unit.

10. The discrimination apparatus according to claim 1, wherein the separating unit comprises:
   a predicting unit configured to predict an output value of each color signal, based on the known spectral characteristics of the subject to be discriminated and spectral characteristics of an imaging system including spectral characteristics about the color imaging system and spectral characteristics about illuminating light to be used in image acquisition of the subject with the color imaging system;
   a selecting unit configured to select color signals having similar output values to the output values of the respective color signals predicted by the predicting unit; and
   an adjusting unit configured to secure the M kinds of wavelength ranges by adjusting the number of color signals selected by the selecting unit.

11. The discrimination apparatus according to claim 1, wherein the separating unit comprises a wavelength range table unit configured to output the wavelength ranges, based on the known spectral characteristics of the subject to be discriminated.

12. The discrimination apparatus according to claim 1, wherein the noise estimating unit comprises:
   a region extracting unit configured to extract a pixel region of the predetermined unit area including a target pixel group formed with target pixels of each color signal to be subjected to a noise reduction, from the wavelength ranges separated by the separating unit;
   a low-frequency calculating unit configured to calculate a low-frequency component from the pixel region extracted by the region extracting unit;
   a collecting unit configured to collect information about a temperature value about the color imaging system and a gain value with respect to the image signal;
   a providing unit configured to provide a standard value for information that is not collected by the collecting unit; and
   a noise amount output unit configured to output a noise amount of the target pixel group, with inputs being the information supplied from one of the collecting unit and the providing unit and the low-frequency component calculated by the low-frequency calculating unit.

13. The discrimination apparatus according to claim 1, wherein the noise estimating unit comprises:
   a region extracting unit configured to extract a pixel region of the predetermined unit area including a target pixel group formed with target pixels of each color signal to be subjected to a noise reduction, from the wavelength ranges separated by the separating unit, the region extracting unit further extracting a color pixel region for each color signal from the extracted pixel region, the color pixel region including a target pixel of each corresponding color signal;
   a low-frequency calculating unit configured to calculate a low-frequency component of each of the color pixel regions extracted by the region extracting unit;
   a collecting unit configured to collect information about a temperature value about the color imaging system and a gain value with respect to the image signal;
   a providing unit configured to provide a standard value for information that is not collected by the collecting unit;
   a noise table unit configured to obtain noise amounts of pixels in the color pixel regions, with inputs being the information supplied from one of the collecting unit and the providing unit and the low-frequency components of the color pixel regions calculated by the low-frequency calculating unit; and
   an average value calculating unit configured to calculate an average value of the noise amount of the pixels in the respective color pixel regions obtained by the noise table unit, and output the calculated noise amount as a noise amount of the target pixel group included in the pixel region.

14. The discrimination apparatus according to claim 1, wherein the noise reducing unit comprises:
   a region extracting unit configured to extract a region including a target pixel group formed with target pixels of each color signal to be subjected to a noise reduction, from the wavelength ranges separated by the separating unit;
   a noise range setting unit configured to set a noise range for the target pixel group, based on the noise amount estimated by the noise estimating unit;
   a first smoothing unit configured to determine a value of the target pixel group to be a result of smoothing performed on values of all pixels in the region extracted by the region extracting unit, when the value of the target pixel group in the region extracted by the region extracting unit falls within the noise range that is set by the noise range setting unit; and
   a second smoothing unit configured to correct the value of the target pixel group, when the value of the target pixel group in the region extracted by the region extracting unit does not fall within the noise range that is set by the noise range setting unit.

15. The discrimination apparatus according to claim 1, wherein the discriminating unit comprises:
   a basis vector acquiring unit configured to acquire a special basis vector based on the known spectral characteristics of the subject to be discriminated;
   a system spectral characteristics acquiring unit configured to acquire spectral characteristics of an imaging system including spectral characteristics about the color imaging system and spectral characteristics of illuminating light to be used to acquire the image of the subject with the color imaging system;
   a calculating unit configured to calculate a weighting coefficient with respect to the special basis vector, based on the color signals in the wavelength ranges noise-reduced by the noise reducing unit, the special basis vector acquired by the basis vector acquiring unit, and the spectral characteristics of the imaging system acquired by the system spectral characteristics acquiring unit; and
   an output signal calculating unit configured to calculate an output signal as a result of discrimination of the subject having the known spectral characteristics, based on the weighting coefficient with respect to the special basis vector that is calculated by the calculating unit.

16. The discrimination apparatus according to claim 15, wherein the calculating unit comprises:
   a matrix calculating unit configured to calculate a system matrix about the imaging system, based on the special basis vector based on the known spectral characteristics of the subject that is obtained by the basis vector acquiring unit, and the spectral characteristics of the imaging system that are acquired by the system spectral characteristics acquiring unit;

an inverse matrix calculating unit configured to calculate an inverse matrix of the system matrix calculated by the matrix calculating unit;

a coefficient selecting unit configured to select a coefficient related to the special basis vector based on the known spectral characteristics of the subject to be discriminated, from coefficients of the inverse matrix of the system matrix that is calculated by the inverse matrix calculating unit; and a multiplying and adding unit configured to calculate the weighting coefficient with respect to the special basis vector based on the known spectral characteristics of the subject to be discriminated, based on the coefficient selected by the coefficient selecting unit and the color signals in the wavelength ranges noise-reduced by the noise reducing unit.

17. The discrimination apparatus according to claim 1, wherein the discriminating unit comprises:

a derivation coefficient acquiring unit configured to acquire derivation coefficients representing correlations between the known spectral characteristics of the subject to be discriminated and the color signals in the wavelength ranges noise-reduced by the noise reducing unit, the derivation coefficients being calculated based on the known spectral characteristics of the subject to be discriminated, spectral characteristics about the color imaging system, and spectral characteristics of illuminating light to be used to acquire of the image of the subject with the color imaging system;

a correlation coefficient calculating unit configured to calculate correlation coefficients between the known spectral characteristics of the subject to be discriminated and the color signals in the wavelength ranges noise-reduced by the noise reducing unit, based on the color signals in the wavelength ranges noise-reduced by the noise reducing unit and the derivation coefficients acquired by the derivation coefficient acquiring unit; and an output signal calculating unit configured to calculate an output signal as a result of discrimination of the subject having the known spectral characteristics, based on the correlation coefficients calculated by the correlation coefficient calculating unit.

18. The discrimination apparatus according to claim 1, wherein N is 4 or greater.

19. A discrimination method: comprising:

separating N kinds, N being a natural number of 3 or greater, of digital color signals forming a single frame digital image signal obtained by image acquisition of a subject with a color imaging system into M kinds, M being a natural number of 2 or greater, $M \leq N$, of wavelength ranges, based on known spectral characteristics of a subject to be discriminated, at least one of the M kinds of separated wavelength ranges including at least two of the N kinds of the digital color signals;

estimating a noise amount in each predetermined unit area in each of the M kinds of separated wavelength ranges;

performing a noise reducing processing on each of the M kinds of separated wavelength ranges, based on the estimated noise amount; and performing a discriminating processing on the subject to be discriminated, based on the digital color signals in the M kinds of noise-reduced wavelength ranges.

20. A program recording medium storing a program for causing a computer to:

separate N kinds, N being a natural number of 3 or greater, of digital color signals forming a single frame digital image signal obtained by image acquisition of a subject with a color imaging system into M kinds, M being a natural number of 2 or greater, $M \leq N$, of wavelength ranges, based on known spectral characteristics of a subject to be discriminated, at least one of the M kinds of separated wavelength ranges including at least two of the N kinds of the digital color signals;

estimate a noise amount in each predetermined unit area in each of the M kinds of separated wavelength ranges;

perform a noise reducing processing on each of the M kinds of separated wavelength ranges, based on the estimated noise amount; and perform a discriminating processing on the subject to be discriminated, based on the digital color signals in the M kinds of noise-reduced wavelength ranges.

* * * * *